(12) United States Patent
Tanga et al.

(10) Patent No.: US 9,796,674 B2
(45) Date of Patent: Oct. 24, 2017

(54) BENZYL UREA DERIVATIVES FOR ACTIVATING TGF-BETA SIGNALING

(71) Applicants: THE BOARD OF TRUSTEES OF THE LELAND STANFORD JUNIOR UNIVERSITY, Palo Alto, CA (US); SRI INTERNATIONAL, Menlo Park, CA (US)

(72) Inventors: Mary Jean Tanga, Los Altos, CA (US); Laura Ellen Downs Beaulieu, El Cerrito, CA (US); Anton Wyss-Coray, Palo Alto, CA (US); Carol Green, Portola Valley, CA (US); Hui Zhang, Sunnyvale, CA (US); Jian Luo, Palo Alto, CA (US)

( * ) Notice: Subject to any disclaimer, the term of this patent is extended or adjusted under 35 U.S.C. 154(b) by 0 days.

(21) Appl. No.: 14/776,313

(22) PCT Filed: Mar. 14, 2014

(86) PCT No.: PCT/US2014/028060
§ 371 (c)(1),
(2) Date: Sep. 14, 2015

(87) PCT Pub. No.: WO2014/152869
PCT Pub. Date: Sep. 25, 2014

(65) Prior Publication Data
US 2016/0039756 A1   Feb. 11, 2016

Related U.S. Application Data

(60) Provisional application No. 61/783,733, filed on Mar. 14, 2013, provisional application No. 61/783,528, filed on Mar. 14, 2013, provisional application No. 61/783,305, filed on Mar. 14, 2013.

(51) Int. Cl.
*C07D 211/26* (2006.01)
*A61K 31/4465* (2006.01)
*A61K 31/452* (2006.01)

(52) U.S. Cl.
CPC ........ *C07D 211/26* (2013.01); *A61K 31/4465* (2013.01); *A61K 31/452* (2013.01)

(58) Field of Classification Search
None
See application file for complete search history.

(56) References Cited

U.S. PATENT DOCUMENTS 5,849,732 A * 12/1998 Suzuki .................. C07C 275/34
514/217.11
8,076,332 B2 * 12/2011 Mogi .................... C07C 275/24
514/237.2

* cited by examiner

*Primary Examiner* — David K O'Dell
(74) *Attorney, Agent, or Firm* — Thomas | Horstemeyer, LLP

(57) ABSTRACT

Compositions and methods for treatment and prevention of disorders and conditions characterized by reduced TGF-B signaling are described. In particular, the compositions and methods are useful for reducing or eliminating the pathologies associated with Alzheimer's disease. The compositions include urea derivatives containing a piperidine, piperidinium, or a piperidin-4-yl methyl; cycloalkyl, aryl, and fluorobenzyl moieties.

5 Claims, 29 Drawing Sheets

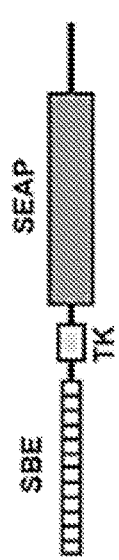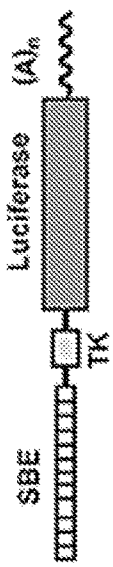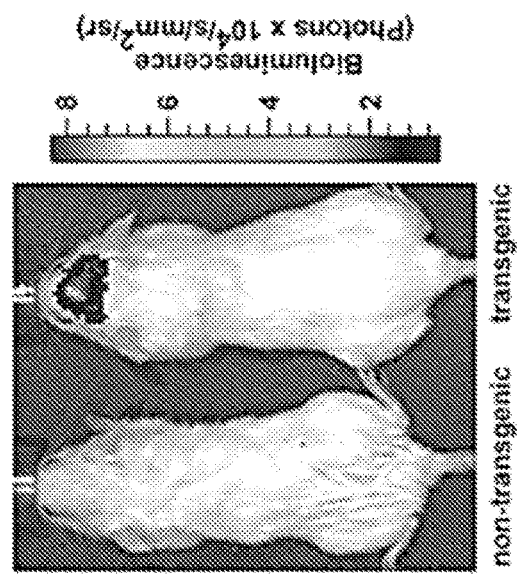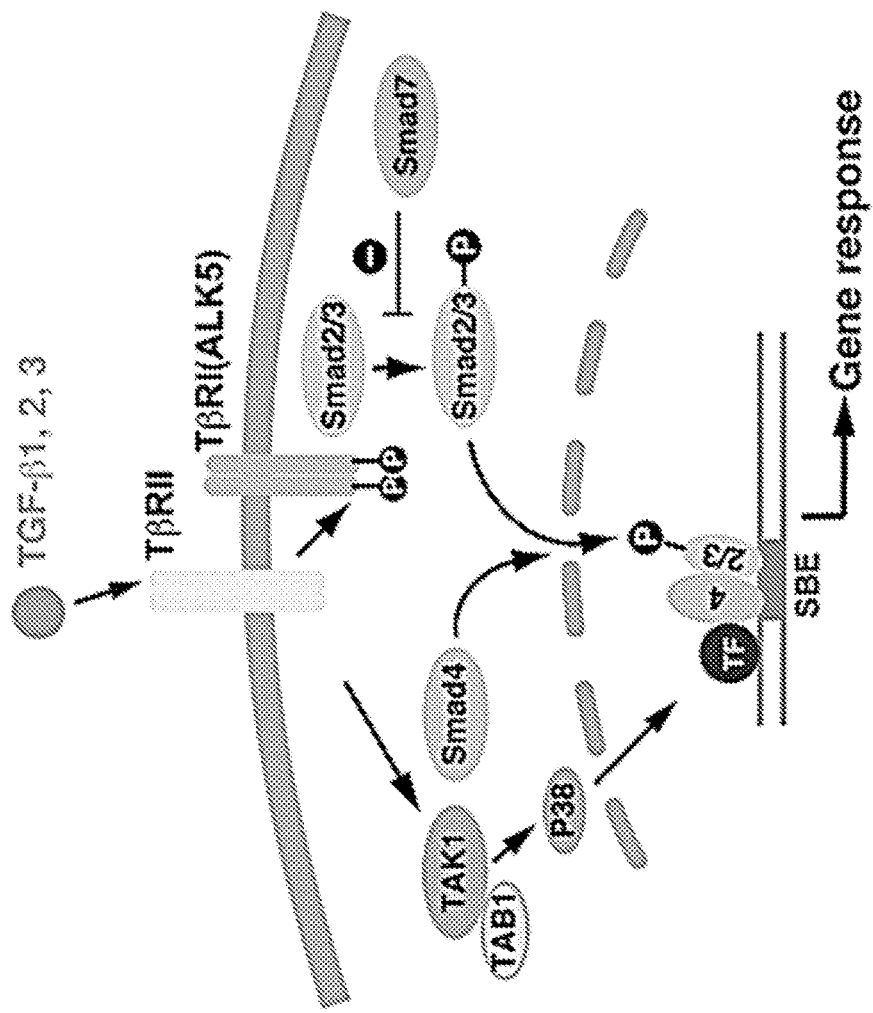
Fig. 1A  Fig. 1B  Fig. 1C

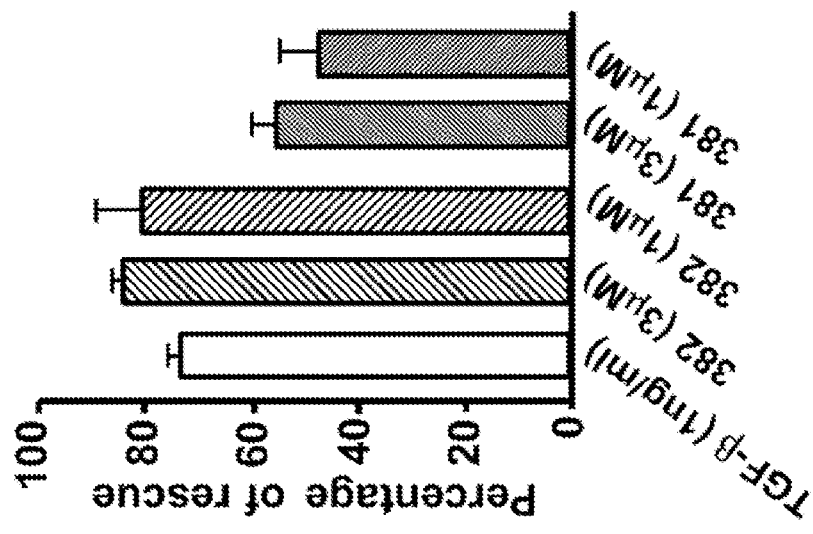
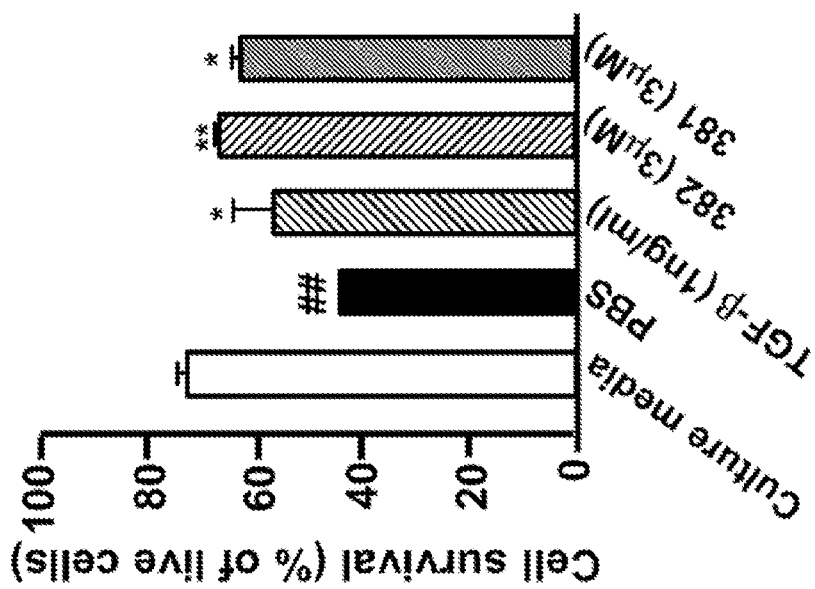
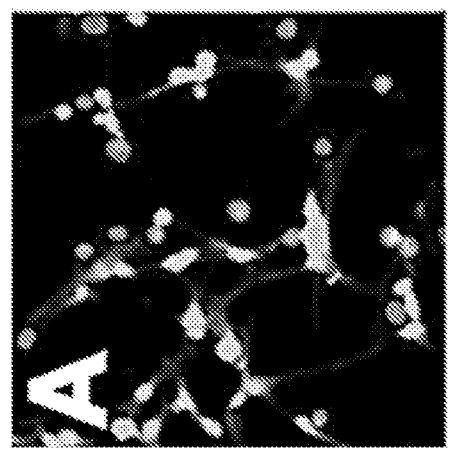

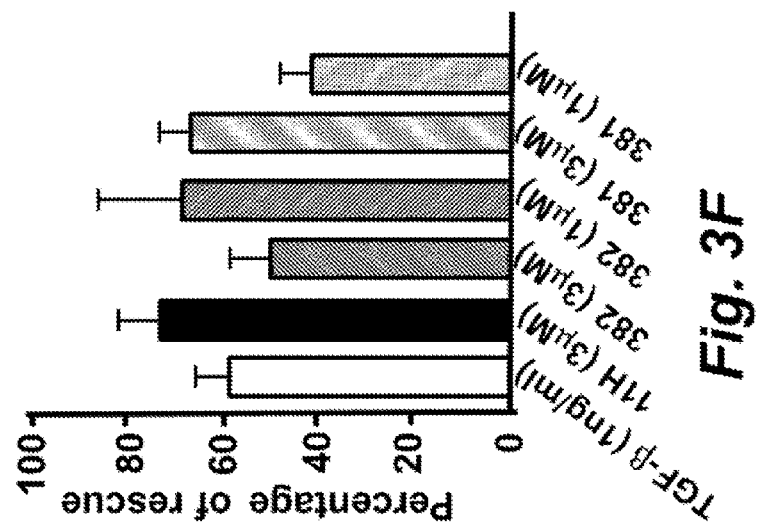
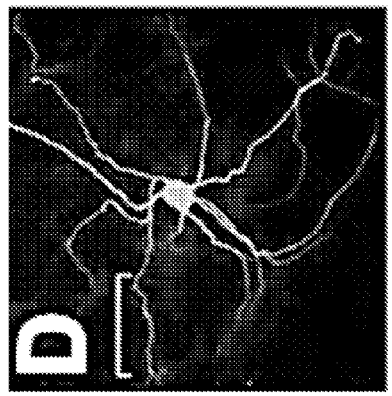
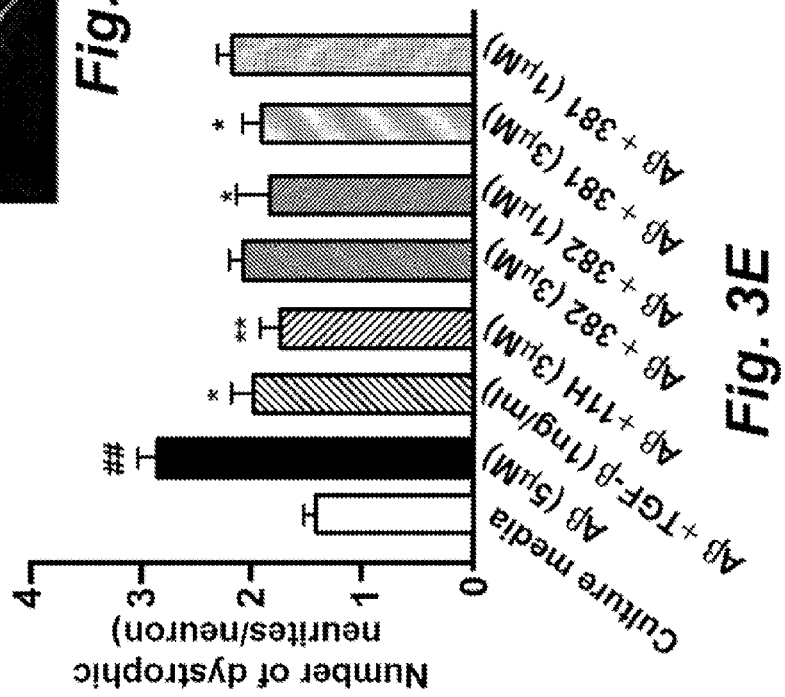

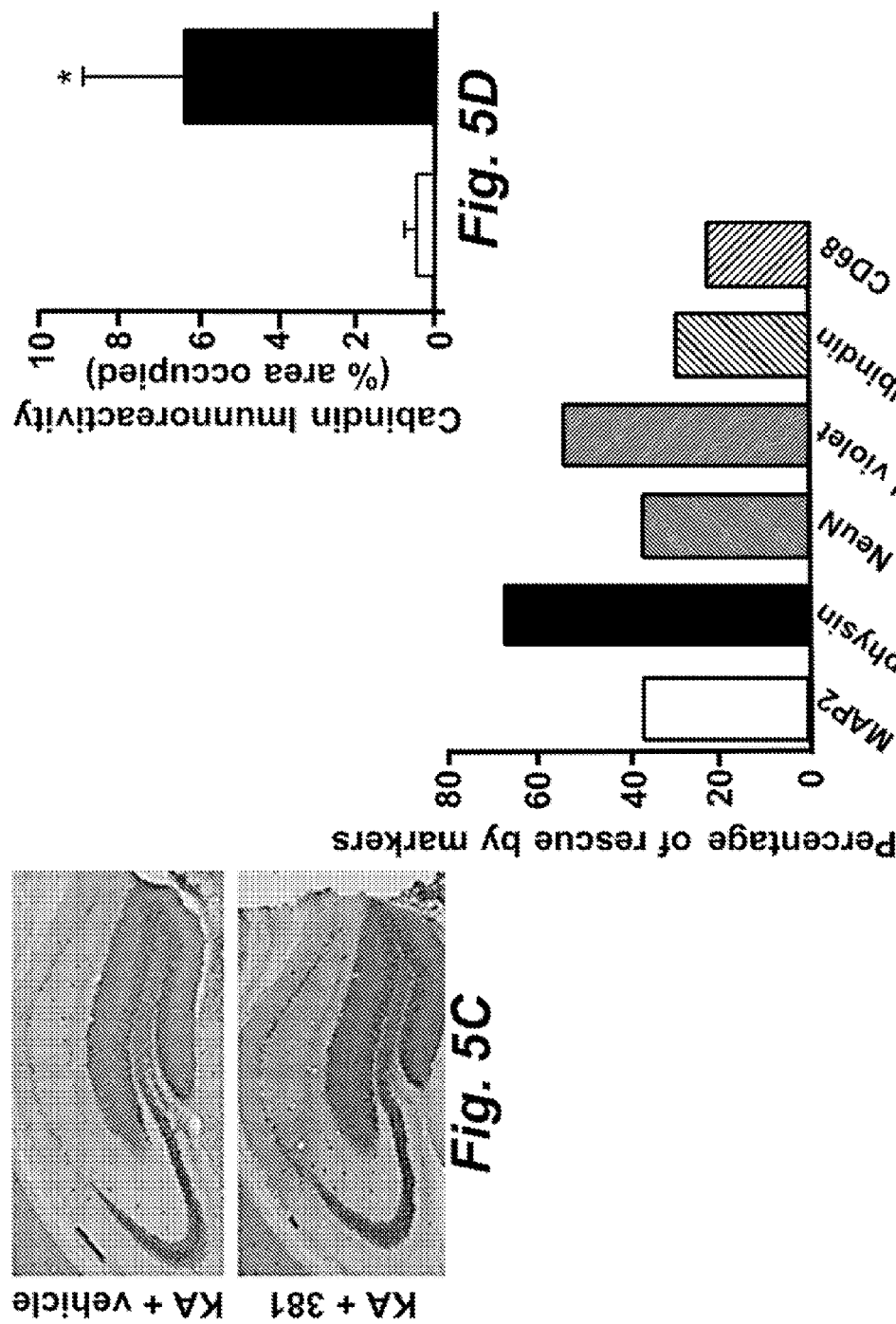

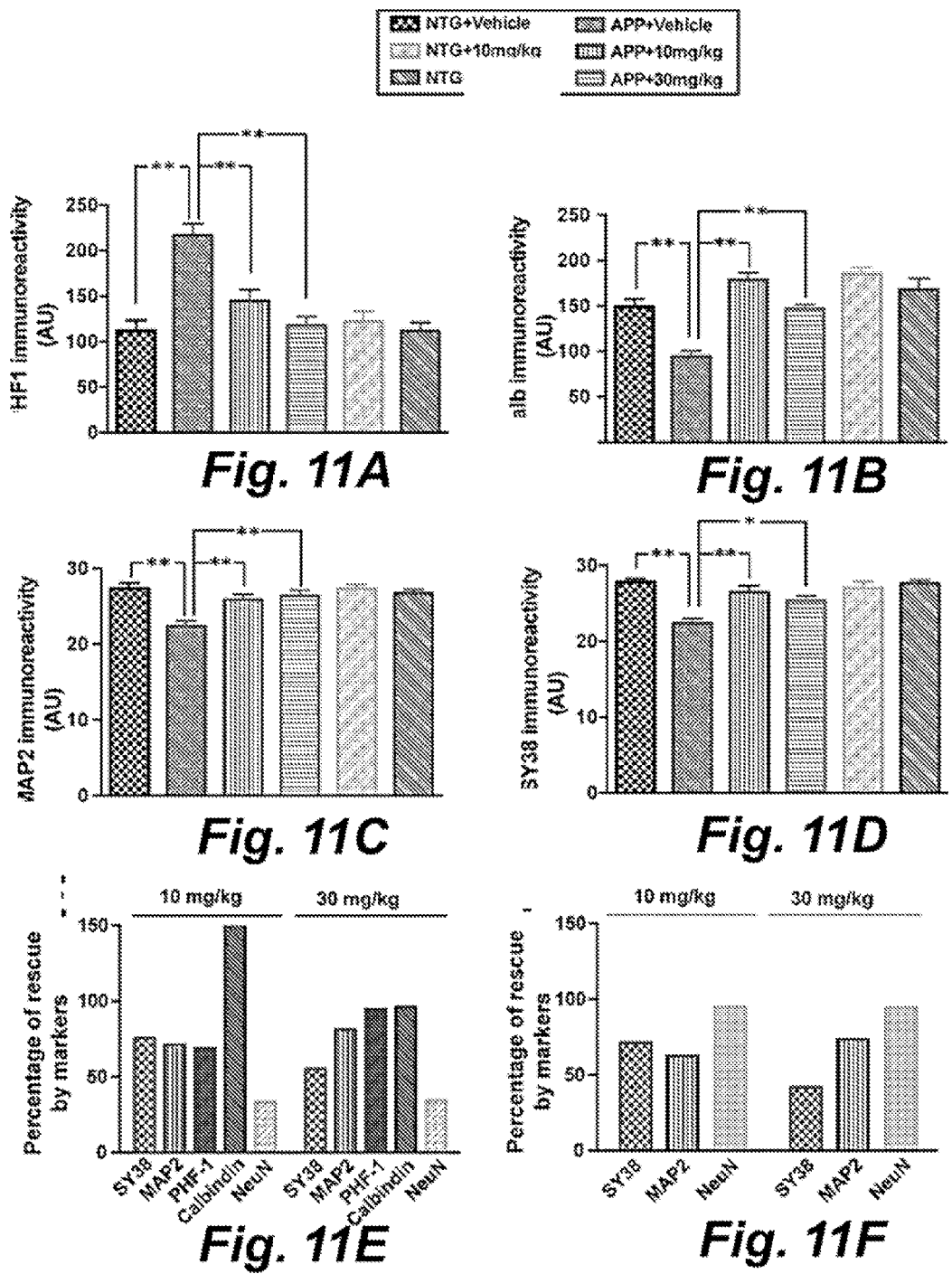

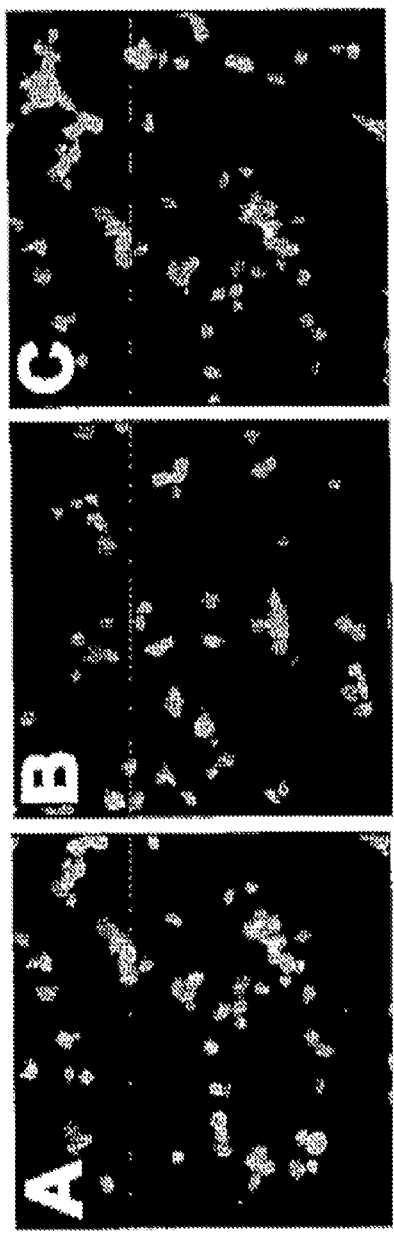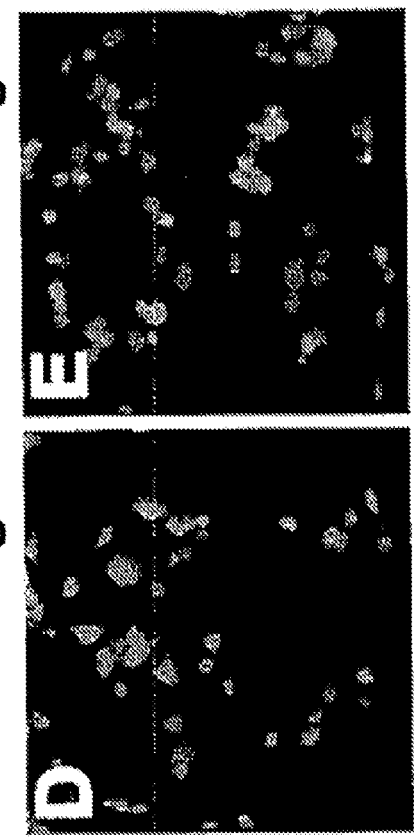

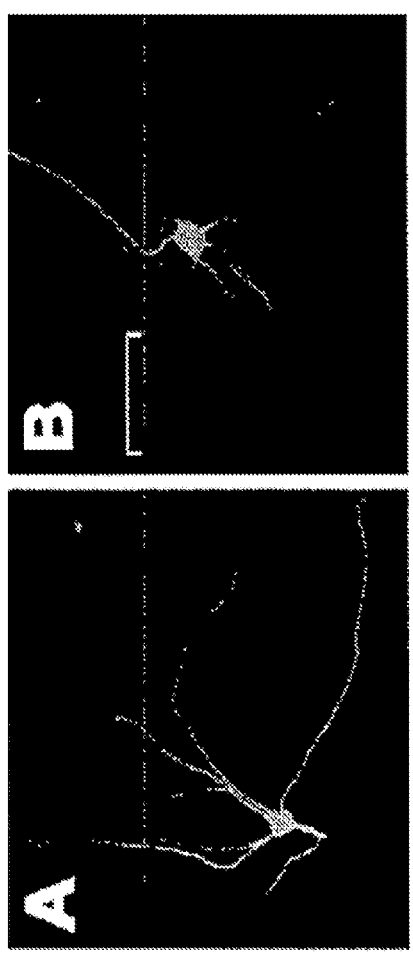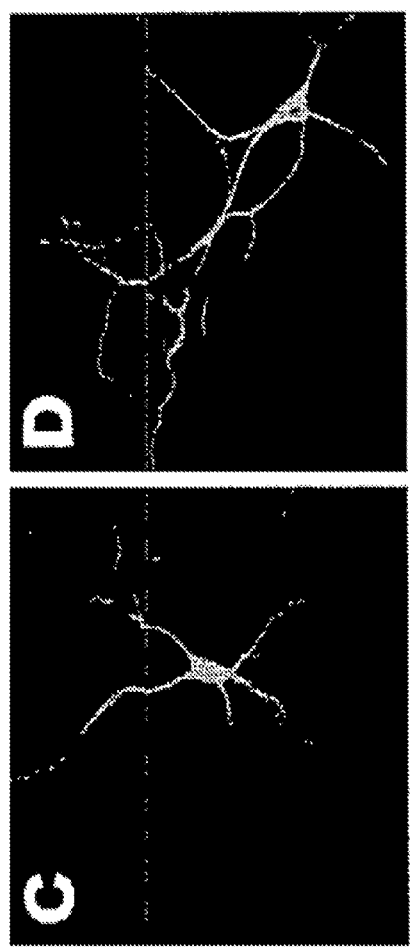

BENZYL UREA DERIVATIVES FOR ACTIVATING TGF-BETA SIGNALING

CROSS-REFERENCE TO RELATED APPLICATION

This application is the 35 U.S.C. §371 national stage application of PCT Application No. PCT/US2014/028060, filed Mar. 14, 2014, which claims priority from U.S. Provisional Application No. 61/783,305, entitled "BENZYL UREA DERIVATIVES FOR ACTIVATING TGF-BETA SIGNALING" filed on Mar. 14, 2013, U.S. Provisional Application No. 61/783,528, entitled "BENZYL UREA DERIVATIVES FOR ACTIVATING TGF-BETA SIGNALING" filed on Mar. 14, 2013, and to U.S. Provisional Application No. 61/783,733, entitled "BENZYL UREA DERIVATIVES FOR ACTIVATING TGF-BETA SIGNALING" filed on Mar. 14, 2013, the entireties of which are herein incorporated by reference.

STATEMENT REGARDING GOVERNMENT INTERESTS

This invention was made with Government support under contract NS057496 awarded by the National Institutes of Health. The Government has certain rights in the invention.

TECHNICAL FIELD

The present disclosure relates to small-molecule compositions and methods for treatment and prevention of diseases and conditions associated with reduced TGF-β signaling, or conditions where increased TGF-β signaling is advantageous, including neurological disorders.

BACKGROUND

Alzheimer's disease (AD) is a common and devastating neurodegenerative disorder for which no cure exists. Currently available drugs approved by the U.S. FDA typically afford only modest symptomatic benefits. Progressive dementia often results in complete incapacitation, profound impairment in quality of life, enormous burdens on family caregivers and society, and, ultimately, death from one of a variety of complications of the disease.

In the United States alone there are over five million people with AD, a figure that is expected to rise to about 16 million by 2050, with attendant costs exceeding $1.1 trillion dollars. AD is the most frequent reason for nursing home placement and the sixth most common cause of death in the United States. Recent failures of development programs evaluating disease modifying therapies for AD (e.g., solanezumab, an anti-Aβ monoclonal antibody) bring the unmet need for improved therapies into heightened relief.

AD usually presents initially with memory loss, which may be subtle at the onset. Progressive dementia then follows, accompanied by the advent of other cognitive deficits in language (e.g., word-finding difficulties), executive function, and visuospatial recognition. The ability to perform activities of daily living is gradually compromised. Alterations in behavior and personality may take the form of mood fluctuations, apathy, aggression, and loss of inhibition with socially inappropriate behavior. Patients may harbor delusions and experience hallucinations. Ultimately, any semblance of autonomy is completely abolished as patients become bedridden, incontinent, and incapable of feeding, bathing, or dressing themselves. Although the course is variable, AD generally progresses over a period of about a decade. Death commonly results from aspiration pneumonia, inanition, or pulmonary emboli.

The vast majority of AD cases are seen in the elderly, but about 200,000 individuals in the United States younger than 65 years of age are estimated to have the disease. A variety of genetic factors significantly influence susceptibility to disease, most importantly the APOE ε4 allele which, it has been hypothesized, may be associated with impaired clearance of amyloid, which is believed to have a critical role in disease pathogenesis. Aβ42 is thought to represent the toxic and amyloidgenic cleavage product of amyloid precursor protein.

Pathologically, neurodegeneration is prominent in various regions of the temporal lobe, including the entorhinal cortex, hippocampus, and lateral cortex. As the disease becomes more severe, more generalized involvement results in brain shrinkage and ventricular enlargement. Histopathological hallmarks of the disease include neuritic plaques and neurofibrillary tangles. Plaques consist of a dense core containing polymerized amyloid, several other proteins, and proteoglycan, surrounded by dystrophic tau-immunoreactive neurites and activated microglial cells. Neurofibrillary tangles contain abnormally hyperphosphorylated tau protein that can no longer stabilize or interact appropriately with microtubules, or subcellular components that undergird neuronal architecture and that mediate axonal transport of neurotransmitters and ion channels. Impaired cholinergic transmission in AD may be related to degeneration of cholinergic neurons in the nucleus basalis of Meynert that broadly project to the cortex.

All currently approved treatments for AD are associated with only modest benefit. Mean response as measured by ADAS-Cog is approximately 2.7 points for the cholinesterase inhibitors. They may delay, decline, or produce some evidence of improvement in cognition and ability to perform activities of daily living, but treatment has not been shown to permanently halt progression or clearly modify the disease itself.

To a large measure, treatment of patients with AD is supportive, and this entails what often amounts to enormous efforts on the part of family caregivers in the home. The provision of emotional support and supervision, the overseeing of guided activities meant to sustain quality of life and minimize frustration, and assistance, ultimately, with the most basic elements of daily life such as feeding, clothing, and bathing, frequently results in caregiver burnout and nursing home placement as the disease advances toward the terminal stages. The human and economic toll of AD demands improvements in the standard of medical care.

TGF-β1 has been demonstrated to protect neurons against various toxins and injurious agents in cell culture and in vivo. Astroglial over-expression of TGF-β1 in transgenic mice protected against neurodegeneration induced with acute neurotoxin kainic acid or associated with chronic lack of apolipoprotein E expression (Brionne et al., (2003) *Neuron* 40: 1133-1145). It has been demonstrated that TGF-β1 protects neurons from excitotoxic death (Boche et al., (2003) *J. Cereb. Blood Flow Metab.* 23: 1174-1182).

Several mechanisms have been postulated to explain how TGF-β1 protects neurons. For example, TGF-β1 decreases Bad, a pro-apoptotic member of the Bcl-2 family, and contributes to the phosphorylation and inactivation, of Bad by activation of the Erk/MAP kinase pathway. TGF-β1, however, also increases production of the anti-apoptotic protein Bcl-2. TGF-β1 has also been shown to synergize with neurotrophins and/or be necessary for at least some of the effects of a number of important growth factors for neurons, including neurotrophins, fibroblast growth factor-2, and glial cell-line derived neurotrophic factor (Unsicker & Krieglstein (2002) *Adv. Exp Med. Biol.* 513: 353-74; Unsicker & Krieglstein (2000) *Cytokine Growth Factor Rev.* 11: 97-102). In addition, TGF-β1 increases laminin expression and is necessary for normal laminin protein levels in the brain. It is also possible that TGF-β1 decreases inflammation in the infarction area, attenuating secondary neuronal damage.

TGF-β1 transgenic mice over-expressing a secreted, constitutively-active form of TGF-β1 in astrocytes at modest levels develop age-related cerebrovascular abnormalities including thickening of the capillary basement membrane and cerebrovascular amyloid deposition. Nevertheless, these mice have better cognitive function than non-transgenic controls. Similar microvascular abnormalities are typical for AD and consistent with the observation that TGF-β1 mRNA levels in brains of AD cases correlate positively with vascular amyloid deposition.

TGF-β1 transgenic mice cross-bred with human amyloid precursor (hAPP) transgenic mice, develop synaptic degeneration and amyloid plaques in the brain parenchyma. Unexpectedly, a prominent reduction in plaque formation and overall Aβ accumulation was found in hAPP/TGF-β1 double transgenic compared with hAPP mice. Most of the remaining amyloid accumulated around cerebral blood vessels.

Increased levels of TGF-β1 reduced the number of plaques in human amyloid precursor protein (hAPP) mice by 75% and overall Aβ levels by 60%, compared to mice with normal levels of TGF-β1. Interestingly, TGF-β1 stimulated microglial cells to degrade synthetic Aβ peptide in culture. Because TGF-β1 also caused an activation of microglia in hAPP/TGF-β1 mice, these data suggest that at least some of the effects of TGF-β1 involve the activation of microglial phagocytosis. The need remains for more effective pharmaceutical compounds for treating and preventing stroke, heart disease, bone loss, cancer, multiple sclerosis, wound healing, inflammation, and neurodegenerative disorders, especially, but not limited to, Alzheimer's disease.

SUMMARY

The present disclosure provides derivatives of a compound that acts as an agonist of TGF-β signaling in cell. The compounds are especially useful, and may be effectively formulated in pharmaceutically acceptable compositions, for delivery to a mammalian subject to remedy a pathological condition resulting from or causing a deficiency in TGF-β signaling. Such deficiencies may be manifested by such as a neuropathological syndrome such as Alzheimer's disease.

Accordingly, one aspect of the disclosure encompasses embodiments of a TGF-β signaling agonist having the formula I:

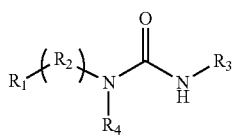

wherein $R_1$ group is a substituted phenyl; $R_2$ can be —$CH_2$— group or —CH=CH($CH_2$)—; $R_3$ can be selected from the group consisting of: a substituted or non-substituted $C_5$ or $C_6$ cycloalkyl, and a substituted or non-substituted phenyl, and $R_4$ can be —$CH_2$—N-piperidine or N-piperidine, or a pharmaceutically acceptable salt thereof.

In some embodiments of this aspect of the disclosure, $R_1$ can be a phenyl group or a phenyl substituted with at least one halogen.

In some embodiments of this aspect of the disclosure, $R_1$ can be a phenyl substituted with at least one fluorine.

Another aspect of the disclosure encompasses embodiments of a pharmaceutically acceptable composition comprising a TGF-β signaling agonist having the formula I:

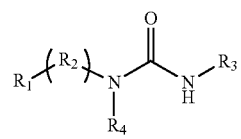

wherein $R_1$ group is a substituted phenyl; $R_2$ can be —$CH_2$— group or —CH=CH($CH_2$)—; $R_3$ can be selected from the group consisting of: a substituted or non-substituted $C_5$ or $C_6$ cycloalkyl, and a substituted or non-substituted phenyl, and $R_4$ can be —$CH_2$—N-piperidine or N-piperidine, or a pharmaceutically acceptable salt thereof, and a pharmaceutically acceptable carrier.

In some embodiments of this aspect of the disclosure, the pharmaceutically acceptable composition can be formulated to deliver an effective amount of the TGF-β agonist to a mammalian subject.

In some embodiments of this aspect of the disclosure, the pharmaceutically acceptable composition can be formulated for administration to a recipient mammalian subject by oral, intraperitoneal, intravenous, or intramuscular administration.

Still another aspect of the disclosure encompasses embodiments of a method of increasing TGF-β signaling activity of a cell, comprising the step of contacting the cell with an effective dose of a TGF-β signaling agonist having the formula I:

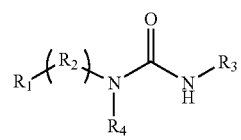

wherein $R_1$ group is a substituted phenyl; $R_2$ can be —$CH_2$— group or —CH=CH($CH_2$)—; $R_3$ can be selected from the group consisting of: a substituted or non-substituted $C_5$ or $C_6$ cycloalkyl, and a substituted or non-substituted phenyl, and $R_4$ can be —$CH_2$—N-piperidine or N-piperidine, or a pharmaceutically acceptable salt thereof, and a pharmaceutically acceptable carrier.

In some embodiments of this aspect of the disclosure, the effective dose of the TGF-β signaling agonist can be combined with a pharmaceutically acceptable carrier in a pharmaceutically acceptable composition formulated for delivery of the agonist to a cell or population of cells of a mammalian subject.

In some embodiments of this aspect of the disclosure, the method can further comprise the step of administering the pharmaceutically acceptable composition to a mammalian subject.

In some embodiments of this aspect of the disclosure, the increased TGF-β signaling activity can be in a cell of the brain of the recipient subject.

In some embodiments of this aspect of the disclosure, the mammalian subject can have a disease or condition characterized by reduced TGF-β signaling activity, and wherein an increase in TGF-β signaling activity can be advantageous to the mammalian subject. In some embodiments of this aspect of the disclosure, increasing TGF-β signaling activity can provide at least one of an enhancement of neuroprotection, an enhancement of cognitive behavior, and a reduction of neurodegeneration in the brain of the mammalian subject.

In some embodiments of this aspect of the disclosure, the disease or condition can be Alzheimer's disease.

Yet another aspect of the disclosure encompasses embodiments of a method of increasing TGF-β signaling activity in the brain of a subject with Alzheimer's disease, the method comprising the step of: administering to a subject with Alzheimer's disease, or suspected of having Alzheimer's disease, a pharmaceutically acceptable composition comprising; (a) an effective dose of a TGF-β signaling agonist having the formula I:

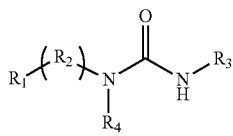

wherein $R_1$ group is a substituted phenyl; $R_2$ can be —$CH_2$— group or —$CH=CH(CH_2)$—; $R_3$ can be selected from the group consisting of: a substituted or non-substituted $C_5$ or $C_6$ cycloalkyl, and a substituted or non-substituted phenyl, and $R_4$ can be —$CH_2$—N-piperidine or N-piperidine, or a pharmaceutically acceptable salt thereof; and (b) a pharmaceutically acceptable carrier; and wherein: (1) an increase in TGF-β signaling activity is advantageous to the subject; and (2) the TGF-β signaling agonist is effective to reduce at least one of the number of amyloid plaques in the brain and the accumulation of Aβ in the brain.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A schematically illustrates TGF-β signaling pathways known in the art.

FIG. 1B schematically illustrates the SBE-SEAP reporter gene reporter nucleic acid construct.

FIG. 1C illustrates digital images of the activation of the SBE-luc reporter gene promoter by TGF-β signaling driving the expression of luciferase in SBE-luc reporter mice.

FIGS. 3A-3H illustrate that compound SRI-011381 (381) protects cultured neurons form Aβ toxicity.

FIG. 3A shows a digital image illustrating live cells (lightest images) and the nuclei of dead cells (darker greytone images).

FIG. 3B is a graph showing cell survival expressed as the percentage of live cells over total number of the cells. Compound SRI-011381 (381) provides better protection than TGF-β1, as shown by the percentage of live cells.

FIG. 3C is a graph showing cell survival expressed as the percentage of live cells over total number of the cells. Compound SRI-011381 (381) provides better protection than TGF-β1, as shown by the percentage of rescue.

FIG. 3D is a digital image showing that hippocampal neurons (21-22 DIV) exposed to 5 μM Aβ for 48 h (fixed and stained for MAP-2) led to increased tortuosity, exhibiting multiple abrupt turns (brackets).

FIG. 3E is a graph illustrating that the average numbers of dystrophic neurites per neuron (n=10-12 fields/well) were markedly reduced by compound 381, as well as by TGF-β and 11H.

FIG. 3F is a graph illustrating that compound 381 provides similar rescue as TGF-β1.

FIG. 3G is a graph illustrating hippocampal neurons (21-22 DIV) exposed to 5 μM Aβ for 72 h and assessed for cytotoxicity.

FIG. 3H shows that compound 381 provides similar or better rescue than TGF-β1 at the concentrations tested.

FIGS. 5A-5E illustrate that SRI-011381 (381) protects mice against kainic acid-induced excitotoxicity and neurodegeneration.

FIGS. 5A and 5B show GFAP-luc mice (2-month-old) lesioned with kainic acid (20 mg/kg).

FIG. 5A shows representative images showing increased bioluminescence signals over the brain after kainic acid injury (left panel) and the reduction by SRI-011381 (381) treatment (right panel).

FIG. 5B is a graph showing bioluminescence expressed as fold induction over baseline measured 1 day before kainic acid administration for each mouse.

FIGS. 5C and 5D illustrate brain calbindin immunostaining.

FIG. 5E is a graph showing the percentage of rescue, i.e. systemic administration of 381 reduces neurodegeneration by 6 markers.

FIG. 9A shows the results of cognitive function assessed using a Y-maze after 10 weeks of treatment.

FIGS. 9B-9D show the results of the fear conditioning tests.

FIGS. 11A-11F illustrate that compound SRI-011381 (381) reduces neurodegeneration in APP751$^{Lon,Swe}$ transgenic mice.

FIG. 11A shows the results after brain sections were stained for PHF1.

FIG. 11B shows the results after brain sections were stained for calbindin.

FIG. 11C shows the results after brain sections were stained for Map2.

FIG. 11D shows the results after brain sections were stained for synaptophysin.

FIG. 11E shows the percentage of rescue calculated for each marker from the hippocampus.

FIG. 11F shows the percentage of rescue calculated for each marker from the cortex.

FIGS. 12A-12G illustrate that compounds 382, 956, and TGF-β inhibit Aβ-induced cell death in B103 cells. B103 neuroblastoma cells were incubated with Aβ for 24 h. The compounds and TGF-β were added 2 h before Aβ. Following incubations, live and dead cells were assessed with calcein-acetoxymethylester (CAM) and SYTOX® Orange (Invitrogen), respectively. Under a fluorescence microscope, the live cells showed green color (shown as darker shading in FIGS. 12A-12E) and the nuclei of dead cells exhibited orange fluorescence (shown in lighter shading). Representative images showing increased cell death after Aβ exposure (5 μM, FIG. 12B) compared with control media (FIG. 12A), and the reduction by the treatment of TGF-β (FIG. 12C), compounds 382 (FIG. 12D) and 956 (FIG. 12E).

FIG. 12F is a graph illustrating cell survival was expressed as the percentage of live cells over total number of the cells. At 3 μM, compounds 382 and 956 both provide better protection than TGF-β (1 ng/ml).

FIG. 12G is a graph illustrating cell survival was expressed as the percentage of live cells over total number of the cells. At a lower concentration (1 μM), compound 382 provides similar protection against 2 μM Aβ, and slightly lower protection against 5 μM Aβ. ##, $P<0.01$ vs culture media; *, $P<0.05$; **, $P<0.01$ vs Aβ+PBS; ANOVA, Tukey's post-hoc test.

FIGS. 13A-13F illustrate that compounds 382 and 956 prevent Aβ-induced neurite dystrophy. Hippocampal neurons (21-22 DIV) were exposed to culture medium (FIG. 13A), 5 μM Aβ (FIG. 13B); 5 mM Aβ+3 μM compound 382 (FIG. 13C), or 5 μM Aβ+3 mM compound 956 (FIG. 13D). After 48 h, cultures were fixed and immunostained for MAP-2 to visualize dendrites. Aβ exposure significantly increased tortuosity, exhibiting multiple abrupt turns (bracketed in FIG. 13B), and was markedly reduced with compounds 382 and 956 (FIGS. 13C and 13D).

FIG. 13E is a graph illustrating the average numbers of dystrophic neurites per neuron (n=10-12 fields/well). Dystrophic neurites were defined as neurites exhibiting multiple abrupt turns (tortuosity). Dystrophic neurite counting was measured by blinded observers. #, $P<0.05$, ##, $P<0.01$ vs culture media; $P<0.05$, **, $P<0.01$ vs Aβ+PBS; ANOVA, Tukey's post-hoc test.

FIG. 13F is a graph illustrating a mean differential curvature analysis in randomly selected fields and demonstrated that Aβ induced a significant increase in neurite curvature that was prevented by TGF-β, 11H (HCl salt), and compounds 382 and 956 (n=5 fields/well). Curvature analysis was measured by blinded observers. #, $P<0.05$, ##, $P<0.01$ vs culture media; •, $P<0.05$, **, $P<0.01$ vs Aβ+PBS; ANOVA, Tukey's post-hoc test.

Figure 2A:
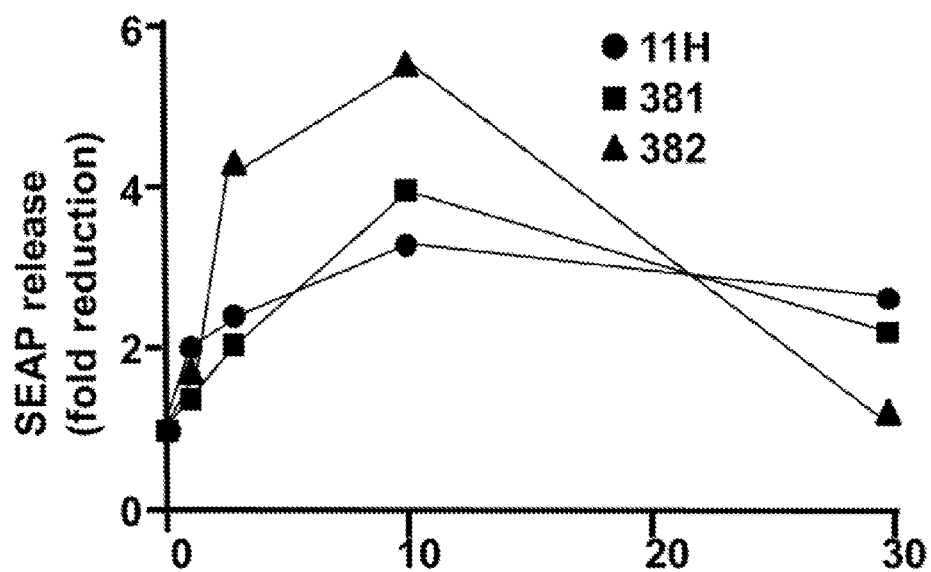
FIG. 2A shows a dose-response of compound 11H and its analog SRI-011381 (381) in the F11 SBE-SEAP reporter cell line.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the advantageous methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

AD, Alzheimer's disease; TGF, Transforming Growth Factor; ADMET, Absorption, Distribution, Metabolism, and Excretion assay; CNS, central nervous system; ip., intraperitoneal; iv., intravenous; im., intramuscular; po, oral gavage; s.q., subcutaneous; MTD, Maximum Tolerated Dose; NOAEL, No observed adverse effect level.

Definitions

In describing and claiming the disclosed subject matter, the following terminology will be used in accordance with the definitions set forth below.

The terms "administration of" and "administering" a compound or composition as used herein refers to providing a compound or compositions of the disclosure or a prodrug of a compound of the disclosure to the individual in need of treatment. The compounds of the present disclosure may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The term "amyloidosis" as used herein refers to the accumulation of amyloid plaques and/or Aβ in the brain. Such diseases/disorders include localized amyloidosis as well as systemic amyloidosis. It can appear without other pathology or can accompany plasma cell dyscrasia or multiple myeloma. Amyloidosis is also associated with chronic infection or chronic inflammation. Familial forms of amyloidosis include familial Mediterranean fever (FMF), familial British dementia (FBD), and familial amyloid polyneuropathy (FAP). Another form of amyloidosis is found in long-term hemodialysis patients. Creutzfeldt-Jakob disease, motor neuron diseases, polyglutamine disorders (including Huntington's disease), progressive frontotemporal dementia (FTD), Lewy Body dementia (LB), progressive supranuclear Palsy (PSP), Pick's disease, and Parkinson's disease can also be associated with amyloid plaques and/or accumulation of Aβ in the brain. Amyloidosis is also associated with the neurodegenerative pathology of Alzheimer's disease.

The term "co-crystal" as used herein means a crystalline material comprised of two or more unique solids at room temperature, each containing distinctive physical characteristics, such as structure, melting point, and heats of fusion. Co-crystals can be formed by an active pharmaceutical ingredient (API) and a co-crystal former either by hydrogen bonding or other non-covalent interactions, such as pi stacking and van der Waals interactions. An aspect of the disclosure provides for a co-crystal wherein the co-crystal former is a second API. In another aspect, the co-crystal former is not an API. In another aspect, the co-crystal comprises more than one co-crystal former. For example, two, three, four, five, or more co-crystal formers can be incorporated in a co-crystal with an API. Pharmaceutically acceptable co-crystals, are described, for example, in "Pharmaceutical co-crystals," Journal of Pharmaceutical Sciences, Volume 95 (3) Pages 499-516, 2006.

A co-crystal former which is generally a pharmaceutically acceptable compound, may be, for example, benzoquinone, terephthalaldehyde, saccharin, nicotinamide, acetic acid, formic acid, butyric acid, trimesic acid, 5-nitroisophthalic acid, adamantane-1,3,5,7-tetracarboxylic acid, formamide, succinic acid, fumaric acid, tartaric acid, oxalic acid, tartaric acid, malonic acid, benzamide, mandelic acid, glycolic acid, fumaric acid, maleic acid, urea, nicotinic acid, piperazine, p-phthalaldehyde, 2,6-pyridinecarboxylic acid, 5-nitroisophthalic acid, citric acid, and the alkane- and arenesulfonic acids such as methanesulfonic acid and benzenesulfonic acid. In general, all physical forms of compounds of the disclosure, including co-crystals, are intended to be within the scope of the present disclosure.

The terms "effective dose," "therapeutically effective amount," and "dose" as used herein refer to the amount of a composition comprising a compound or composition of the present disclosure, and which is effective for producing a desired therapeutic effect, biological or medicinal response in a tissue system, animal or human that is being sought by a researcher, veterinarian, medical doctor or other clinician, which includes alleviation of the symptoms of the disease or disorder being treated or a reduction in a side-effect due to an administered pharmaceutical agent. It is further contemplated that an effective dose may be delivered to a recipient subject in a single bolus administrative action or by the totality of a plurality of consecutive or periodic administrative steps.

The term "solvate" as used herein refers to a physical association of a compound with one or more solvent molecules or a complex of variable stoichiometry formed by a solute (for example, a compound of the disclosure) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological, activity of the solute. Solvates encompass both solution-phase and isolatable solvates. Representative solvates include hydrates, ethanolates, methanolates, and the like. Dehydrate, co-crystals, anhydrous, or amorphous forms of the compounds of the disclosure are also included. The term "hydrate" means a solvate wherein the solvent molecule(s) is/are $H_2O$, including, mono-, di-, and various poly-hydrates thereof. Solvates can be formed using various methods known in the art.

The amount of solvent used to make solvates can be determined by routine testing. For example, a monohydrate of a compound of the disclosure would have about 1 equivalent of solvent ($H_2O$) for each equivalent of a compound of the disclosure. However, more or less solvent may be used depending on the choice of solvate desired.

The term "TGF-β" as used herein refers to Transforming Growth Factor-β (TGF-β), a member of a superfamily of conserved cytokines, growth factors, and morphogens that play key functions in development and homeostasis. TGF-β signaling is implicated in a numerous diseases and conditions, including stroke, heart disease, bone loss, cancer, multiple sclerosis, wound healing, inflammation, and neurodegenerative disorders. The TGF-β subfamily includes three isoforms in mammals, TGF-β1, -β2, and -β3, that promote cell survival, induce apoptosis, stimulate cell proliferation, induce differentiation, and/or initiate or resolve inflammation, depending on the particular cell type and environment. Accurate regulation of TGF-β bioactivity and signaling is key to controlling these functions and essential to health and normal aging. The disruption of TGF-β signaling molecules frequently results in embryonic lethality in mice.

The biological actions of TGF-βs are mediated by a receptor complex consisting of the TGF-β type 1 (TBR1/ALK5) and type 2 (TBR2) serine/threonine kinase receptor subunits, as schematically illustrated in FIG. 1A. Receptor activation leads to phosphorylation of Smad proteins, which translocate to the nucleus where they bind to the Smad DNA-binding element (SBE) present in an estimated 400 genes. TGF-βs can also activate other signaling pathways including the p38 MAP kinase pathway and the JNK or NF-kB pathways. Despite interaction with other pathways, knockout studies in mice suggest that Smad proteins are the key mediators of many of TGF-β1's actions in vivo.

TGF-β is known to play a role in neurological diseases and condition. In the normal central nervous system (CNS), TGF-β1, -β2, and -β3, and their respective receptors are expressed in neurons, astrocytes, and microglia. The best-studied isoform, TGF-β1, is expressed in the adult CNS predominantly in response to CNS injury, and may function as an organizer of protective and regenerative responses. It is upregulated in glial cells in response to brain lesioning, transient forebrain ischemia, and stroke. TGF-β2 and TGF-β3 bind to the same receptors as TGF-β1 but have different patterns of activation and expression. Immunoreactivity to TGF-β2 and TGF-β3 is detected in astrocytes and neurons in the normal CNS and is increased in neurodegenerative diseases or after stroke. Changes in TGF-β expression are reported in the AD brain, cerebrospinal fluid (CSF), and serum. TGF-β1 immunoreactivity is increased in (or near) amyloid plaques and around cerebral blood vessels.

The terms "treat" or "treatment" as used herein refer to both therapeutic treatment and prophylactic or preventative measures, where the object is to prevent or slow down (lessen) an undesired physiological change or disorder. Beneficial or desired clinical results include, but are not limited to, alleviation of symptoms, diminishment of the extent of disease, stabilized (i.e., not worsening) state of disease, and delay or slowing of progression of the symptoms recognized as originating from a stroke. The term "treatment" can also refer to prolonging survival as compared to expected survival if not receiving treatment. Those in need of treatment include those already with the condition or disorder as well as those prone to have the condition or disorder or those in which the condition or disorder is to be prevented or onset delayed.

The term "alkyl" as used herein refers to $C_{1-20}$ inclusive, linear (i.e., "straight-chain"), branched, or cyclic, saturated or at least partially and, in some cases, fully unsaturated (i.e., alkenyl and alkynyl) hydrocarbon chains including, for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

The term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

In aspects of the disclosure, "substituted alkyl" includes an alkyl group substituted by, for example, one to five substituents, and preferably 1 to 3 substituents, such as alkyl, alkoxy, oxo, alkanoyl, aryl, aralkyl, aryloxy, alkanoyloxy, cycloalkyl, acyl, amino, hydroxyamino, alkylamino, arylamino, alkoxyamino, aralkylamino, cyano, halogen, hydroxyl, carboxyl, carbamyl, carboxylalkyl, keto, thioketo, thiol, alkylthiol, arylthio, aralkylthio, sulfonamide, thioalkoxy; and nitro.

The term "substituted aliphatic" as used herein refers to an alkyl or an alkane possessing less than 10 carbons. The term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.).

The term "cycloalkyl" as used herein refers to radicals having from about 3 to 15, 3 to 10, 3 to 8, or 3 to 6 carbon atoms and containing one, two, three, or four rings wherein such rings may be attached in a pendant manner or may be fused. In aspects of the disclosure, "cycloalkyl" refers to an optionally substituted, saturated hydrocarbon ring system containing 1 to 2 rings and 3 to 7 carbons per ring which may be further fused with an unsaturated C3-C7 carbocylic ring. Examples of cycloalkyl groups include single ring structures such as cyclopropyl, cyclobutyl, cyclopentyl, cyclohexyl, cycloheptyl, cyclooctyl, cyclononyl, cyclodecyl, cyclododecyl, and the like, or multiple ring structures such as adamantanyl, and the like. Tin certain aspects of the disclosure the cycloalkyl radicals are "lower cycloalkyl" radicals having from about 3 to 10, 3 to 8, 3 to 6, or 3 to 4 carbon atoms, in particular cyclopropyl, cyclobutyl, cyclopentyl, cyclohexyl and cycloheptyl. The term "cycloalkyl" also embraces radicals where cycloalkyl radicals are fused with aryl radicals or heterocyclyl radicals. A cycloalkyl radical may be optionally substituted with groups as disclosed herein.

The term "substituted cycloalkyl" as used herein includes cycloalkyl groups having from 1 to 5 (in particular 1 to 3) substituents including without limitation alkyl, alkenyl, alkoxy, cycloalkyl, substituted cycloalkyl, acyl, acylamino, acyloxy, amino, aminoacyl, aminoacyloxy, oxyacylamino, cyano, halogen, hydroxyl, carboxyl, carboxylalkyl, keto, thioketo, thiol, thioalkoxy, aryl, aryloxy, heteroaryl, heteroaryloxy, hydroxyamino, alkoxyamino, and nitro.

The term "cycloaliphatic" refers to a cycloalkane possessing less than 8 carbons or a fused ring system consisting of no more than three fused cycloaliphatic rings. Examples of such groups include, but are not limited to, decalin and the like.

The term "substituted cycloaliphatic" as used herein refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to, 1-chlorodecalyl and the like.

The term "substituted phenyl" refers to a phenyl group substituted with one or more moieties, and in some instances one, two, or three moieties, chosen from the groups consisting of halogen, hydroxy, protected hydroxy, cyano, nitro, trifluoromethyl, C1 to C7 alkyl, C1 to C7 alkoxy, C1 to C7 acyl, C1 to C7 acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—(C1 to C6 alkyl)carboxamide, protected N—(C1 to C6 alkyl)carboxamide, N,N-di(C1 to C6 alkyl)carboxamide, trifluoromethyl, N—((C1 to C6 alkyl)sulfonyl)amino, N-(phenylsulfonyl)amino or phenyl, substituted or unsubstituted, such that, for example, a biphenyl or naphthyl group results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy) phenyl group such as 2, 3 or 4-carboxyphenyl or 2,4-di (protected carboxy)phenyl; a mono- or di(hydroxymethyl) phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, etc., where optionally one or more pair of substituents together with the atoms to which they are bonded form a 3 to 7 member ring.

The term "heteroaryl" refers to optionally substituted five-membered or six-membered rings that have 1 to 4 heteroatoms, such as oxygen, sulfur and/or nitrogen atoms, in particular nitrogen, either alone or in conjunction with sulfur or oxygen ring atoms. Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings can include from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a C1 to C4 alkoxy group, similarly, "lower alkylthio" means a C1 to C4 alkylthio group.

The terms "heterocycle", "heterocyclic", "heterocyclic group" or "heterocyclo" refer to fully saturated or partially unsaturated or completely unsaturated, including aromatic ("heteroaryl") or nonaromatic cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

The terms "substituted heterocycle", "substituted heterocyclic", "substituted heterocyclic group" and "substituted heterocyclo" refer to heterocycle, heterocyclic and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substituents together with the atoms to which they are bonded form a 3 to 7 member ring.

"Isosteres" are different atoms, molecules, or ions that have different molecular formulae but have similar or identical outer shell electron arrangements and also have similar properties (e.g., pharmacological properties (e.g., pharmacokinetic and pharmacodynamic)).

The term "salt" as used with respect to the compounds of the disclosure herein may refer to embodiments of the agents that contain a basic moiety and which may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The term "tosylate" as used herein refers to the anion of p-toluenesulfonic acid ($CH_3C_6H_4SO_3^-$) and it is abbreviated as $TsO^-$.

The terms "subject", "individual", or "patient" as used herein are used interchangeably and refer to an animal, preferably a warm-blooded animal such as a mammal. Mammal includes without limitation any members of the Mammalia. A mammal, as a subject or patient in the present disclosure, can be from the family of Primates, Carnivora, Proboscidea, Perissodactyla, Artiodactyla, Rodentia, and Lagomorpha. In particular the embodiments of the disclosure are most advantageous for the administration, to and for the treatment of, disorders of human subjects, particularly those patients exhibiting symptoms of Alzheimer's disease. However, it is contemplated that the compositions and methods of the disclosure may be applied to other animals, and in particular mammals such as rodents, where an increase in TGF-β signaling is desired.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutically acceptable carriers can be liquids, such as water and oils, including those of petroleum, animal, vegetable or synthetic origin, such as peanut oil, soybean oil, mineral oil, sesame oil and the like. The pharmaceutically acceptable carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutically acceptable carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "pharmaceutically acceptable salt(s)" as used herein refers to those salts that are suitable for use in contact with the tissues of a subject or patient without undue toxicity, irritation, allergic response and the like, and are commensurate with a reasonable benefit/risk ratio.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The terms "pharmaceutically acceptable" or "pharmacologically acceptable" as used herein further refers to a material that is not biologically or otherwise undesirable, i.e., the material may be administered to an individual in a formulation or composition without causing any undesirable biological effects or interacting in a deleterious manner with any of the components of the composition in which it is contained.

Discussion

The present disclosure encompasses embodiments of derivatives of compound 11H that has the formula:

11H

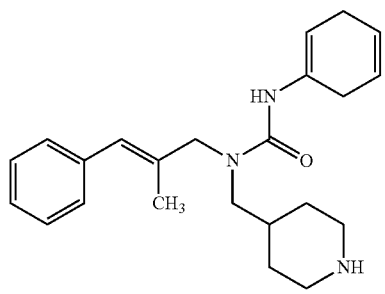

that has been identified as an agonist of TGF-β signaling. In particular, the compounds of the disclosure have the general formula I:

I

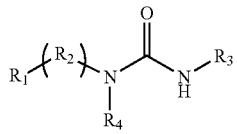

wherein it is contemplated that the $R_1$ group is a substituted phenyl. It is contemplated that $R_1$ may designate more than one substituent of the phenyl ring of formula I, including, but not limited to, one or more flurorines that can be independently positioned at the ortho, meta, or para positions thereof, and having, for example, but not limited to, any of the formulae a-z as shown in Example 2. However, it is contemplated that any substituent on the phenyl group can be within the scope of the disclosure with the criterium that the derivative has retained a detectable level of an agonist or antagonist activity with respect to TGF-β signaling, and most advantageously an agonist activity that mimics or positively modifies a detectable activity of a TGF-β.

In the compounds of the disclosure, $R_2$ may be selected from the group consisting of an —$CH_2$— group or —$CH=CH(CH_2)$—. In the compounds of the disclosure, $R_3$ may be selected from the group consisting of a cycloalkyl, including but not limited to a substituted or non-substituted $C_5$ or $C_6$ ring, or a substituted or non-substituted phenyl. In some advantageous embodiments of the compounds of the disclosure, the $R_2$ is a $C_6$ ring.

In the compounds of the disclosure, $R_4$ can be —$CH_2$—N-piperidine or N-piperidine. A compound of the disclosure can contain one or more asymmetric centers and may give rise to enantiomers, diasteriomers, and other stereoisomeric forms which may be defined in terms of absolute stereochemistry as (R)- or (S)-. Thus, compounds of the disclosure include all possible diasteriomers and enantiomers as well as their racemic and optically pure forms. Optically active (R)- and (S)-isomers may be prepared using chiral synthons or chiral reagents, or resolved using conventional techniques. When a compound of the disclosure contains centers of geometric asymmetry, and unless specified otherwise, it is intended that the compounds include both E and A geometric isomers. All tautomeric forms are also included within the scope of a compound of the disclosure.

A compound of the disclosure may include crystalline forms which may exist as polymorphs. Solvates of the compounds formed with water or common organic solvents are also intended to be encompassed within the term. In addition, hydrate forms of the compounds and their salts are encompassed within this disclosure. Further prodrugs of compounds of the disclosure are encompassed within the term.

Compounds of the disclosure may be amorphous or may have different crystalline polymorphs, possibly existing in different salvation or hydration states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility.

Crystalline compounds of the disclosure can be in the form of a free base, a salt, or a co-crystal. Free base compounds can be crystallized in the presence of an appropriate solvent in order to form a solvate. Acid salt compounds of the disclosure (e.g. HCl, HBr, benzoic acid) can also be used in the preparation of solvates. For example, solvates can be formed by the use of acetic acid or ethyl acetate. The solvate molecules can form crystal structures via hydrogen bonding, van der Waals forces, or dispersion forces, or a combination of any two or all three forces.

A compound of the disclosure can include a pharmaceutically acceptable co-crystal or a co-crystal salt. A pharmaceutically acceptable co-crystal includes a co-crystal that is suitable for use in contact with the tissues of a subject or patient without undue toxicity, irritation, allergic response and has the desired pharmacokinetic properties.

In the event that embodiments of the disclosed agents form salts, these salts are within the scope of the present disclosure. Reference to an agent of any of the formulas herein is understood to include reference to salts thereof, unless otherwise indicated. When an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), tosylate, and others.

Solvates of the agents of the disclosure are also contemplated herein. To the extent that the disclosed active compounds, and salts thereof, may exist in their tautomeric form, all such tautomeric forms are contemplated herein as part of the present disclosure.

All stereoisomers of the agents, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The disclosure further encompasses pharmaceutically acceptable compositions comprising any of the agonists of TGF-β signaling of the disclosure and suitable for administering an effective dose of the compound to an animal or human subject at risk for, or diagnosed with, a disease or condition characterized by reduced TGF-β signaling. The compositions of the disclosure encompass bioactive, small-molecule, TGF-β signaling agonist compounds that can, for example, advantageously cross the blood brain barrier (BBB). Reduction in TGF-β signaling is associated with such diseases and conditions as stroke, heart disease, bone loss, cancer, multiple sclerosis, wound healing, inflammation, and neurodegenerative disorders such as Alzheimer's disease. TGF-β agonists are known to reduce the number of amyloid plaques and overall accumulation of Aβ in the AD brain.

In another aspect, methods are provided for treating or preventing the progression of a disease or condition characterized by a reduction in TGF-β signaling. One category of such diseases or conditions is neurodegenerative disorders. One example is Alzheimer's disease (AD), or another disease characterized by the deposition of amyloid plaques and overall accumulation of Aβ in the brain. Experiments performed in support of the present compositions and methods are described, below.

TGF-β reporter gene and cells for screening compounds: An in vitro screening method was developed to identify small-molecule chemical compounds with TGF-β1-like bioactivity. The method utilized a fusion gene consisting of the luciferase or secreted alkaline phosphatase (SEAP) reporter gene under control of the TGF-β responsive Smad-binding element (SBE) minimal promoter sequence, as shown in FIGS. 1A and 1B. To screen for compounds that mimic TGF-β bioactivity, reporter cell lines were prepared by stably-integrating SBE-SEAP into C6 astrocytoma cells, a primary astrocyte line derived from tgfb1$^{-/-}$ mice, a mouse embryonic fibroblast cell line derived from tgfb1$^{-/-}$ mice (MFB-F11), and NG108-15 neuroblastoma cells. Such cell lines remained stable for at least 20 passages. Use of a tgfb1$^{-/-}$ genetic background avoids interference by the exogenous tgfb1 gene.

Initial compound screening: A library with 5,000 chemically diverse small molecules (average Mr 200 Da) was obtained from Comgenex LLC (South San Francisco, Calif.). To test compounds, or to assay individual stably-transfected cell lines for responsiveness to TGF-β1, 4×10$^4$ cells were seeded in 10% FBS/DMEM into 96-well plates and incubated overnight, washed twice, and exposed to test compounds (at 4 or 20 μM) or recombinant TGF-β1 (at 0 to 1,000 pg/ml) in serum-free medium (DMEM). Conditioned medium was assayed for SEAP activity 24 and 48 hours later.

As described in U.S. Pat. Nos. 8,097,645 and 8,410,138, both of which are herein incorporated by reference in their entireties, all compounds were tested twice, in duplicate, using the MFB-F11 cell line. 80 compounds were selected for further study based on induction of the reporter gene in any of the replicates. These compounds were tested again in MFB-F11 or C6-H4 cells, either alone or in the presence of 100 pg/ml of TGF-β1, to test for synergistic activities. Several compounds showed activities of up to an equivalent of 100 pg/ml TGF-β1 at 20 μM in the TGF-β1 deficient MFB-F11 cells. Some compounds showed dose-dependent activities.

The synthesis effort initially focused on modifications of the cyclohexyl ring that appears to be especially advantageous for activity. Thus, a cyclopentyl ring or a methyl group on the cyclohexyl ring substantially reduced or eliminated activity. An isostere modification by changing the carbamide to a thiocarbamide caused the loss of most of the activity. The molecules of the disclosure are tolerant of modifications in the $R_1$ and $R_2$ moieties and have the general formula I (see Example 1) and less tolerant of modification in the N-piperidine portion. Addition of a para-fluoro group on the phenyl ring of $R_1$ gave activity similar to that of compound 11H, although it is contemplated that more than one halogen or other substituent may be tolerated on the ring of $R_1$.

Compound SRI-011382 (382) showed superior activity in the reporter cell assay and had a desirable level of metabolic stability, suggesting that incorporating fluorine was advantageous. To lower the ClogP of this series it was necessary to decrease the lipophilicity of the scaffold. To accomplish this, the carbon linker was reduced to the aryl substituent. Compound SRI-011381 (381) also showed activity in the reporter cell assay. This compound has a ClogP of 3.4. Adding fluorine to the scaffold did not increase activity in the reporter cell assay (analogs SRI-011474 through SRI-011276), but these compounds should have increased metabolic stability. Alternative urea functionalities that decrease the ClogP (SRI-011954 through SRI-011956) were also investigated. Compound SRI-011956 (the tysolated salt version of compound SRI-011382 (382)) showed superior activity at low micromolar concentrations in the reporter assay and had no significant CYP inhibition.

The compounds were all tested in the F11 cell activity assay (fibroblast stably transfected with SBE-SEAP construct). A subset of the compounds was then tested in ADMET assays. Compounds with promising activity were evaluated using tier 1 assays such as permeability assays to measure blood-brain barrier transport, metabolic stability assays, and solubility assays. A second tier hepatocyte toxicity assay was performed on a smaller number of compounds that had promising results in the tier 1 assays. Criteria were set for each assay based on the initial values of SRI-011272 (11H).

The most promising compounds out of these screens were tested for their neuroprotective potential in B103 rat neuroblastoma cells and primary mouse neurons derived from E16 forebrains. Compounds were also tested for their capacity to reduce varicosities and tortuosity in primary mouse neurons. Accordingly, novel neuroprotectant small molecules have been identified that are as potent or better than TGF-β. Importantly, they fulfilled the critical neuroprotective properties in neuronal cell lines and primary hippocampal mouse neurons.

Compounds based on the 11H core: The present compositions and methods include salts of the active compounds and formulations, in particular pharmaceutically acceptable compositions for administration to an animal or human subject and containing active compounds. 129 analogs or derivatives of 11H were screened by a cell-based assay for their ability to increase TGF-β activity, i.e. to act as a TGF agonist. In particular, one compound (a) designated as SRI-011381 (381) was identified as especially advantageous, although active derivatives thereof are contemplated and have been identified.

Effects of TGF-β analogs in vitro: Some of the small-molecule TGF-β agonist compounds were tested for neuroprotection activity and toxicity in vitro (cell culture). In addition, the mechanism of action of the agonists was explored using cells with different genetic backgrounds with respect to protein of the TGF-61 signaling pathway.

Animal studies: Transgenic mice harboring the SBE-luc reporter gene were generated and used to test the derivatives of compound 11H in vivo. These "reporter mice" mice express SBE-luc (i.e., "the transgene") in all cells of the body. Intraperitoneal injection of luciferin into SBE-luc-expressing mice produces bioluminescence generated by luciferase and photons penetrating the skull can be imaged using sensitive camera systems.

Experiments performed in support of the present compositions and methods show that TGF-β1 is neuroprotective and can reduce the accumulation of Aβ in an animal model. Small-molecule agonists of TGF-β1 modulated TGF-β signaling and activated a reporter gene in the brains of transgenic mice. Together, these data indicate that agonists of the TGF-β signaling pathway can be used to reduce or prevent amyloid plaques and Aβ accumulation in the CNS, thereby treating or preventing Alzheimer's disease (AD) and associated diseases. While the present compositions and methods relate primarily to TGF-β1 signaling, one skilled in the art will recognize that TGF-62 and β3 can be modulated in a similar manner.

While the present compositions and methods are described mainly for treatment and prevention of AD, other neurodegenerative diseases are characterized by amyloid plaques and/or accumulation of Aβ in the brain and, therefore, can be treated or prevented in a similar manner using the compounds of the disclosure. Such diseases/disorders include localized amyloidosis while as well as systemic amyloidosis.

SRI-011381 (381) was rapidly absorbed after oral administration to FBV mice with an oral bioavailability of approximately 50%. The apparent volume of distribution suggests extensive tissue distribution. The concentration of SRI-011381 in the brain was lower than plasma levels, but the compound was cleared more slowly from the brain than from plasma, until the brain:plasma ratio was greater than 0.5.

Repeat dose administration of SRI-011381 (381) by oral gavage of 10, 30, and 75 mg/kg for 14 days resulted in significant changes in hematological endpoints, most notably reductions in red blood cells (RBCs), hematocrit and hemoglobin, while reticulocytes were significantly elevated as a compensation for reduction in the RBCs. The MTD and NOAEL for SRI-011381 (381) in FBV female mice were determined to be 75 mg/kg and less than about 30 mg/kg, respectively.

The adverse effects on hematology parameters were not observed in the range finding study in male and female APP751$^{LonSwe}$ swe mice. The formulated compound was administered orally at 0 (vehicle only), 10, 30, 60, or 100 mg/kg 3 times a week for 2 weeks, mimicking the dose regimen used in efficacy studies. There were no statistically significant changes between treated groups and controls in any of the clinical chemistry or hematology parameters that were studied. In addition, there were no significant differences in body weight. Thus the maximum tolerated dose (MTD) of SRI-011381 (381), administered 3 times per week for 2 weeks to APP751$^{LonSwe}$ mice was greater than 100 mg/kg.

Methods of treatment: The present compositions are useful in the preparation of a pharmaceutically acceptable composition or medicament for treating or preventing diseases and conditions associated with reduced TGF-β signaling, including neurological disorders. In a particular example, the compositions are useful in treating or preventing AD or other diseases characterized by neurodegeneration. In some embodiments, the composition is provided in a pharmaceutical excipient suitable for oral delivery. In some embodiments, the composition is provided in a pharmaceutical excipient suitable for ip., iv., or im. delivery.

One aspect of the disclosure, therefore, encompasses embodiments of a TGF-β signaling agonist having the formula I:

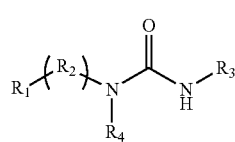

I wherein R₁ group is a substituted phenyl; R₂ can be —CH₂— group or —CH=CH(CH₂)—; R₃ can be selected from the group consisting of: a substituted or non-substituted $C_5$ or $C_6$ cycloalkyl, and a substituted or non-substituted phenyl, and R₄ can be —CH₂—N-piperidine or N-piperidine, or a pharmaceutically acceptable salt thereof.

In some embodiments of this aspect of the disclosure, R₁ can be a phenyl group or a phenyl substituted with at least one halogen.

In some embodiments of this aspect of the disclosure, R₁ can be a phenyl substituted with at least one fluorine.

In some embodiments of this aspect of the disclosure, the agonist can be protonated at the N-piperidine and the pharmaceutically acceptable salt is a chloride or a tosylate.

In some embodiments of this aspect of the disclosure, the agonist, or a pharmaceutically acceptable salt thereof, can be selected from the group consisting of the formulas:

a

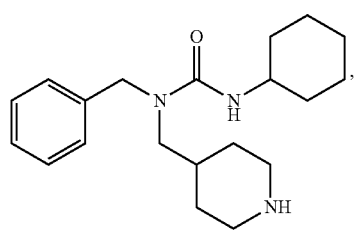

b

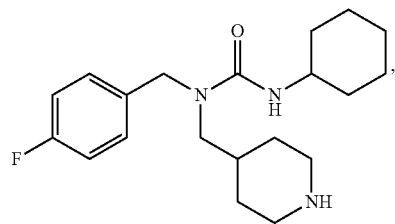

c

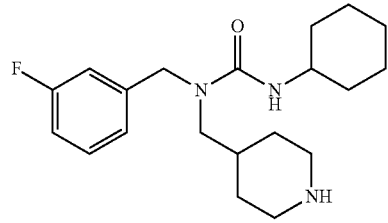

d

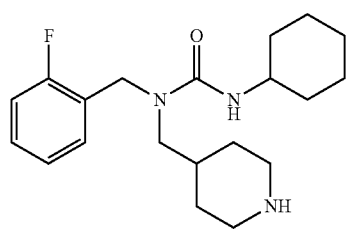

e

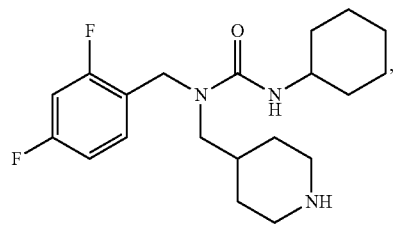

-continued f

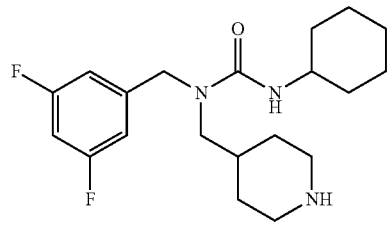

g

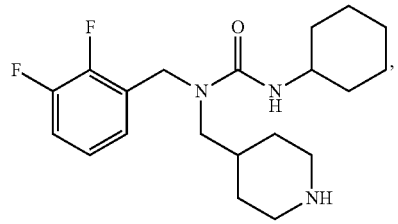

h

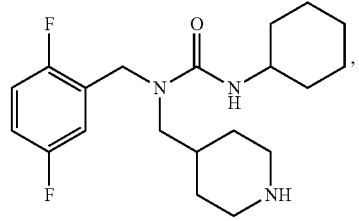

i

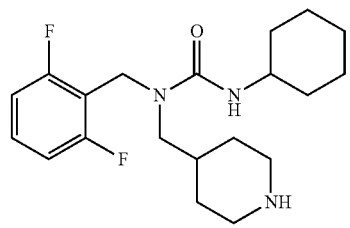

j

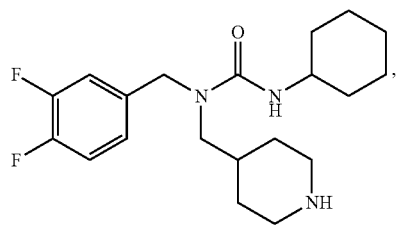

k

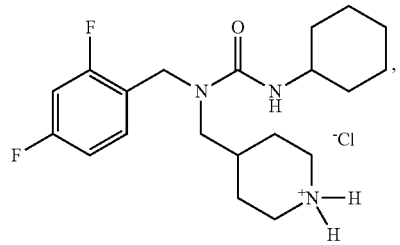

l
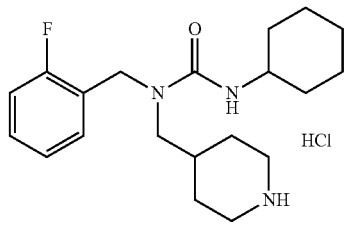
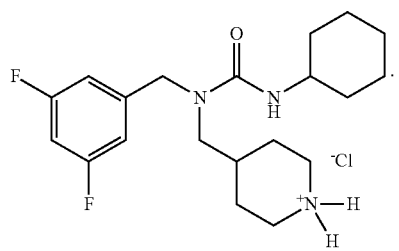
m
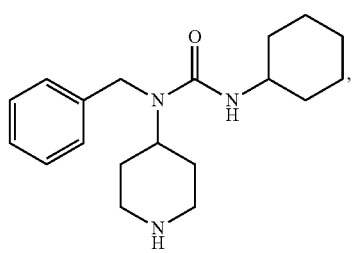
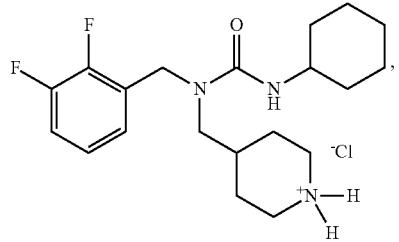
n
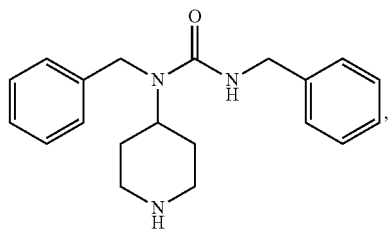
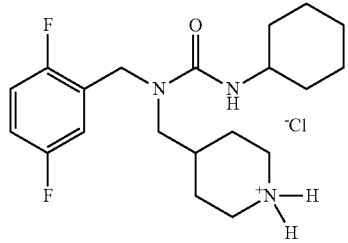
o
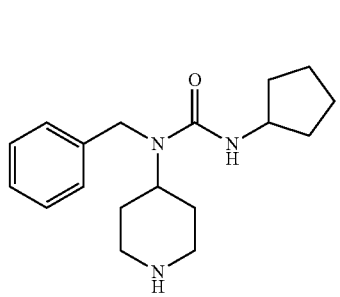
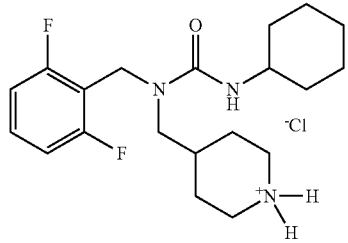
p
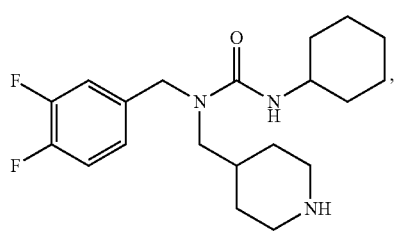
v
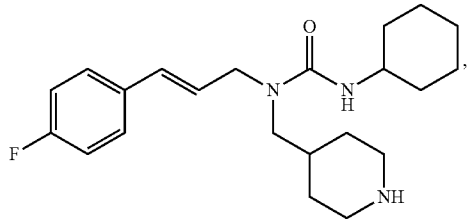
q
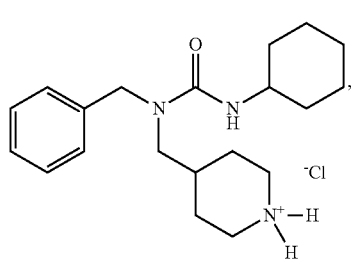
w
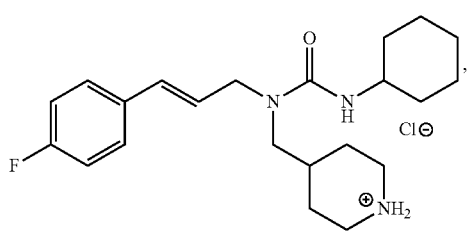

-continued

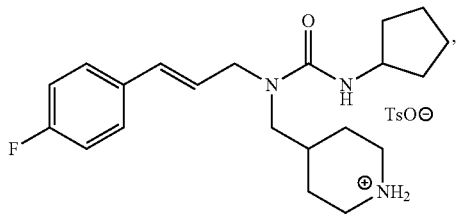
x

, and
y

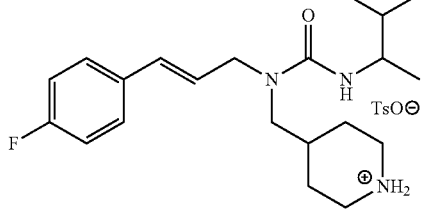
z

In some of these embodiments of this aspect of the disclosure, the agonist, or a pharmaceutically acceptable salt thereof, can be selected from the group consisting of the formulas a-u:

In some of these embodiments of this aspect of the disclosure, the agonist, or a pharmaceutically acceptable salt thereof, can be selected from the group consisting of the formulas v-z:

Another aspect of the disclosure encompasses embodiments of a pharmaceutically acceptable composition comprising a TGF-β signaling agonist having the formula I:

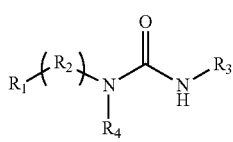
I wherein $R_1$ group is a substituted phenyl; $R_2$ can be —$CH_2$— group or —CH=CH($CH_2$)—; $R_3$ can be selected from the group consisting of: a substituted or non-substituted $C_5$ or $C_6$ cycloalkyl, and a substituted or non-substituted phenyl, and $R_4$ can be —$CH_2$—N-piperidine or N-piperidine, or a pharmaceutically acceptable salt thereof, and a pharmaceutically acceptable carrier.

In some embodiments of this aspect of the disclosure, the pharmaceutically acceptable composition can be formulated to deliver an effective amount of the TGF-β agonist to a mammalian subject.

In some embodiments of this aspect of the disclosure, the pharmaceutically acceptable composition can be formulated for administration to a recipient mammalian subject by oral, intraperitoneal, intravenous, or intramuscular administration.

In some embodiments of this aspect of the disclosure, the agonist, or a pharmaceutically acceptable salt thereof, can be selected from the group consisting of the formulas:

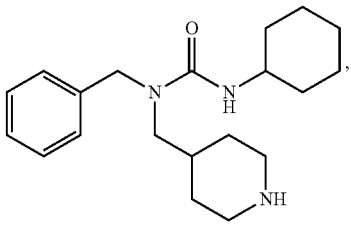
a

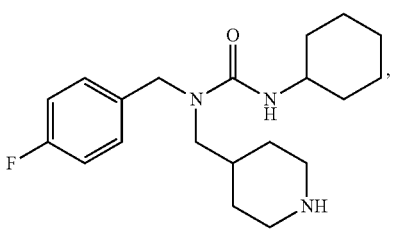
b

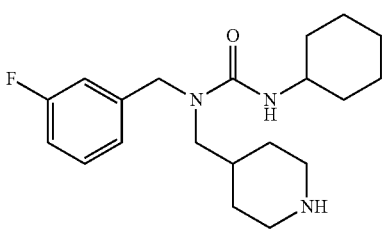
c

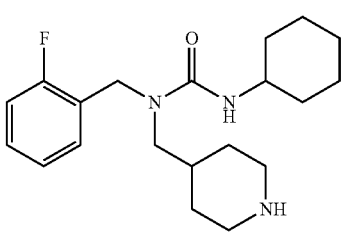
d

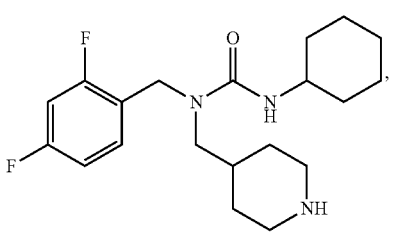
e

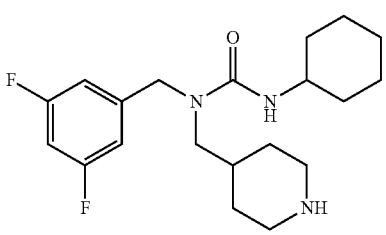
f g
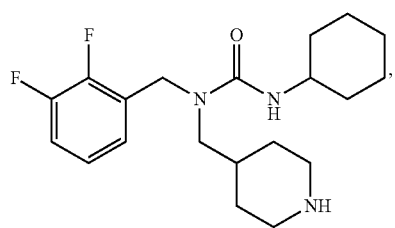
h
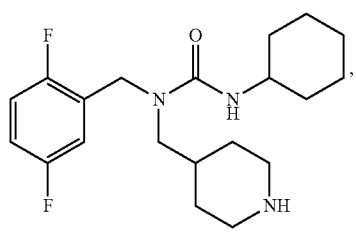
i
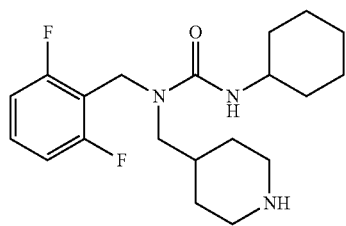
j
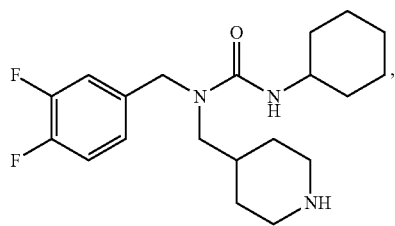
k
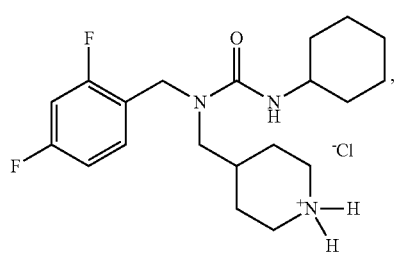
l
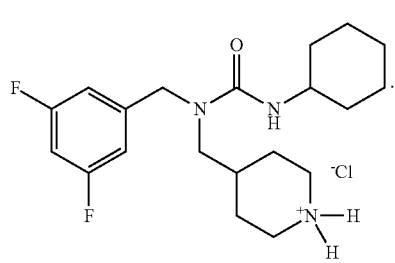
m
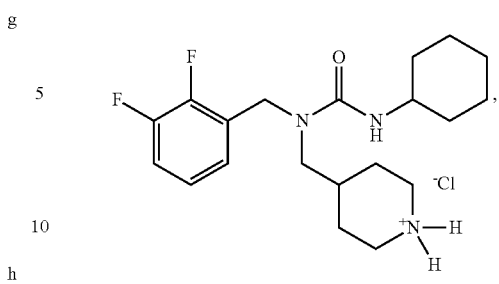
n
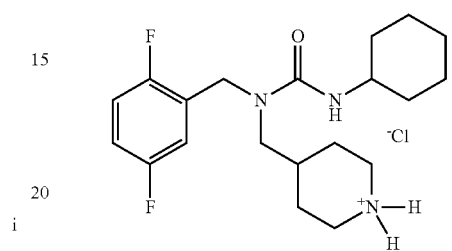
o
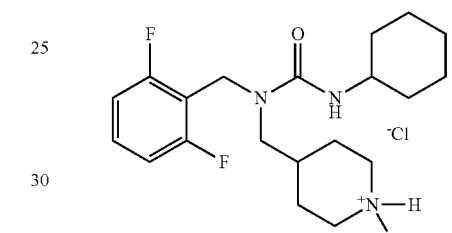
p
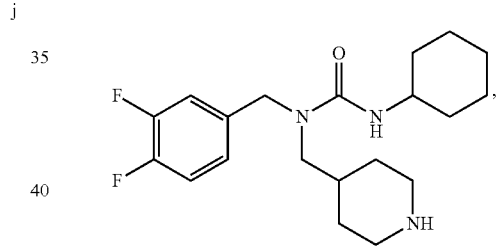
q
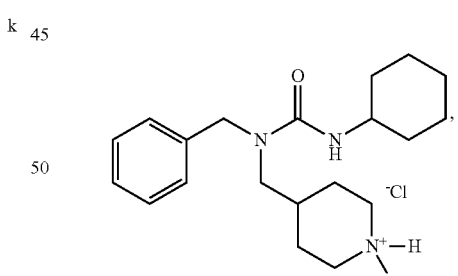
r
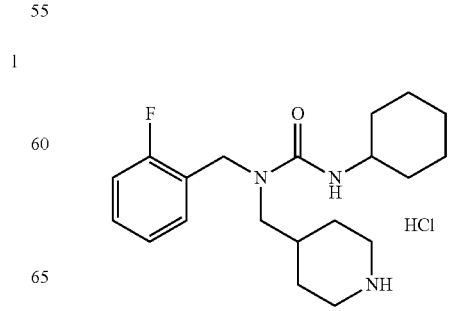

s

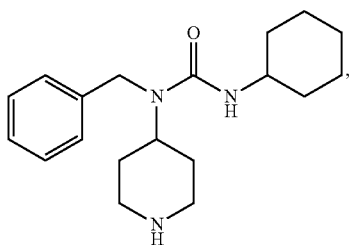

t

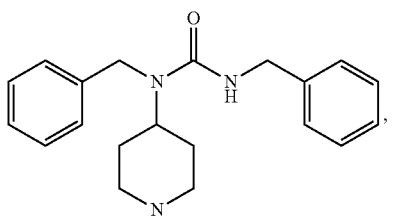

u

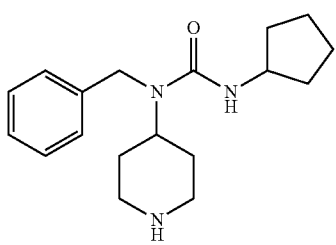

v

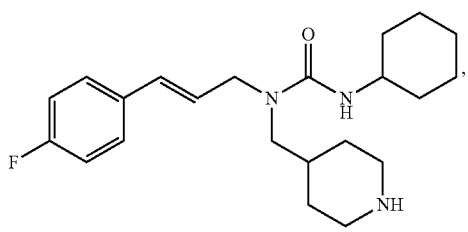

w

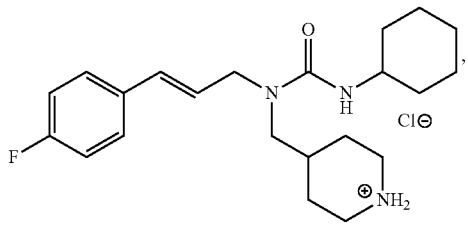

x

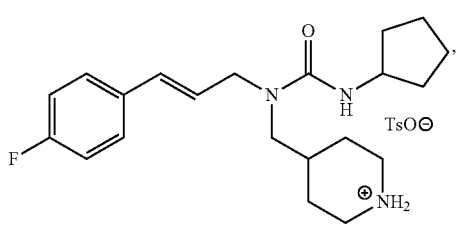

y

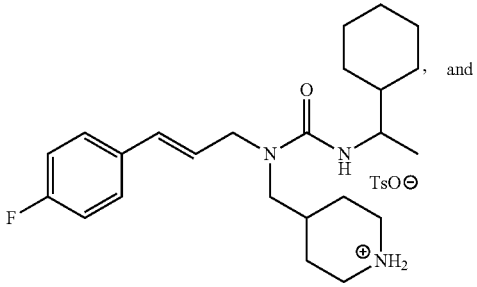

, and z

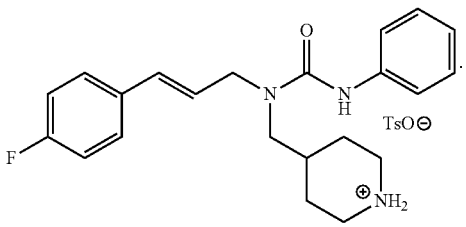

.

Still another aspect of the disclosure encompasses embodiments of a method of increasing TGF-β signaling activity of a cell, comprising the step of contacting the cell with an effective dose of a TGF-β signaling agonist having the formula I:

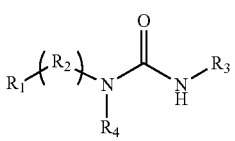

I wherein $R_1$ group is a substituted phenyl; $R_2$ can be —$CH_2$— group or —CH═CH($CH_2$)—; $R_3$ can be selected from the group consisting of: a substituted or non-substituted $C_5$ or $C_6$ cycloalkyl, and a substituted or non-substituted phenyl, and $R_4$ can be —$CH_2$—N-piperidine or N-piperidine, or a pharmaceutically acceptable salt thereof, and a pharmaceutically acceptable carrier.

In some embodiments of this aspect of the disclosure, the agonist, or a pharmaceutically acceptable salt thereof, can be selected from the group consisting of the formulas:

a

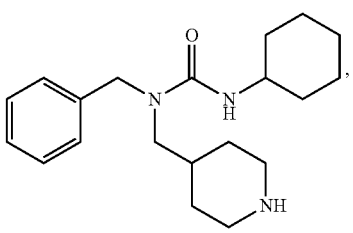

,

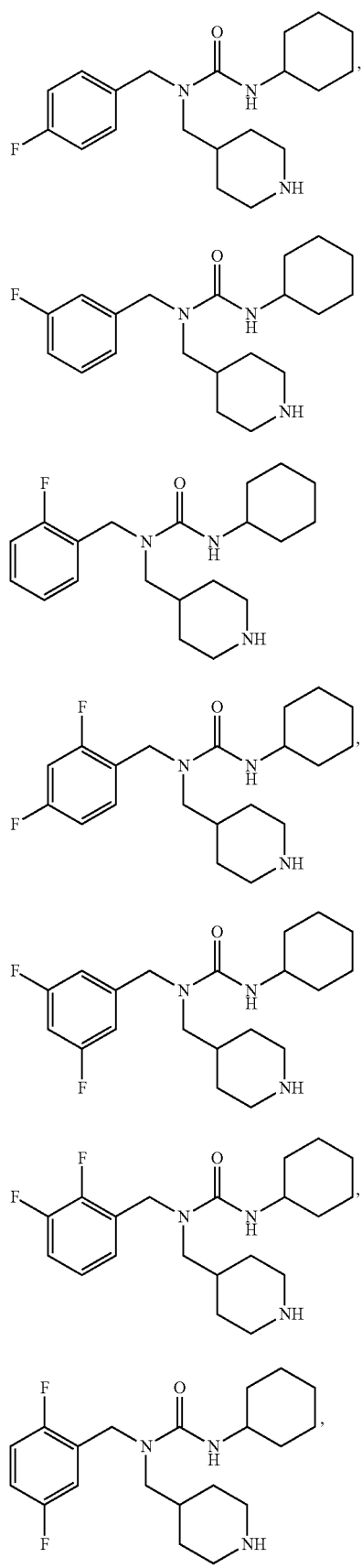
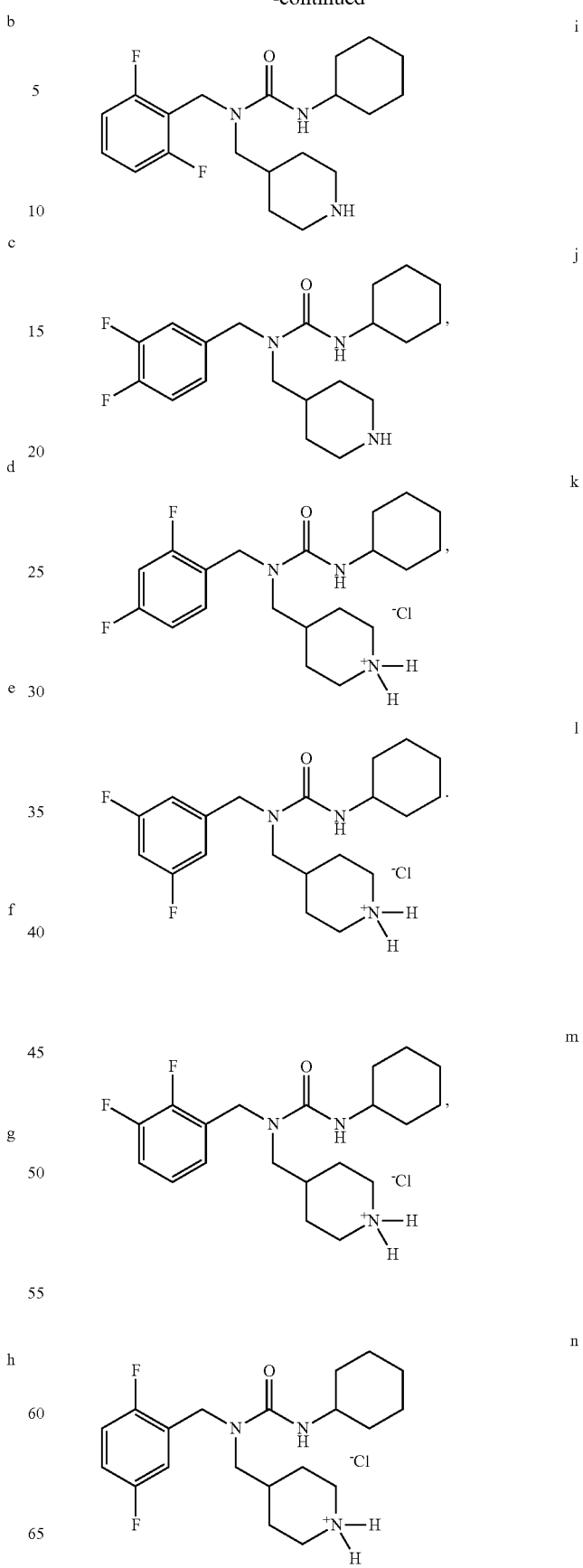

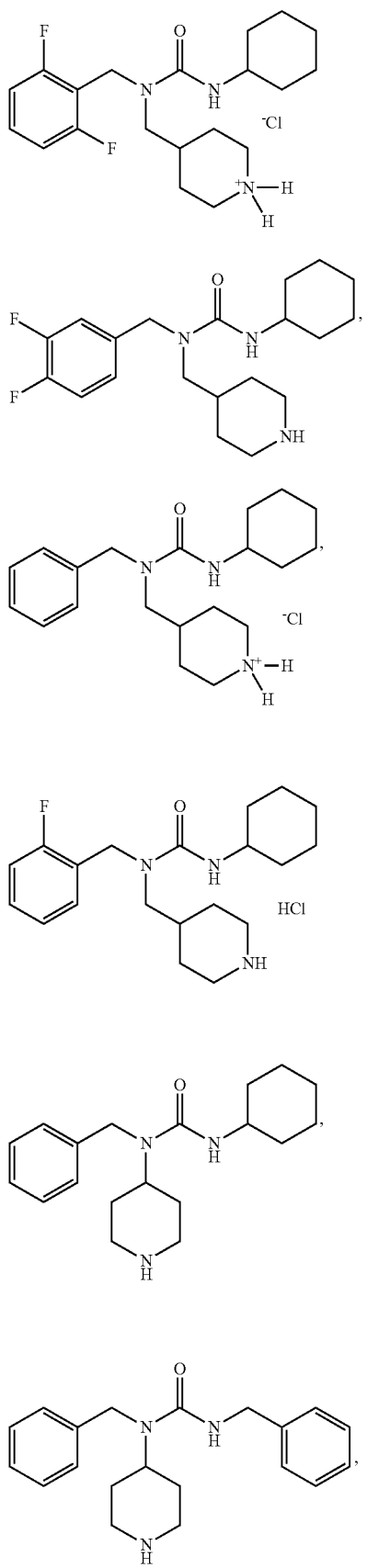
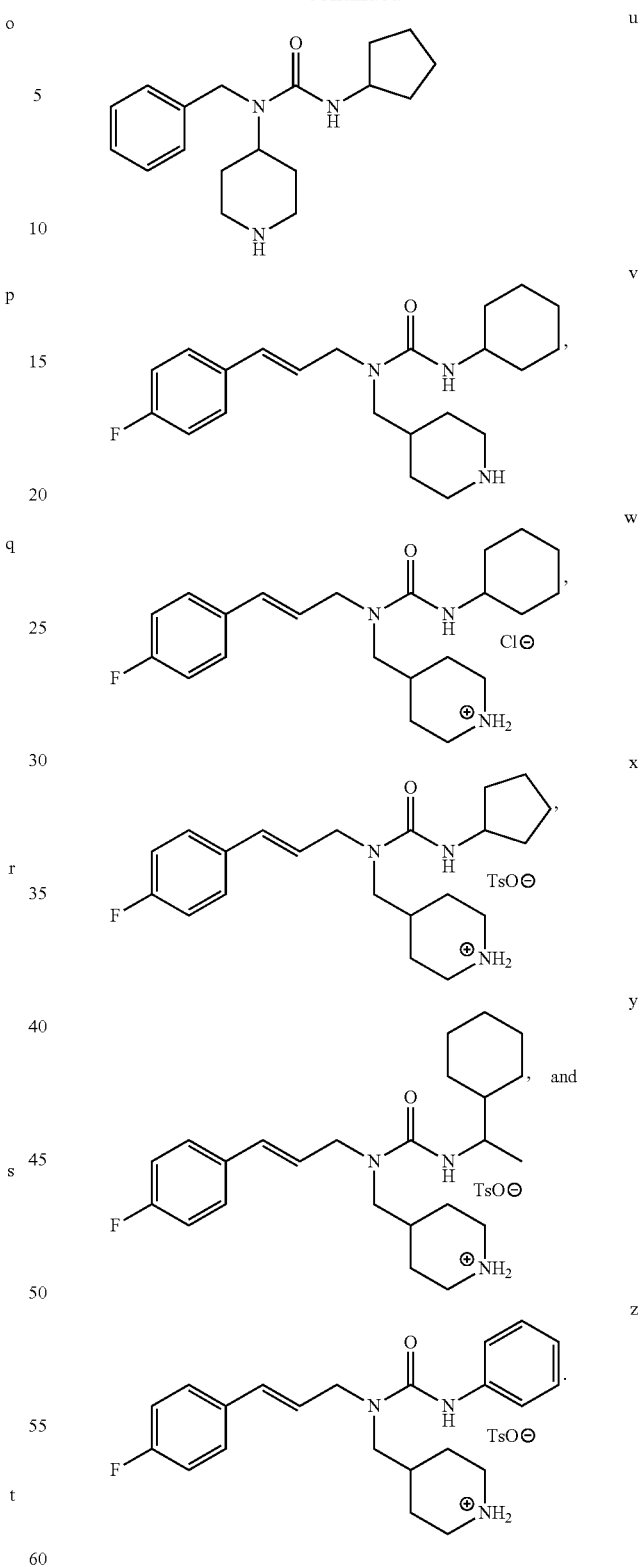
In some embodiments of this aspect of the disclosure, the effective dose of the TGF-β signaling agonist can be combined with a pharmaceutically acceptable carrier in a pharmaceutically acceptable composition formulated for delivery of the agonist to a cell or population of cells of a mammalian subject.

In some embodiments of this aspect of the disclosure, the method can further comprise the step of administering the pharmaceutically acceptable composition to a mammalian subject.

In some embodiments of this aspect of the disclosure, the increased TGF-β signaling activity can be in a cell of the brain of the recipient subject.

In some embodiments of this aspect of the disclosure, the mammalian subject can have a disease or condition characterized by reduced TGF-β signaling activity, and wherein an increase in TGF-β signaling activity can be advantageous to the mammalian subject.

In some embodiments of this aspect of the disclosure, increasing TGF-β signaling activity can provide at least one of an enhancement of neuroprotection, an enhancement of cognitive behavior, and a reduction of neurodegeneration in the brain of the mammalian subject.

In some embodiments of this aspect of the disclosure, the compound can be effective to reduce the number of amyloid plaques in the brain.

In some embodiments of this aspect of the disclosure, the compound can be effective to reduce the accumulation of Aβ in the brain.

In some embodiments of this aspect of the disclosure, the disease or condition can be Alzheimer's disease.

Yet another aspect of the disclosure encompasses embodiments of a method of increasing TGF-β signaling activity in the brain of a subject with Alzheimer's disease, the method comprising the step of: administering to a subject with Alzheimer's disease, or suspected of having Alzheimer's disease, a pharmaceutically acceptable composition comprising; (a) an effective dose of a TGF-β signaling agonist having the formula I:

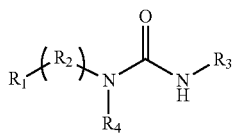

I wherein $R_1$ group is a substituted phenyl; $R_2$ can be —$CH_2$— group or —CH=CH($CH_2$)—; $R_3$ can be selected from the group consisting of: a substituted or non-substituted $C_5$ or $C_6$ cycloalkyl, and a substituted or non-substituted phenyl, and $R_4$ can be —$CH_2$—N-piperidine or N-piperidine, or a pharmaceutically acceptable salt thereof; and (b) a pharmaceutically acceptable carrier; and wherein: (1) an increase in TGF-3 signaling activity is advantageous to the subject; and (2) the TGF-β signaling agonist is effective to reduce at least one of the number of amyloid plaques in the brain and the accumulation of Aβ in the brain.

In some embodiments of this aspect of the disclosure, the agonist, or a pharmaceutically acceptable salt thereof, can be selected from the group consisting of the formulas:

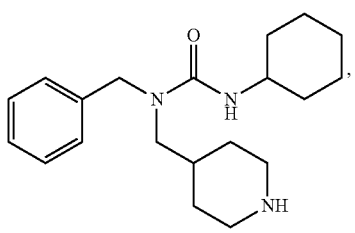

a

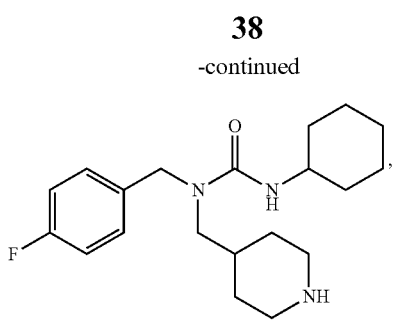

b

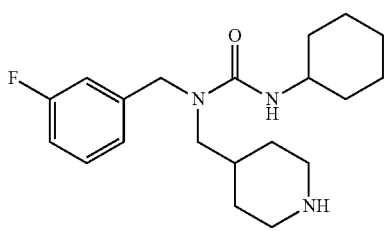

c

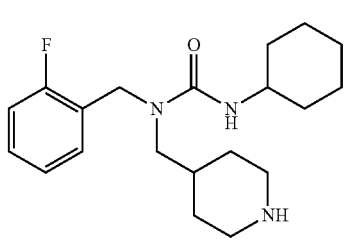

d

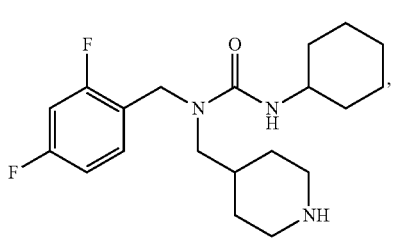

e

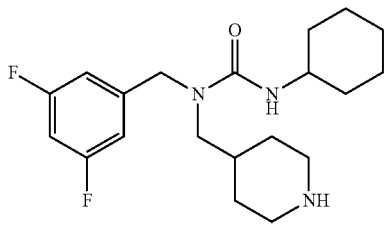

f

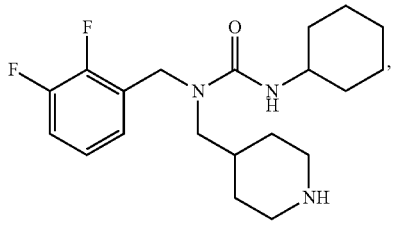

g

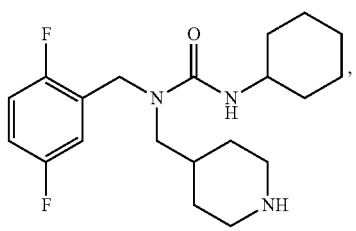

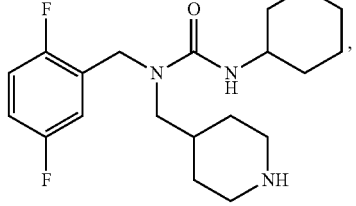

h

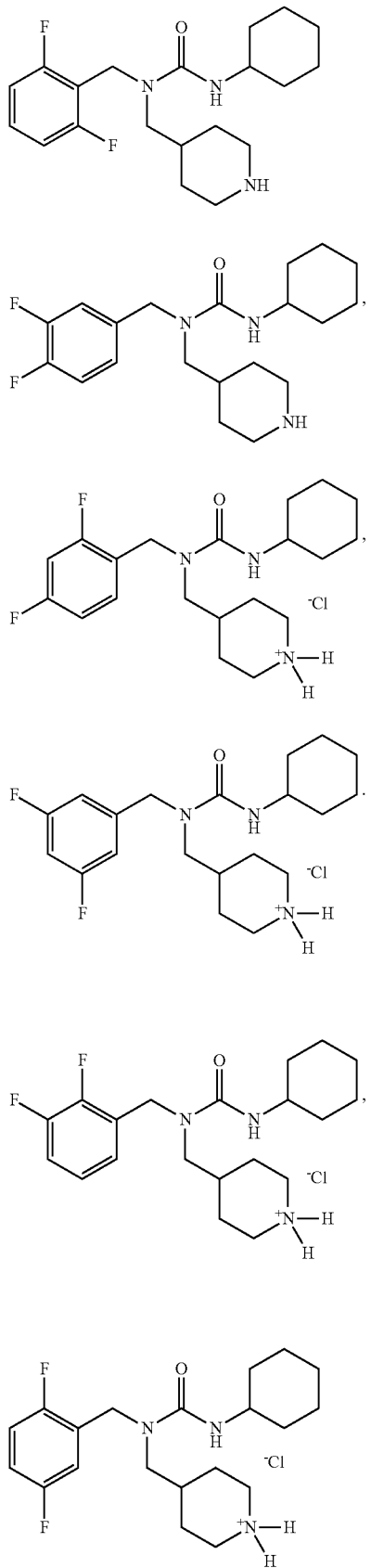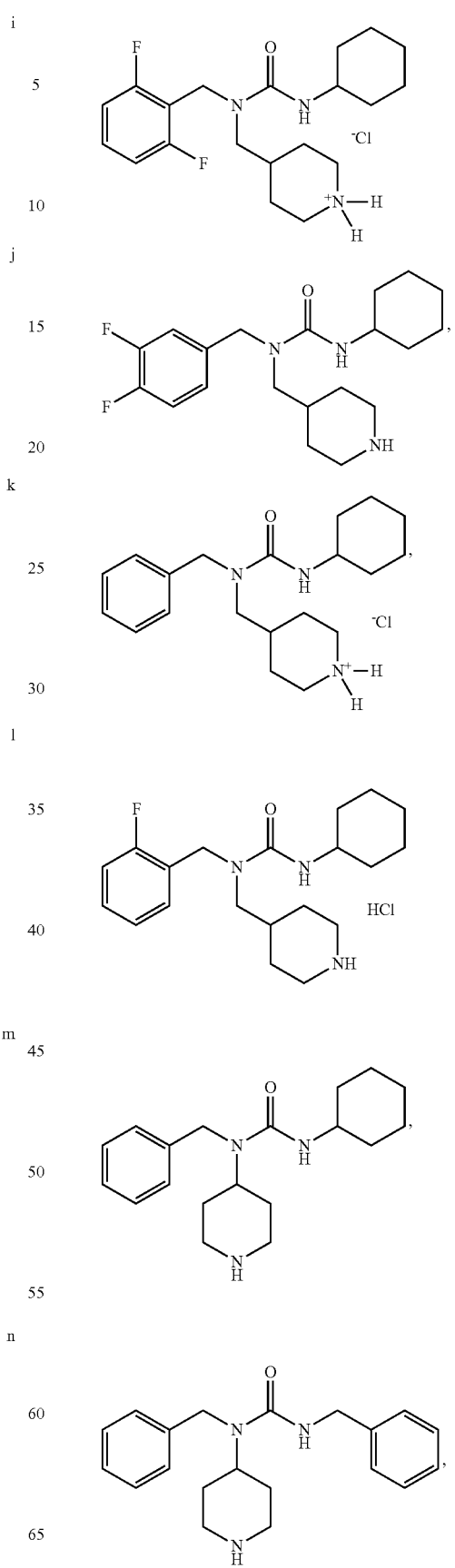

-continued

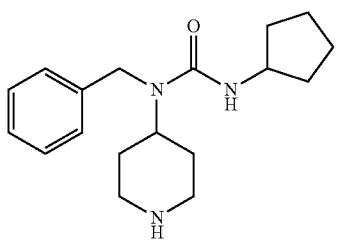

u

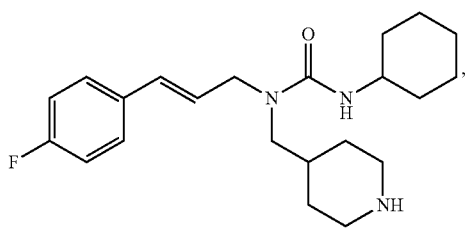

v

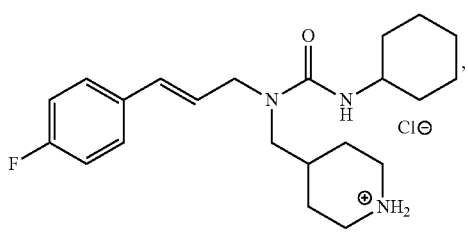

w

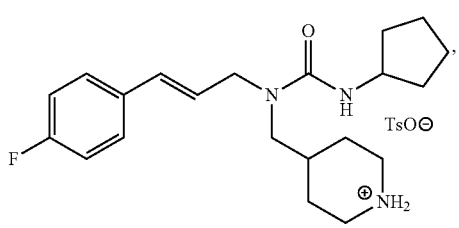

x

y

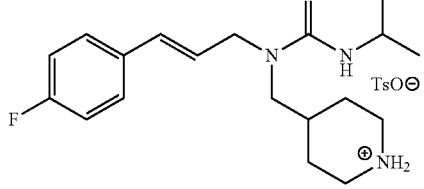
and z

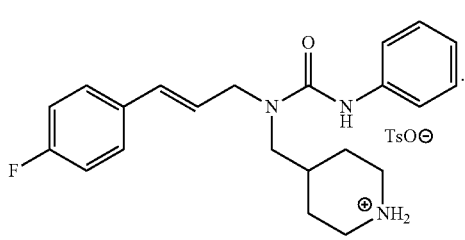

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

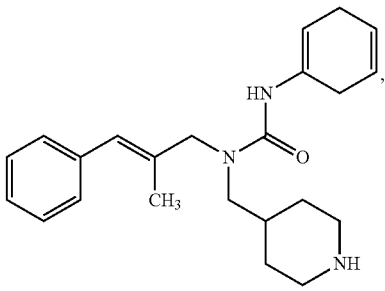
11H

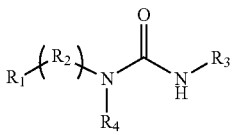
I

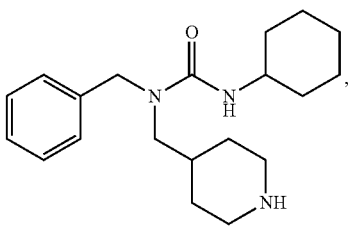

SRI-011381 (381, a))

Example 2
(a) 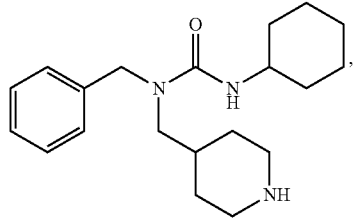
SRI-011381
(b) 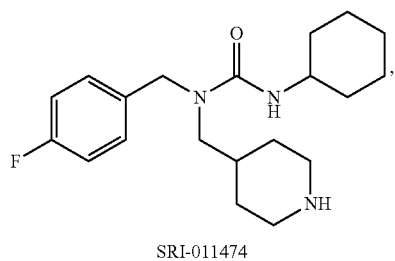
SRI-011474
(c) 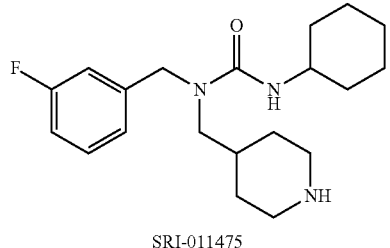
SRI-011475
(d) 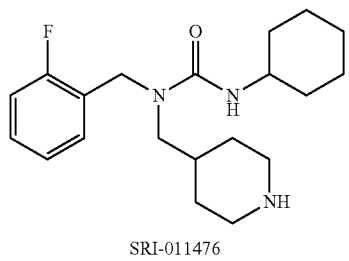
SRI-011476
(e) 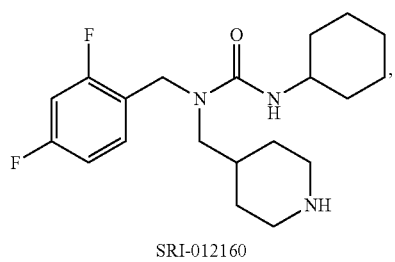
SRI-012160
(f) SRI-012161
(g) SRI-012162
(h) SRI-012163
(i) SRI-012164
(j) SRI-012165
(k) SRI-012170

(l)
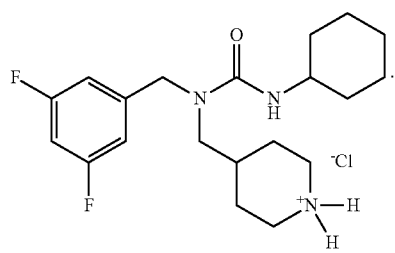
SRI-012171
(m)
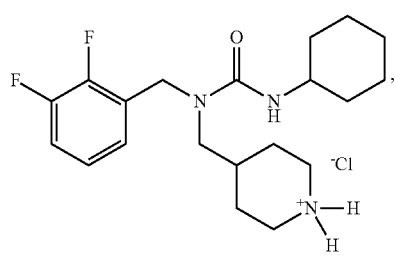
SRI-012172
(n)
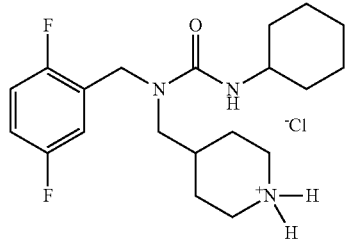
SRI-012173
(o)
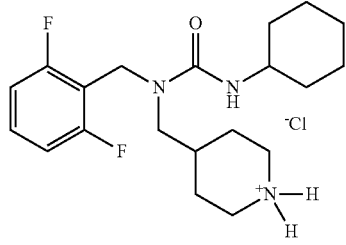
SRI-012174
(p)
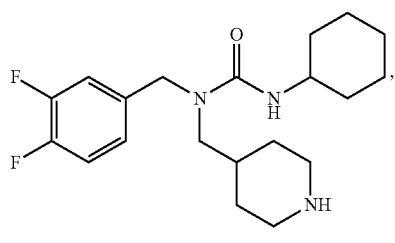
SRI-012175
(q)
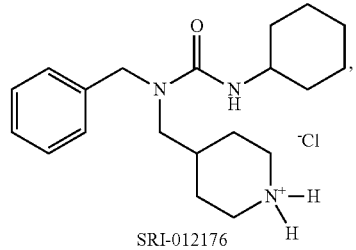
SRI-012176
(r)
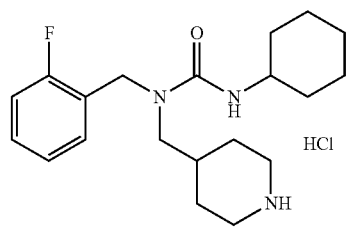
SRI-012177
(s)
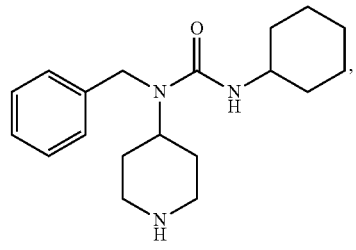
SRI-012031
(t)
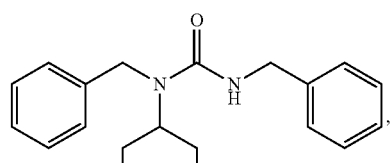
SRI-012032
(u)
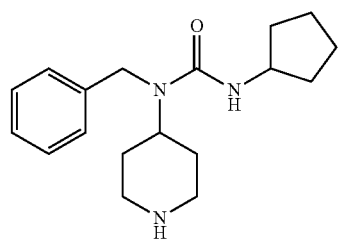
SRI-012033
(v)
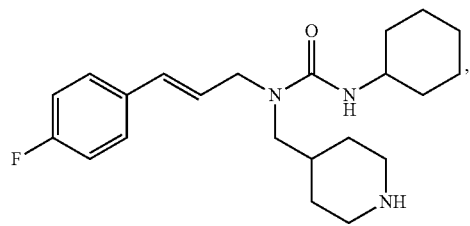
SRI-011382

-continued (w)
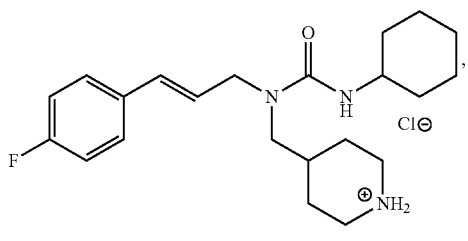
SRI-011821

(x)
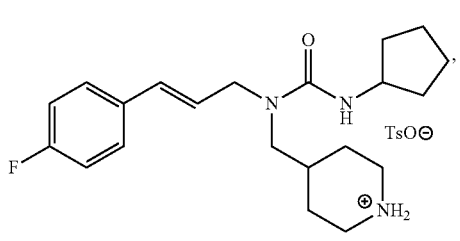
SRI-011954

(y)
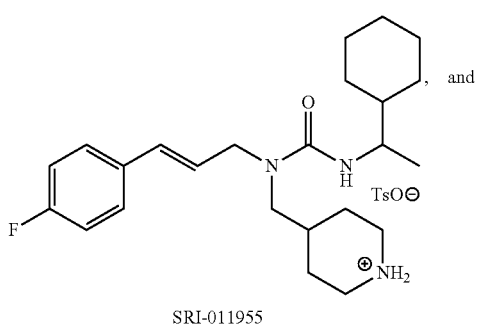
SRI-011955

, and (z)
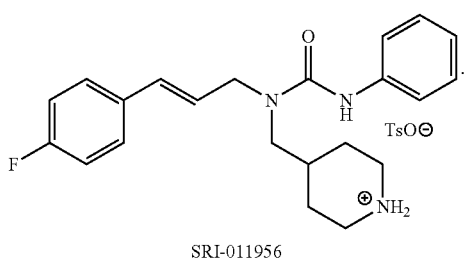
SRI-011956

Example 3

TABLE 1

Physical properties of SRI-011381 (381, a)

| | |
|---|---|
| Chemical Name: | 1-Benzyl-3-cyclohexyl-1-(piperidin-4-ylmethyl)urea |
| Molecular Weight: | 329.48 |
| Formula: | $C_{20}H_{31}N_3O$ |
| Description: | Physical appearance: White powder |
| Physical/Chemical Properties | tPSA: 44.4; cLogP: 3.30 |
| | Solubility: 5.2 mg/mL in PBS |

TABLE 2

Test performed to confirm the identity of SRI-011381

| Identity Test | Result |
|---|---|
| Appearance | The material is a white powder. |
| Analysis of purity by high-pressure liquid chromatography (HPLC) | The material is >98% pure by peak area, with a maximum individual impurity of 0.50%. |
| Melting Point | 92.5-95.5° C. |
| Mass spectrometry (MS): | A molecular weight of 329.48 amu was confirmed. |
| The Fourier-transform infrared (FT-IR): | The spectrum was consistent with the assigned structure. |
| Proton Fourier-Transform Nuclear Magnetic Resonance ($^1$H FT-NMR): | The $^1$H FT-NMR spectrum was obtained in deuterated chloroform (CDCl$_3$). The resulting spectrum was consistent with the indicated |
| Carbon Fourier-Transform Nuclear Magnetic resonance ($^{13}$C FT-NMR): | The $^{13}$C FT-NMR spectrum was obtained in deuterated chloroform (CDCl$_3$). The resulting spectrum was consistent with the indicated |
| Liquid Chromatography Mass Spectrometry (LCMS): | A molecular weight of 329.48 amu was confirmed using LCMS with electrospray ionization detection. |

Elemental Analysis

Results from elemental analysis of SRI-011381 (381) are provided in Table 4. Results are consistent with the proposed structure as shown in Example 1.

TABLE 4

Elemental Analysis of SRI-011381

| Element | Theoretical (w/w) | Found (w/w) |
|---|---|---|
| Carbon | 71.35 | 71.55 |
| Hydrogen | 12.48 | 12.23 |
| Nitrogen | 9.52 | 9.53 |

Example 4

SRI-011381 (otherwise designated as 381 or (a), has been formulated for administration to animals. The compound was formulated for the earliest studies in 10% DMSO: 15% Solutol:75% sterile water. Subsequently, it was determined that the DMSO could be eliminated and SRI-011381 has been formulated in 15% Solutol:85% sterile water for oral gavage.

Example 5

Figure 6:
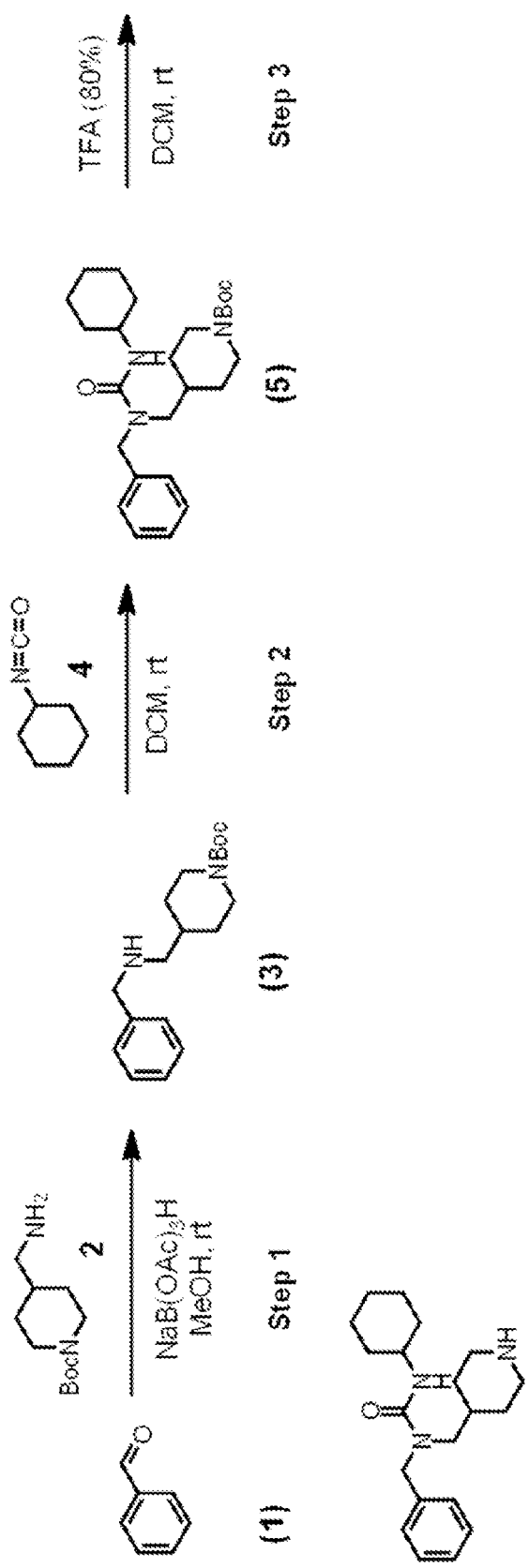
FIG. 6 illustrates the flow diagram of a SRI-011381 (381) synthetic process.

Synthesis of SRI-011381: The synthesis of SRI-011381 involved three steps, shown in the synthetic flow diagram in FIG. 6, as follows:

Step 1: Preparation of tert-Butyl 4-((benzylamino)methyl) piperidine-1-carboxylate (3) To a solution of benzaldehyde (1, 13.70 g, 64.0 mmol) in methanol (200 mL) was added the primary amine (2, 6.53 mL, 64.0 mmol). This solution was stirred for 8 h at room temperature (RT). Then sodium triacetoxyborohydride (27.14 g, 128.0 mmol) was added in three solid portions over 20 min. The reaction mixture was stirred at room temperature overnight. The reaction was quenched by the addition of 2.5 M NaOH until pH 11 was obtained. This mixture was stirred for 30 min. The reaction mixture was then extracted with ethyl acetate (3×300 mL). The combined organics were washed with brine (1×200 mL), dried over Na$_2$SO$_4$ (sodium sulfate), filtered, the volatiles were removed, and the crude oil was purified using flash column chromatography (40:1 DCM:MeOH). The product 3 was isolated as an oil (13.50 g, 69% yield).

Step 2: Preparation of tert-Butyl 4-((1-benzyl-3-cyclohexylureido)methyl)piperidine-1-carboxylate (5) To a solution of amine 3 (13.50 g, 44.4 mmol) in dichloromethane (200 mL) was added cyclohexylisocyanate (4, 11.25 mL, 88.8 mmol) neat dropwise. The reaction mixture was stirred for 20 h at RT. The reaction was quenched by the addition of a saturated aqueous solution of $NaHCO_3$. The layers were separated, and the aqueous layer was extracted with ethyl acetate (2×200 mL). The combined organics were washed with brine (1×100 mL), dried over $Na_2SO_4$, filtered, and the volatiles were removed in vacuo. The crude oil was purified by flash column chromatography (3:1->1:1 hexane:EtOAc). Carbamate 5 was isolated as an oil (17.3 g, 91% yield).

Step 3: Preparation of 1-Benzyl-3-cyclohexyl-1-(piperidin-4-ylmethyl)urea (SRI-011381) To a solution of carbamate 5 (17.0 g, 39.6 mmol) in dichloromethane (300 mL) was added 80% (vol/vol) aqueous TFA (15 mL) neat. The reaction mixture was stirred at room temperature for 4 h. The reaction was quenched by the addition of 2.5 M NaOH until pH 11 was reached. The reaction mixture was extracted with ethyl acetate (3×200 mL), and the combined organics were washed with brine (1×150 mL), dried over $Na_2SO_4$ and filtered. Volatiles were removed in vacuo and the product was dried under high vacuum. SRI-011381 was obtained as a white powder (13.0 g, 99% yield). $^1H$ NMR (400 MHz, $CDCl_3$): δ 7.20-7.40 (m, 5H), 4.45 (s, 2H), 4.13 (d, 1H, J=7.0 Hz), 3.63 (m, 1H), 3.15 (d, 2H, J=7.1 Hz), 3.06 (m, 2H), 2.55 (td, 2H, J=12.0, 2.1 Hz), 0.8-2.0 (m, 16H) ppm. $^{13}C$ NMR (75 MHz, $CDCl_3$): 157.7, 137.7, 128.8, (2C), 127.4, 126.6 (2C), 53.8, 51.4, 49.3, 45.9, 35.8, 33.9, 33.7 (2C), 30.6, 25.6, 25.4, 24.9, 24.8, LCMS: Varian Pursuit 3 $C_{18}$ column, 50×2.0 mm, Gradient method from 100% $H_2O$ with 0.1% TFA, hold for 0.25 min, ramped to 100% MeCN with 0.1% TFA over 5.75 min, hold at 100% MeCN with 0.1% TFA for 1.85 min, ramp back to 100% $H_2O$ with 0.1% over 0.15 min, hold at this for 2 min, flow rate 500 µL/min, room temperature=3.46 min, (ESI positive ion) m/z 330.2 $(M+H)^+$. HPLC: Ace 5 $C_8$ 100×4.6 mm; gradient method from 95% $H_2O$ with 0.1% TFA and 5% MeCN with 0.1% TFA, hold for 3 min, ramped to 100% MeCN with 0.1% TFA over 24 min, ramp back to 95% $H_2O$ with 0.1% TFA and 5% MeCN with 0.1% TFA over 1 min, hold at this for 4 min, flow rate of 1.0 ml/min, rt=7.53 min, 97.8% pure (at 207 nm).

Example 6

The non-clinical safety program has been designed to support single and repeat dose administration in clinical trials with human volunteers. During the initial evaluation of SRI-011381 and analogs, range finding toxicity studies have been performed with mice and rats. In vitro ADME assays and in vivo pharmacokinetics studies in mice have also been completed. Results of the completed studies of SRI-011381 are summarized below.

In Vitro ADME Assay Results: Absorption, distribution, metabolism, and excretion (i.e., ADMET) assays, including metabolic stability assays using human liver microsomes, permeability assays modeling intestinal and blood brain barrier absorption, and drug interaction assays that evaluate cytochrome P450 inhibition, are known in the art and were used to evaluate any of the above compounds and those apparent in view of these compounds. Compounds that show favorable characteristics in these in vitro assays can be further evaluated for oral bioavailability and toxicity (maximum tolerated dose) in vivo.

Numerous compounds were synthesized and screened for activity in efficacy assays and then evaluated in a set of predictive ADMET assays designed to identify the compound with the most favorable drug-like properties. SRI-011381 was found to have characteristics consistent with an orally active drug, with minimal toxicity. The results of these assays are summarized below.

Permeability Assays: PAMPA screens, both for absorption from the gut and through blood brain barrier, were used as a first tier screen for this program. SRI-011381 was evaluated in the double sink assay format and the sum of the permeability coefficients at three pH values (7.4, 6.2, 5.0) was calculated ($P_e$) to be $781×10^{-6}$ cm/s, which is consistent with an orally available compound. The PAMPA-BBB assay resulted in a $P_e$ value greater than 2 ($4.2±2.2×10^{-6}$ cm/s), which also indicated that the compound was likely to penetrate into the brain.

Metabolic Stability: SRI-011381 (1 and 10 µM) was incubated with human liver microsomes (pooled from several donors) and cofactors. Approximately 80% of the compound was unchanged after 60 min indicating that the compound is resistant to hepatic metabolism.

CYP Inhibition: SRI-011381 was screened for CYP inhibition, an indicator of potential drug interactions. Six major CYPs were studied, 1A2, 2B6, 2C9, 2C19, 2D6, 3A4, and SRI-011381 (1 and 10 µM) did not inhibit any CYP activity significantly (>30% reduction in activity). Thus, this compound is unlikely to cause clinically relevant interactions due to effects on co-administered drugs metabolized by these hepatic enzymes.

Example 7

Iterative reporter cell screen assays: Compounds were tested for activation of the TGF-β signaling pathway using two different cell lines produced by stably transfecting cells with the SBE-SEAP reporter gene. These cells lines are TGF-β1 knockout fibroblasts MFB-F11 and mouse NG108-15 neuroblastoma cells. MFB-F11 cells do not produce TGF-β1 and are extremely sensitive to activators of the pathway. Mouse NG108-15 neuroblastoma cells have been used extensively in the field because they can be differentiated into cells with neuron-like properties. Such cells are ideal for assaying TGF-β1 pathway activity in vitro.

Example 8

Bioavailability in Animals

Male Sprague-Dawley rats: Oral bioavailability and BBB passage of test compounds can be measured using, for example male Sprague-Dawley rats. Animal brains are collected from rats at preselected times following administration of a test compound or control and a bioanalytical method, e.g., LC/MS-MS, is used to determine bioavailability by comparing the plasma level curves and the brain concentration of the parent drugs after, e.g., iv. or oral administration. All data from these studies were analyzed using WinNonlin (SCI Software, NC) or a similar software program to determine appropriate pharmacokinetic parameters such as terminal elimination half-life, area under the curve (AUC), maximum concentration in blood and/or plasma after oral administration ($C_{max}$), and other pharmacokinetic parameters as appropriate. These experiments were used to determine the % bioavailability of compounds in plasma and brain and show which compounds are orally active and enter the blood.

SBE-luciferase transgenic mice: Two-month old SBE-luciferase transgenic mice receive different concentrations of a test compound either s.q., ip., or orally by gavage. Compound doses are estimated from in vitro potency, and are typically in the range of from about 1 to about 50 mg/kg body weight. Following administration of the test or control compounds, mice are injected with luciferin ip. At, for example, 2, 8, and 16 hours following injection of luciferin, the mice are imaged to detect bioluminescence as described above. Brains may be harvested 16 hours following test compound injection, and may be divided sagittally. For example, one hemi-brain can be homogenized in luciferase assay buffer for measurement of reporter gene activation, while the other hemi-brain can be frozen at −70° C. for future study, including sectioning into individual brain regions Using this assay, compounds can be tested for the optimal route of injection, half-life, bioactivity, toxicity, efficiency of crossing the blood brain barrier (BBB), accumulation in particular regions of the brain, etc.

Example 9

Toxicity in animals: Toxicity of test compounds can be determined in male and female Sprague-Dawley rats. Dose levels are estimated based on structure-activity analysis, comparison to toxicity of similar drugs, data obtained in vitro, and data obtained in other in vivo studies. A range of doses covering at least one log are typically employed. Three rats/sex/dose group are administered, e.g., a single oral or ip. dose of test compound on Day 1 in an appropriate vehicle (e.g., water, methylcellulose, corn oil). In some examples, three dose levels are evaluated for each test compound, along with an appropriate control (e.g., vehicle). The rats are euthanized and necropsied on Day 5. Endpoints include daily clinical observations, body weights, clinical pathology and gross pathology at necropsy. These studies show whether compounds have unusual toxicity in a particular organ and help establish a maximal therapeutic dose.

Example 10

Excitotoxic injury model: Mice are injured with kainic acid and treated with different test compounds at two concentrations each to determine if they can reduce neurodegeneration and/or microglial activation. Wildtype mice on the FVB/N genetic background (8-weeks-old) are typically injured with kainic acid (Tocris, Ellisville, Mo.) dissolved in PBS and injected subcutaneously (s.q., 20 mg/kg). Seizure activity is scored from 0 to 5, with 0 corresponding to no behavioral changes and 5 corresponding to constant rearing and falling. Only kainate-injected mice reaching at least stage 3 are used for the studies. On day 5 following injury, mice are anesthetized, transcardially perfused with 0.9% saline, and brains harvested and dissected. One hemi-brain may be fixed for 24 hours in 4% paraformaldehyde and cryoprotected in 30% sucrose. Serial coronal sections (40 µm) can be cut with a freezing microtome (Leica, Allendale, N.J.) and stored in cryoprotective medium. One set of sections, representing different levels of the hippocampus, is used for the various stains. The other hemi-brain is dissected into hippocampus, cortex, thalamus, brain stem, and cerebellum. In this manner, the ability of test compounds to reduce neurodegeneration in kainate-injected mice can be assayed.

Example 11

Bioluminescence in vivo imaging in transgenic reporter mice: Bioluminescence has been used to monitor and quantify gene activity repeatedly in the same animal in vivo and to study disease progression in peripheral organs with great success. Although this imaging modality lacks high resolution and cannot be used to localize signals at the cellular level, it is quantitative and can faithfully report gene activation if appropriate fusion gene constructs are used. While initial studies demonstrated the use of this technology for the tracking of luciferase-expressing bacteria or tumor cells in vivo, transgenic mice have been generated that express the Firefly luciferase reporter gene under control the HIV-1 LTR, c-fos, or β-lactoglobulin, or NF-kB promoters/enhancers.

Example 12

Transgenic APP751$^{LonSwe}$ and Prp-tau mice: Transgenic mice that overproduce FAD-mutant human APP reproduce important aspects of AD, including amyloid plaques, neurodegeneration, and cognitive deficits. APP751$^{LonSwe}$ mice which overexpress APP751$^{V717I, K670M/N671L}$ in neurons develop amyloid pathology, neurodegeneration, and cognitive deficits. Mice over-expressing human tau protein associated with familial forms of fronto-temporal dementia (a dementia characterized by extensive tangle formation) develop neurofibrillary tangles similar to the ones observed in AD and suffer from locomotor deficits around 10 months of age. APP751$^{LonSwe}$ and Prp-tau$^{P301L}$ mice can be used to determine the in vivo efficacy of test compounds in treating AD-like diseases.

APP751$^{LonSwe}$ mice have low but detectable levels of Aβ in brain and plasma at 2-months of age, consistently show Aβ deposits at 5-months of age, and exhibit a prominent pathology at 12-months of age. Test compounds can be administered to animals at different stages of disease progression to determine when the compound should be administered for maximum effect, how late in disease progression compounds can be delivered, and the degree of protection afforded by the compounds. Compounds can also be tested for their ability to reverse cognitive deficits.

Prp-tau$^{P301L}$ mice show consistent tau pathology around 6-months of age and develop motor deficits around 9-months of age. Motor function can be tested using a rotarod and cognitive function can be tested using a fear-conditioning paradigm. Both short-term and long-term studies can be performed using APP751$^{LonSwe}$ and Prp-tau$^{P301L}$ mice.

Example 13

Behavioral analysis (Morris Water maze): Mice are trained on a Morris water maze as described by Harris et al., ((2003) *Proc. Natl. Acad. Sci. USA* 100: 10966-10971). Latency, path length, and proximity scores serve as measures of learning. A probe trial was administered 1 and 7 days after training, followed by reversal trials to determine whether the observed results were due to behavioral inflexibility. Swim speeds were also compared.

Half of the males and half of the females were tested in two stages: First, in visual platform training, mice swam to a platform marked with a black and white pole to train the mice to swim to the platform where they were subsequently rescued by the experimenter. Each mouse swam 4-times a day for 3 days. Second, in hidden platform training, 3-D visual cues were added to the walls of the facility, and the black and white pole removed. The mice were placed into the tank and swam around the tank to find the hidden platform (up to 90 seconds), using the cues to triangulate their position. Mice were left on the platform for 10 seconds at the end of the trial to remember the position of the platform (acquisition phase). Each mouse swam 4 times a day for 6 days. Significant differences in acquisition were detected at days 5, 6 and 7 using Student's t test and overall differences were significant with repeated measures ANOVA ($p<0.006$).

Contextual fear conditioning: To assess cognitive function in rTg4510 tau mice a Pavlovian fear-conditioning paradigm can be used in addition to the water maze. Briefly, after receiving a foot shock coupled with an acoustic stimulus in a brightly lit chamber, mice are exposed to the same chamber (contextual memory assessment) or placed in a differently shaped, scented, and lit box (cued memory assessment), e.g., 24 hours or 10 days later. The freezing response of the mice is then quantified. This type of memory test is reliable for assessing deficits in contextual memory and discreet cued memory in mice. It involves a rapidly acquired form of learning, thought to be a model of human explicit memory that appears to involve the hippocampus and that is impaired in AD. An additional advantage of fear conditioning over other spatial memory tasks, such as the Morris water maze, is that it minimally relies on motor skills (i.e. stamina and speed), or vision, and allows cognitive testing of mice with slight motor deficits, as is the case for some transgenic mice.

Example 14

Figure 2B:
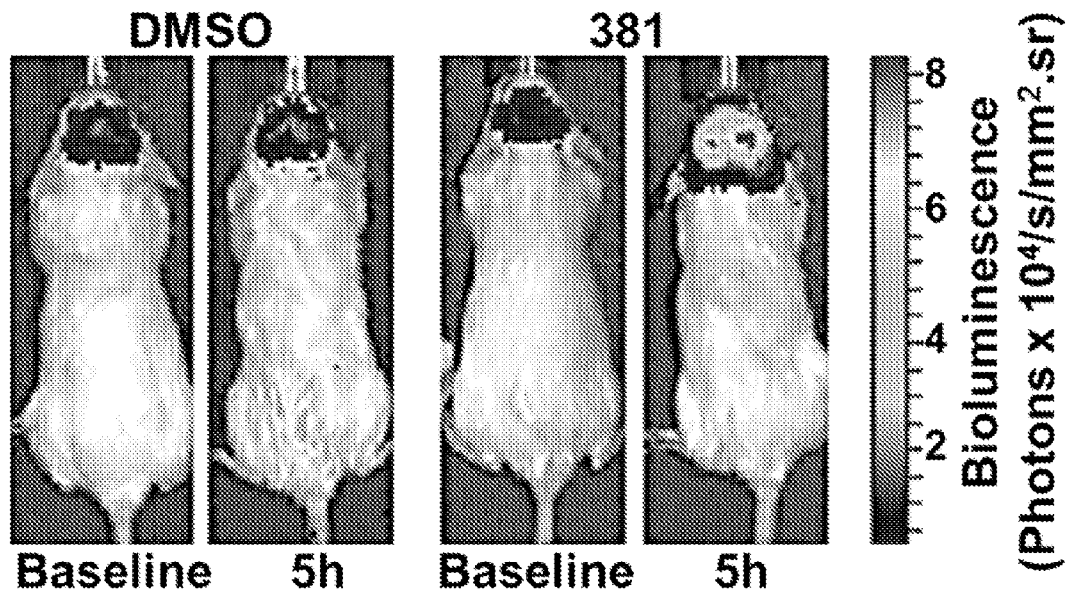
FIG. 2B shows digital images illustrating that compound SRI-011381 (381) activates TGF-β signaling in the brain in the SBE-luc reporter mice.
Figure 2C:
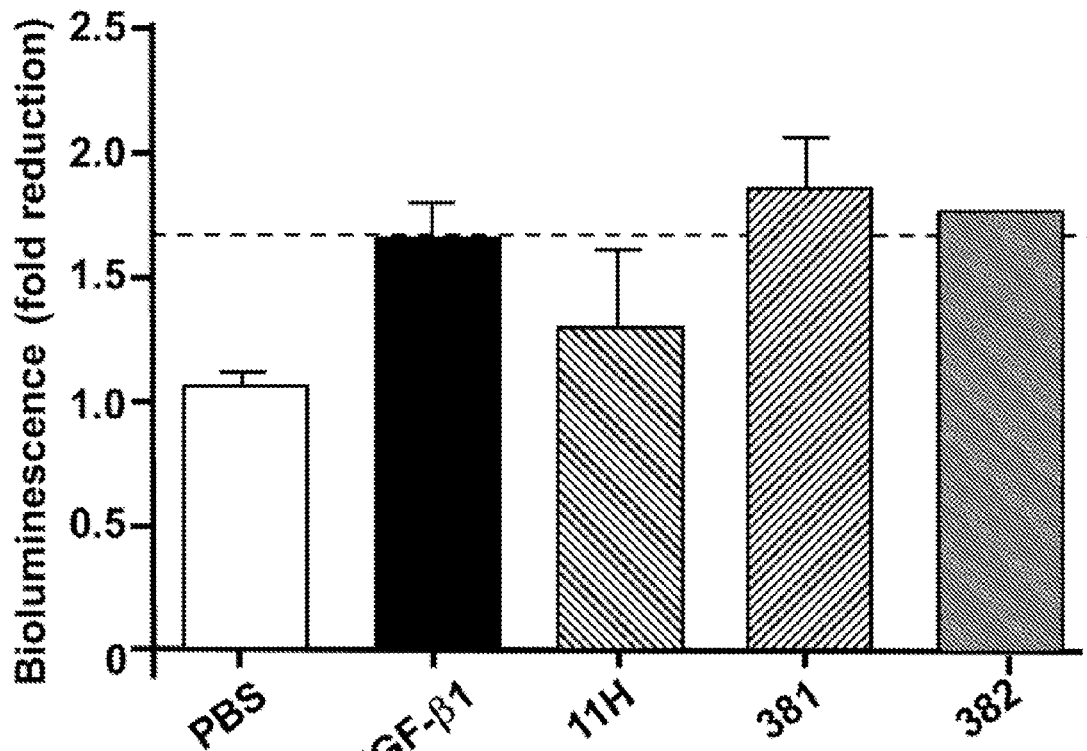
FIG. 2C shows in vivo activity of 11H analogs assessed in SBE-luc reporter mice.

Compound SRI-011381 activates TGF-β reporter gene: Dose-response curves for 11H and two related compounds in this series including the lead compound SRI-011381 (Compound 381) are shown in FIGS. 2A-2D. Compound 381 activates TGF-β signaling in reporter cell line (FIG. 2A). Compound 381 activates TGF-β signaling in reporter mice (FIGS. 2B and 2C).

Figure 2D:
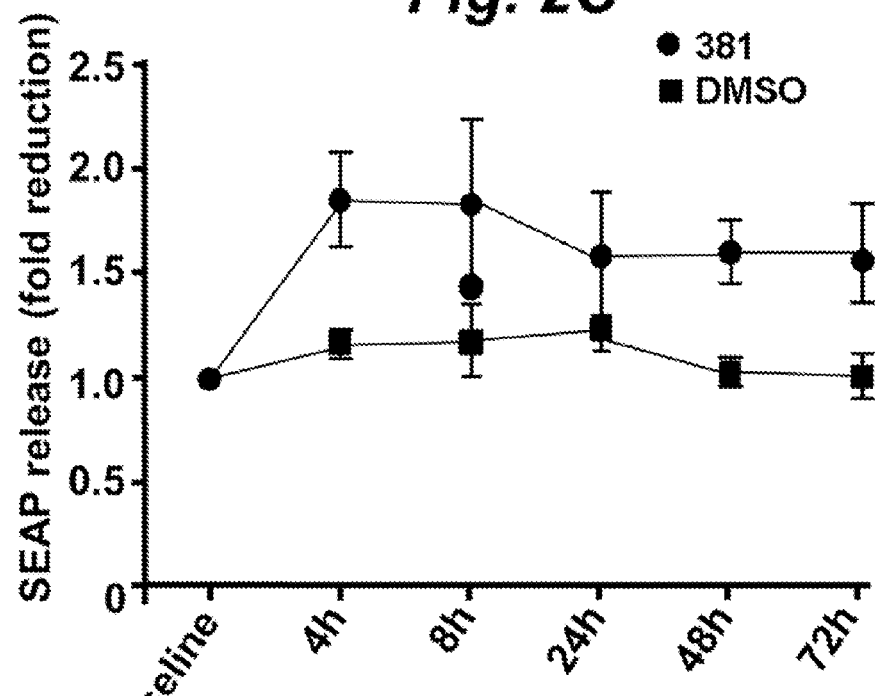
FIG. 2D shows the time course of the bioluminescence signal in the brain. SRI-011381 (381) (30 mg/kg, dissolved in DMSO) was injected (ip.) into the SBE-luc mice and the bioluminescence signal was detected at different time points.

11H and its analog SRI-011381, and salts thereof, were tested in mice in vivo and it was found that they penetrate into the CNS and activate TGF-β signaling in SBE-luciferase bioluminescent reporter mice (as shown in FIGS. 2B-2D). SRI-011381 induces the reporter gene (and thus TGF-β signaling) in vivo in living mice in a time-dependent fashion, as shown in FIG. 2D. 11H analogs were as potent or more potent in vivo than recombinant TGF-β1 in inducing the reporter gene in the CNS, as shown in FIG. 2C. The findings demonstrate that SRI-011381 is a biologically active inducer of TGF-β signaling in cell culture and in vivo.

Example 15

SRI-11381 is neuroprotective in vitro: To determine if the TGF-β-inducing capacity of SRI-011381 would translate into biologically beneficial effects, its neuroprotective potential was tested in B103 rat neuroblastoma cells and primary mouse neurons derived from E16 forebrains. B103 neuroblastoma cells were cultured in 24-well plates and exposed to an oligomeric preparation of Aβ together with compounds or recombinant TGF-β. Cell survival was expressed as the percentage of live cells over total number of the cells, as shown in FIGS. 3A-3H.

Primary hippocampal neurons isolated from E16 CF1 embryos were aged for 6-7 days or 21-22 days, then challenged with 5 μM oligomeric Aβ in the presence or absence of compounds, and assayed for neurotoxicity (cell survival as above) or neuritic dystrophy, respectively. For quantification of neuritic dystrophy, fixed cells were immune-stained with a MAP-2 monoclonal antibody to label dendrites.

FIGS. 3A-3H illustrate that SRI-011381 protects cultured neurons from Aβ toxicity. In experiments summarized in FIGS. 3A-3C. B103 neuroblastoma cells were incubated with Aβ for 24 h. The compounds and TGF-β were added 2 h before Aβ. Following incubations live and dead cells were assessed with calcein-acetoxymethylester (CAM) and SYTOX Orange (Invitrogen), respectively. Under a fluorescence microscope, the live cells showed green color and the nuclei of dead cells exhibited orange fluorescence (as shown in grey-tone in FIG. 3A).

Cell survival was expressed as the percentage of live cells over total number of the cells shown in FIG. 3B. Compounds SRI-011381 (381) and SRI-011382 (382) both provide better protection than TGF-β1, as shown by the percentage of live cells (FIG. 3B) and percentage of rescue (FIG. 3C).

Figures 3G, 3H:
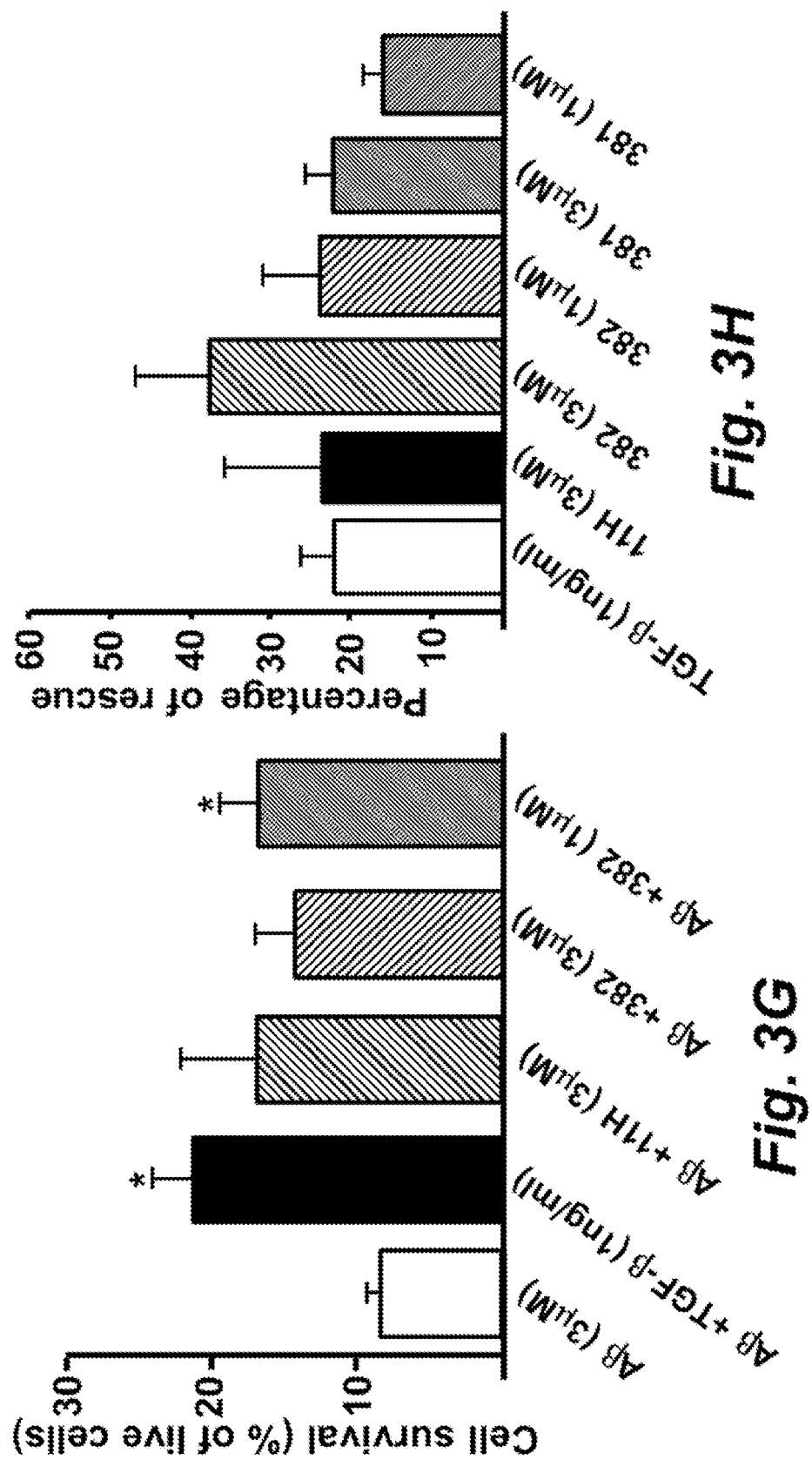

Hippocampal neurons (21-22 DIV) were exposed to 5 μM Aβ for 48 h, fixed and immune-stained for MAP-2 to visualize dendrites (FIGS. 3D-3F). Exposure to Aβ led to increased tortuosity, exhibiting multiple abrupt turns (FIG. 3D). Average numbers of dystrophic neurites per neuron (n=10-12 fields/well) were markedly reduced by compounds 381 and 382, as well as TGF and 11H, as shown in FIG. 3E). Compounds 381 and 382 provided similar rescue as TGF-β1, as shown in FIG. 3F, at the concentrations tested. FIGS. 3G-3H show hippocampal neurons (21-22 DIV) exposed to 5 μM Aβ for 72 h and assessed for cytotoxicity (expressed as % live cells) (FIG. 3G). Compounds 381 and 382 provided similar or better rescue than TGF-β1 (FIG. 3H) at the concentrations tested). The percentage of rescue shown in FIGS. 3C, 3F, and 3H represent summaries of 3 independent experiments. (##, $P<0.01$ vs culture media;*, $P<0.05$, **, $P<0.01$ vs Aβ+PBS; by ANOVA and Tukey's multiple comparison test).

Example 16

SRI-011381 promotes Aβ clearance in cell culture: TGF-β1 promotes Aβ clearance in a microglia cell line. To test whether SRI-011381 has similar properties, mouse J774A.1 macrophages and human macrophages differentiated from THP-1 monocytic cell lines were treated with fibrillar Aβ in the absence or presence of compound (2, 5, or 10 μM) for 24 h. Conditioned medium was harvested and the remaining Aβ that was not phagocytosed by macrophages was quantified by Aβ ELISA. As shown in FIGS. 4A-4D, SRI-011381 and its derivative compounds promoted fibrillar Aβ clearance by macrophages, as demonstrated by the dose-dependent decreases of Aβ in the conditioned medium derived from compound-treated macrophages.

Figure 4A:
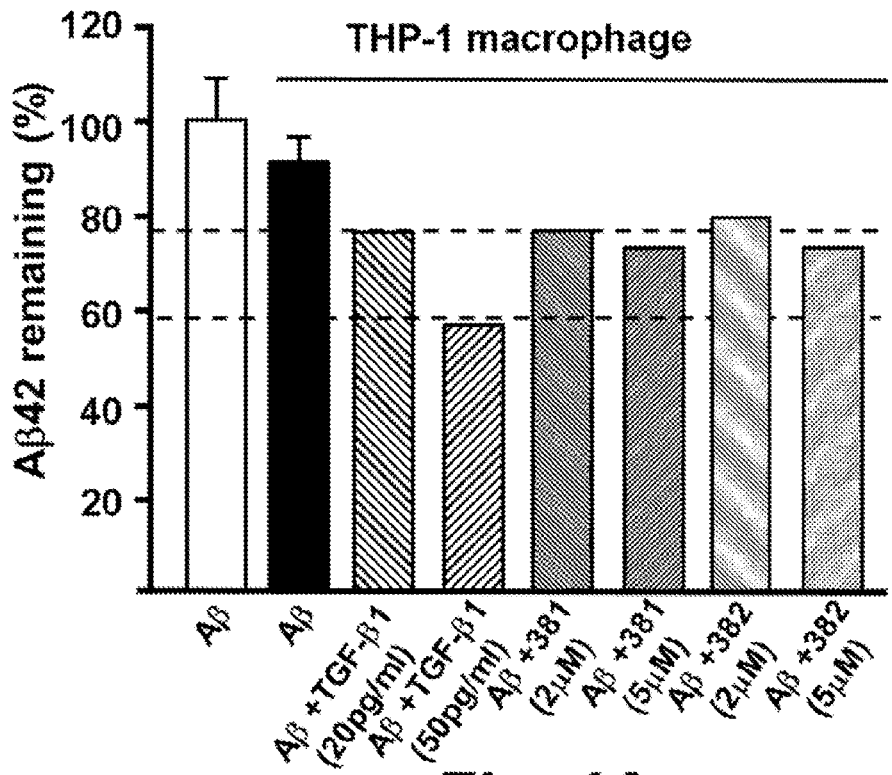
FIGS. 4A and 4B are graphs illustrating clearance of Aβ in which human macrophages differentiated from THP-1 monocytic cell lines (FIG. 4A) and mouse J774A.1 macrophages (FIG. 4B) were incubated with fibrillar Aβ in the absence or presence of a compound at 2 or 5 μM for 24 h.
Figure 4B:
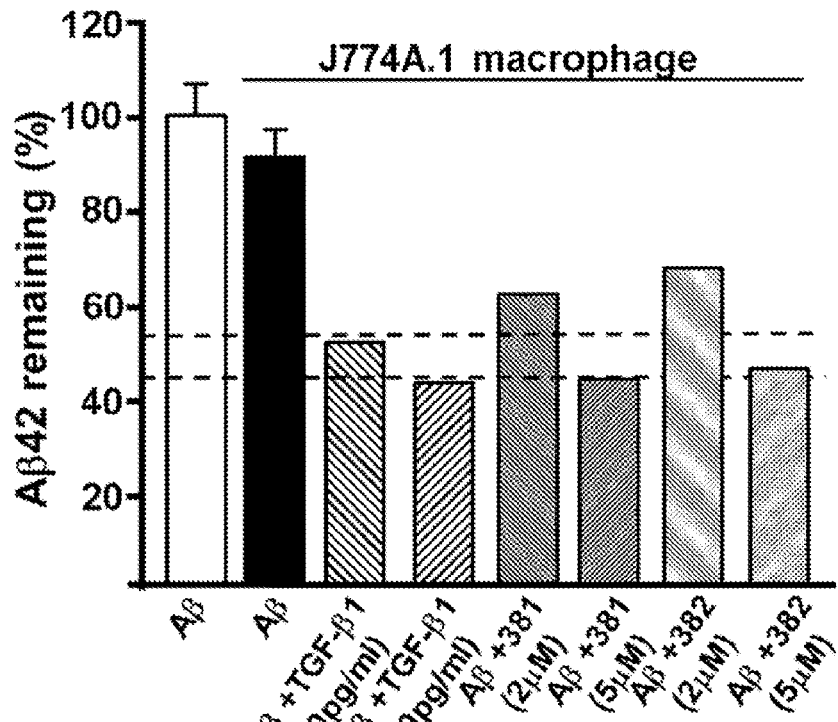
Figure 4C:
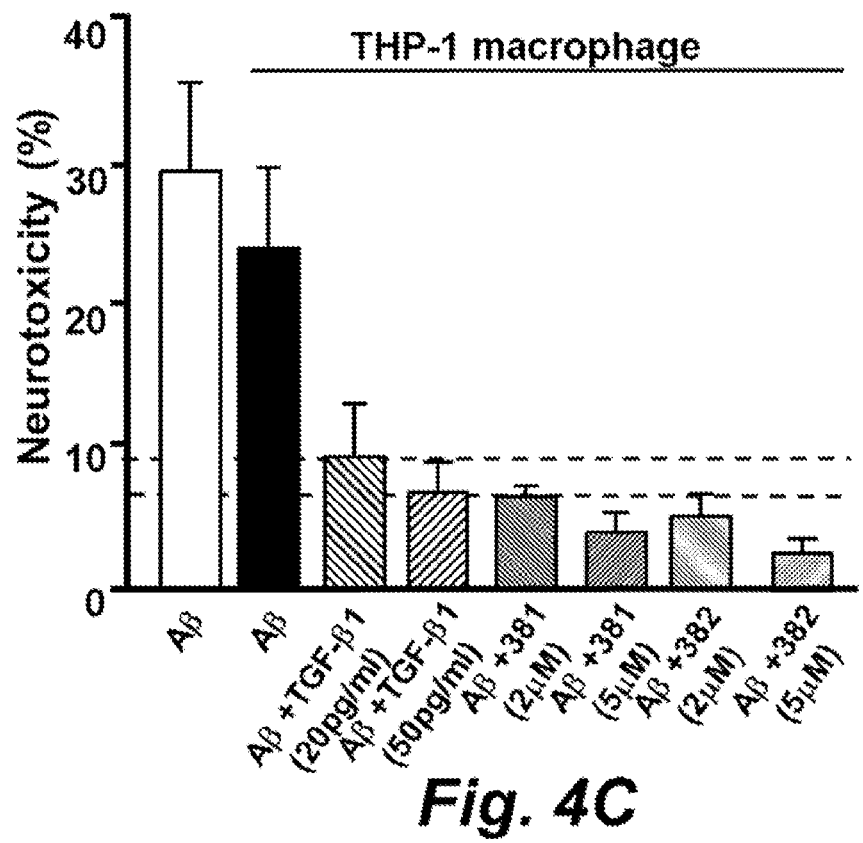
FIGS. 4C and 4D are graphs illustrating neurotoxicity of conditioned medium from THP-1 monocytic cell lines (FIG. 4C) and mouse J774A.1 macrophages (FIG. 4D) added to N2A-APP-Swe cells (mouse Neuro-2A neuroblastoma cells stably expressing Swedish APP695).
Figure 4D:
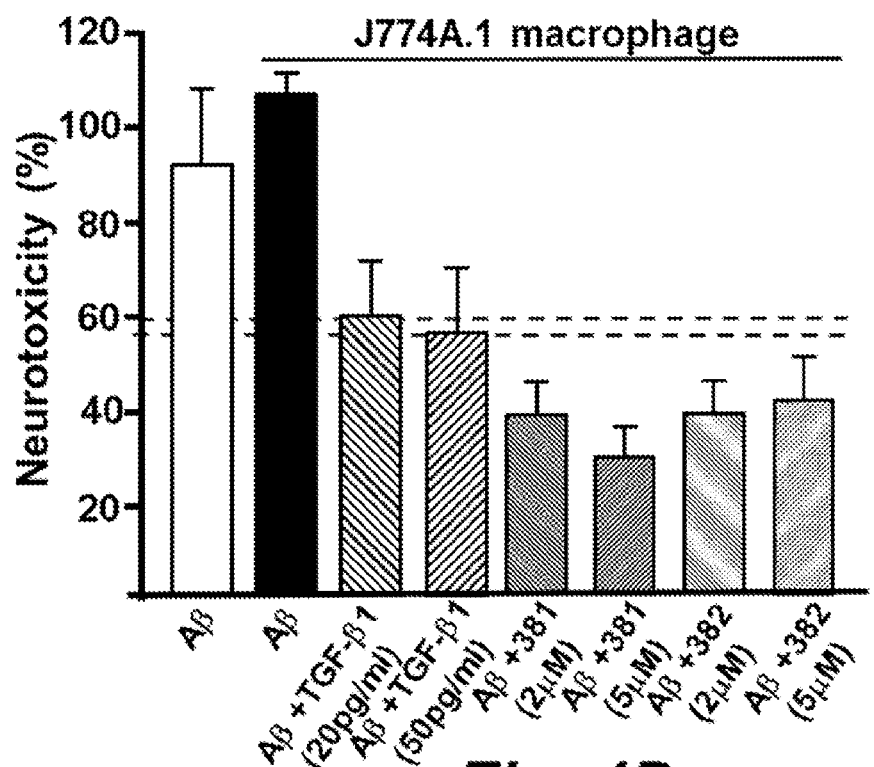

FIGS. 4A and 4B present data from experiments in which human macrophages differentiated from THP-1 monocytic cell lines and mouse J774A.1 macrophages were incubated with fibrillar Aβ in the absence or presence of compound (2 or 5 μM) for 24 h. Conditioned medium was harvested and the remaining Aβ was quantified by Aβ ELISA. The collected medium (FIGS. 4C-4D) was added to N2A-APP-Swe cells (mouse Neuro-2A neuroblastoma cells stably expressing Swedish APP695) and incubated for 24 h. Neurotoxicity was quantified by an MTS Assay.

Example 17

SRI-011381 is neuroprotective in a model of acute neurodegeneration: To study the potential neuroprotective effect of SRI-011381 in vivo, FvB wildtype mice were pre-treated with compound or vehicle for 3 days before excitotoxic injury was induced with kainic acid (10 mg/kg, SQ). Mice continued to receive daily injections of compound until they were sacrificed at day 5 after kainic acid injury. Brains were removed, fixed with paraformaldehyde, sectioned into 40 µM sections using a cryomicrotome and stained with cresyl violet, or immunohistochemical methods. Sections for analysis of synaptophysin, MAP2, and NeuN were subjected to blinded confocal quantitative analysis of neurodegeneration.

Figure 5A:
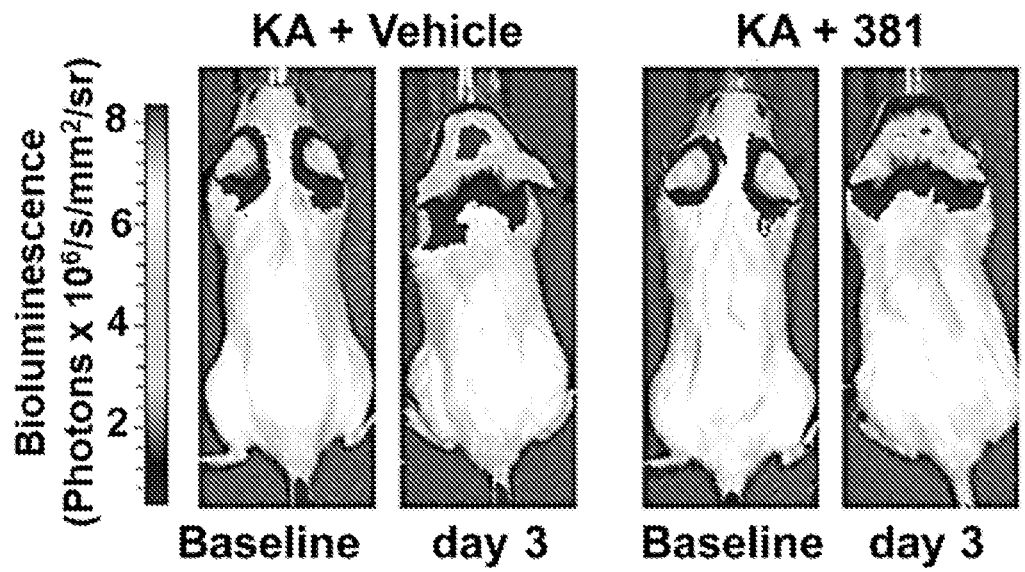

There was a dramatic loss of neuronal (NeuN, cresyl violet, calbindin) synaptic (synaptophysin), and dendritic (MAP2) cell markers and a strong increase in microglial CD68 expression. SRI-011381 reversed or prevented neuronal damage consistently by at least 30% for all neuronal markers, as shown in FIGS. 5A-5E. The drug also reduced CD68 expression by more than 20% (FIG. 5E).

Figure 5B:
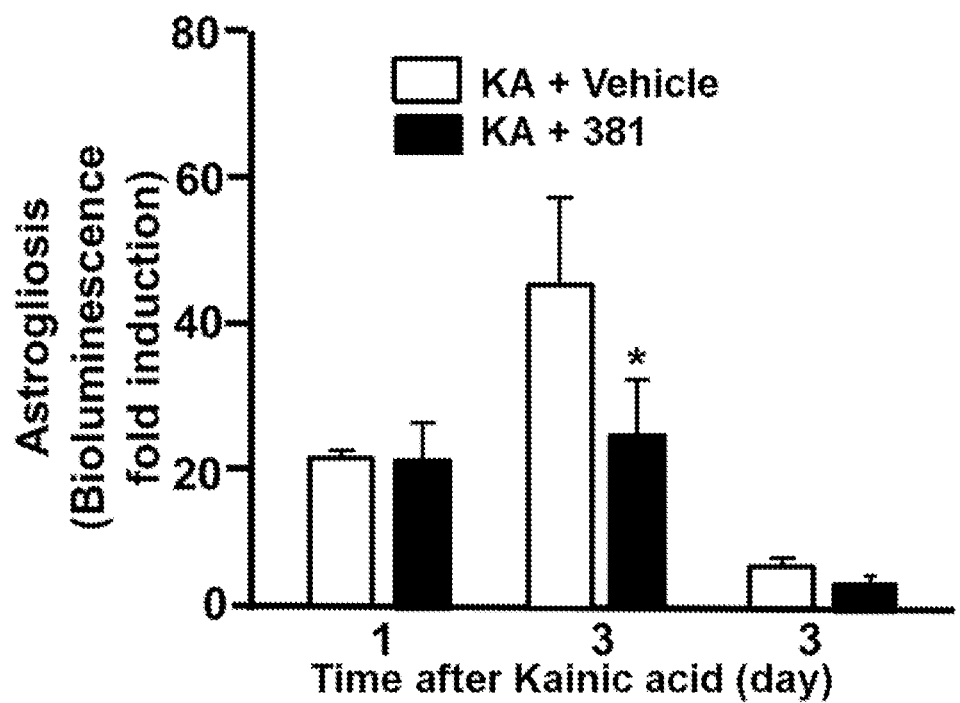

FIGS. 5A-5B show GFAP-luc mice (2-month-old) lesioned with kainic acid (20 mg/kg). Bioluminescence was recorded longitudinally at indicated time points in each mouse. Representative images showing increased bioluminescence signals over the brain after kainic acid injury (left panel) and the reduction by SRI-011381 (381) treatment (right panel) (FIG. 5A). Bioluminescence is expressed as fold induction over baseline, which was measured 1 day before kainic acid administration for each mouse (FIG. 5B). Bars are mean±SEM (n=4-7 mice). The mice were sacrificed 5 days later. Brains were removed, fixed with paraformaldehyde, sectioned and stained with cresyl violet, or immunohistochemical methods. An example of calbindin immunostaining is shown in FIGS. 5C and 5D. Percentage of rescue showed systemic administration of 381 reduces neurodegeneration by 6 markers (FIG. 5E). Bars are mean±SEM (n=4-7 mice/group) and the asterisk signifies P<0.05 by unpaired t test.

Example 18

Drug Product: SRI-011381 has been formulated for administration to animals. The compound was formulated for the earliest studies in 10% DMSO: 15% Solutol:75% sterile water. Subsequently, it was determined that the DMSO could be eliminated and SRI-011381 has been formulated in 15% Solutol:85% sterile water for oral gavage.

Example 19

In Vitro ADME Assay Results: Numerous compounds were synthesized and screened for activity in efficacy assays and then evaluated in a set of predictive ADMET assays designed to identify the compound with the most favorable drug-like properties. SRI-011381 was found to have characteristics consistent with an orally active drug, with minimal toxicity, as follows:

Permeability Assays: PAMPA screens, both for absorption from the gut and through blood brain barrier, were used as a first tier screen for this program. SRI-011381 was evaluated in the double sink assay format and the sum of the permeability coefficients at three pH values (7.4, 6.2, 5.0) was calculated ($P_e$) to be $781 \times 10^{-6}$ cm/s, which is consistent with an orally available compound. The PAMPA-BBB assay resulted in a $P_e$ value greater than 2 ($4.2 \pm 2.2 \times 10^{-6}$ cm/s), which also indicated that the compound was likely to penetrate into the brain.

Metabolic Stability: SRI-011381 (1 and 10 µM) was incubated with human liver microsomes (pooled from several donors) and cofactors. Approximately 80% of the compound was unchanged after 60 min indicating that the compound is resistant to hepatic metabolism. CYP Inhibition: SRI-011381 was screened for CYP inhibition, an indicator of potential drug interactions. Six major CYPs were studied, 1A2, 2B6, 2C9, 2C19, 2D6, 3A4, and SRI-011381 (1 and 10 µM) did not inhibit any CYP activity significantly (>30% reduction in activity). Thus, this compound is unlikely to cause clinically relevant interactions due to effects on co-administered drugs metabolized by these hepatic enzymes.

In Vitro Cytotoxicity: The cytotoxicity of SRI-011381 was determined in primary rat hepatocytes and in VERO cells. The LC50 was >100 µM and 167 µM, respectively. Compared to other compounds in the same structural series, SRI-011381 exhibited lower toxicity in vitro.

Example 20

Figure 7A:
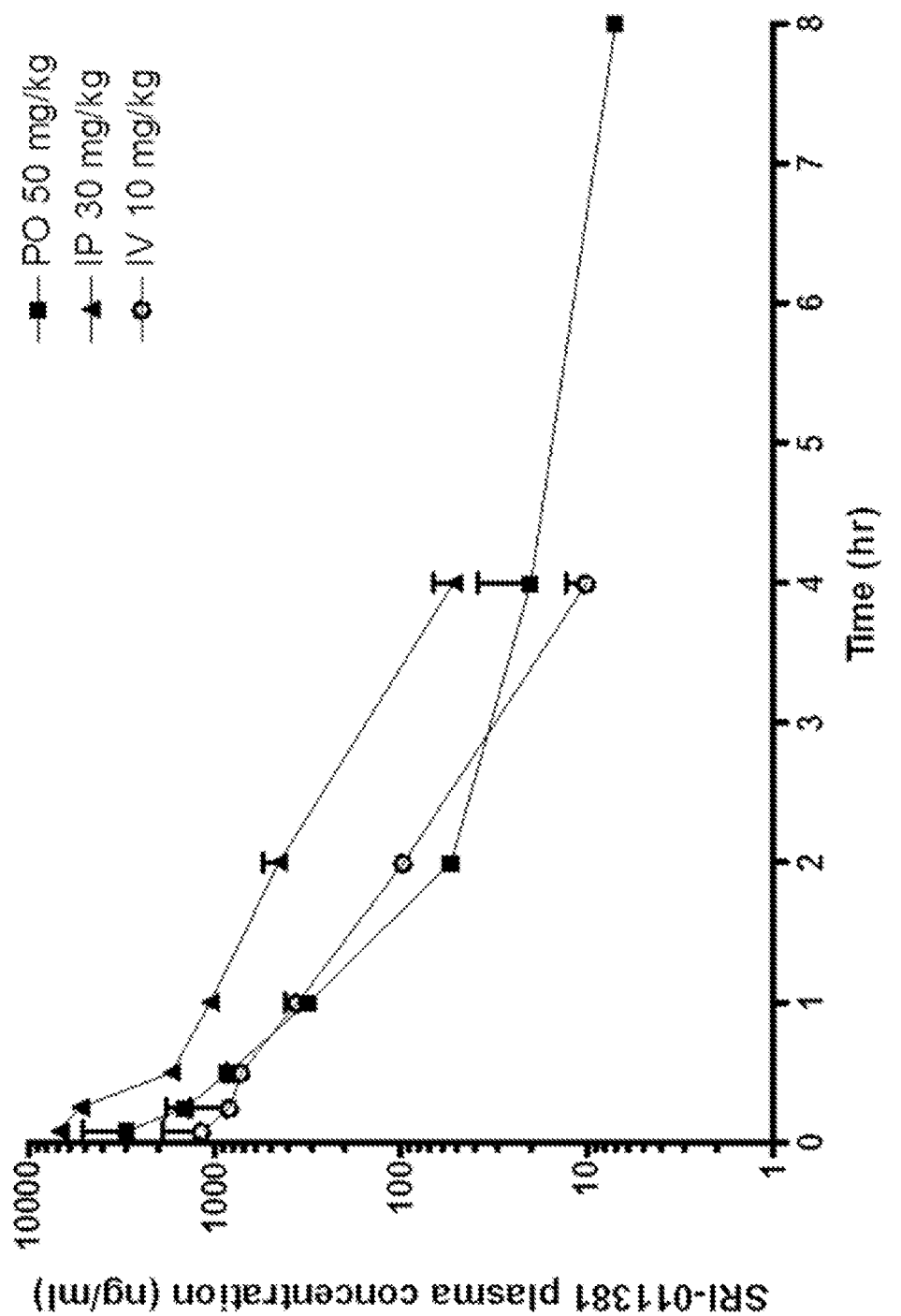
FIG. 7A is a graph showing the plasma concentration-time profile of SRI-011381 (381) after administration to female FVB mice.
Figure 7B:
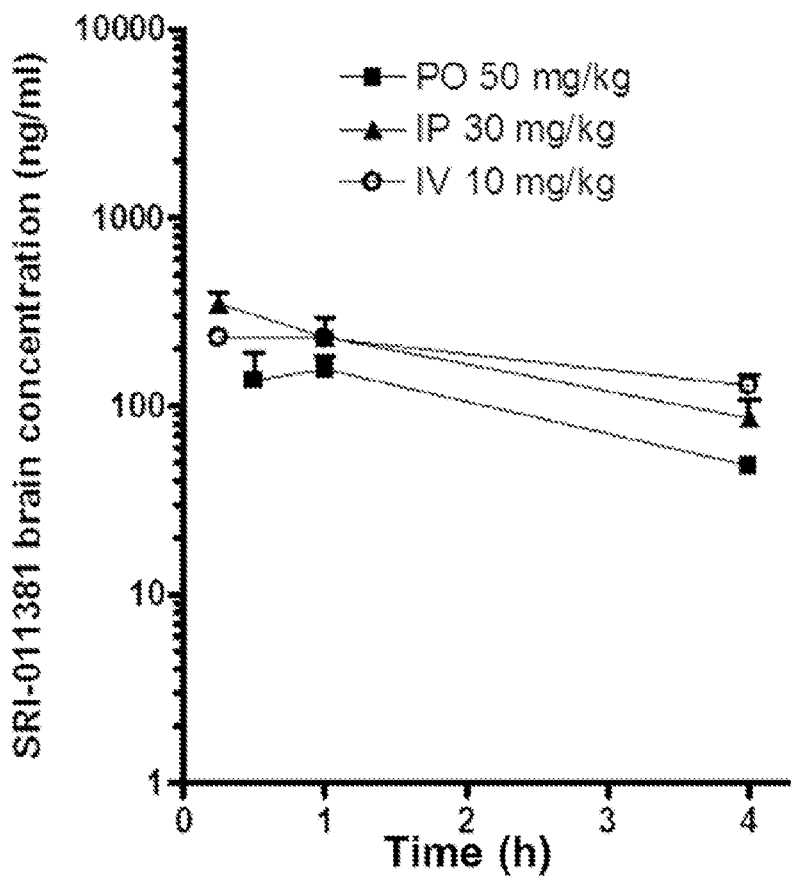
FIG. 7B is a graph showing the brain concentration-time profile of SRI-011381 (381) after administration to female FVB mice.

Pharmacokinetics of SRI-011381 after single intravenous, intraperitoneal, or oral administration in female FVB mice: The objective of this study was to determine the single-dose pharmacokinetics of SRI-011381 in plasma and brain. Female FVB/NJ mice were administered the test article by intravenous (iv, 10 mg/kg), intraperitoneal (ip, 30 mg/kg), and oral gavage (po, 50 mg/kg) dose routes. The compound was formulated in 10% DMSO:15% Solutol:75% sterile water. Plasma and brain were collected at various time points up to 24 h and analyzed by LC/MS for determination of SRI-011381 levels. FIGS. 7A and 7B summarize SRI-011381 levels in plasma and brain, and Tables 4 and 5 list the results of the pharmacokinetic analysis.

Plasma levels after iv administration peaked ($C_{max}$) at 1171±415 ng/ml and showed log-linear decay up to 4 h with a short elimination half-life ($t_{1/2}$) of 0.57 hr. The substantial volume of distribution (V, 7669 ml/kg) and fast rate of clearance (Cl, 9262 ml/hr/kg) suggested SRI-011381 distributed well to tissues and was metabolized rapidly; however, it was not necessarily removed quickly from the body.

The extravascular routes of administration (ip and po) showed higher $C_{max}$ values than iv administration due to higher dose levels and robust absorption. SRI-011381 was rapidly absorbed, especially for the po group, and oral bioavailability (F) was 48%. The ip group had a high F (128%), but this may have been influenced by interindividual variability and/or saturation of clearance mechanisms at higher plasma drug levels. The extravascular estimates of V (about 8-13 l/kg) and Cl (about 9 l/hr/kg) based on F were similar to those after iv administration.

Brain levels were initially lower than plasma, but did not decline as rapidly up to 4 h suggesting SRI-011381 is cleared more slowly than from plasma. As a result, the brain-to-plasma concentration ratios increased to >0.5 at time points after about 0.5 h (iv) and about 1.5 h (po and ip).

Thus, SRI-011381 is absorbed quickly after ip and po administration, but eliminated rapidly from plasma as shown by a short elimination half life ($t_{1/2}$), and large apparent volume of distribution (V) and high clearance (Cl). SRI-011381 entered the brain and was cleared more slowly than from plasma.

TABLE 4

Pharmacokinetic Parameters of SRI-011381 in FVB Mouse Plasma

| Dose route | Dose level (mg/kg) | $C_{max}^a$ (ng/ml) | $T_{max}$ (h) | $AUC_{last}^a$ (hr · ng/ml) | $AUC_{inf}$ (hr · ng/ml) | $t_{1/2}$ (h) | V (ml/kg) | Cl (ml/h/kg) | F (%) |
|---|---|---|---|---|---|---|---|---|---|
| iv | 10 | 1171 ± 415 | 0.083 | 1071 ± 129 | 1080 | 0.57 | 7669 | 9262 | 100 |
| ip | 30 | 6810 ± 720 | 0.083 | 4113 ± 214 | 4157 | 0.59 | 7875 | 9259 | 128 |
| po | 50 | 2950 ± 1236 | 0.167 | 2595 ± 374 | 2605 | 0.97 | 13012 | 9259 | 48 |

$^a$Values are mean ± standard error

TABLE 5

Pharmacokinetic Parameters of SRI-011381 in FVB Mouse Brain

| Dose route | Dose level (mg/kg) | $C_{max}^a$ (ng/ml) | $T_{max}$ (h) | $AUC_{last}^{a,b}$ (hr · ng/ml) | Brain-to-plasma ratio$^c$ |
|---|---|---|---|---|---|
| iv | 10 | 231 ± 106 | 0.25 | 738 ± 89 | 0.28 |
| ip | 30 | 348 ± 33 | 0.25 | 740 ± 32 | 0.07 |
| po | 50 | 157 ± 16 | 1 | 416 ± 33 | 0.19 |

$^a$Values are mean ± standard error
$^b$AUC calculated from 0.25 to 4 h (iv and ip) or 0.5 to 4 h (po)
$^c$Brain-to-plasma concentration ratios were based on values at the brain T Example 21

In Vivo Range Finding Toxicity Studies in Mice and Rats: Dose escalation and 14-day MTD study of SRI-011381 and SRI-011382 in female FVB mice: The objectives of this study were to determine the maximum tolerated dose (MTD) and a no observable adverse effect level (NOAEL) in female FVB mice following a daily oral dose administration for 14 consecutive days. An initial dose escalation was performed with intraperitoneal (ip), oral (po), and intravenous (iv) dose routes for a single-dose MTD of SRI-011381 and SRI-011382. These data were then used to select doses for the efficacy studies performed in FVB mice.

A dose escalation experiment determined a single-dose MTD for intraperitoneal, intravenous, and oral dose administration of SRI-0111381. All animals survived to 48 h at dose levels up to 100, 15, and 200 mg/kg of SRI-011381 for ip, iv, and po dose administration, respectively.

Subsequently, three dose levels (10, 30, and 75 mg/kg) and a vehicle control group were used in the 14-day oral dose administration to determine the MTD and NOAEL based on changes in bodyweight, clinical observations, serum chemistry, hematology and gross organ physiology in 5 female mice per treatment group. For the 14-day oral dose administration, all five mice administered SRI-011381 at 75 mg/kg had adverse signs including hunched posture, hypoactivity and ruffled fur. Mice in the two lower dose groups appeared normal for the duration of the study. The vehicle-only groups appeared normal during the single-dose escalation and 14-day repeat administration. There were no significant differences in body weight or body weight change in any of the treatment groups relative to controls.

There were significant changes in several hematology parameters for mice administered 75 mg/kg SRI-011381 for 14 days. RBCs, hematocrit and hemoglobin were all significantly reduced, while reticulocytes were significantly elevated as a compensation for reduction in RBCs. Absolute WBCs were significantly decreased in the 30 mg/kg group but this change was not dose dependent. Neutrophils (% and absolute) were increased in the 75 mg/kg group. Lymphocytes were decreased in both the 30 and 75 mg/kg group (% and absolute). There were no significant changes in clinical chemistry. The MTD and NOAEL for SRI-011381 were determined to be 75 mg/kg and <30 mg/kg, respectively.

Example 22

Determination of the maximum tolerated dose of SRI-011381 in APP transgenic mice on a C57Bl/6 genetic background: A repeat dose range finding toxicity study was also performed in APP751$^{LonSwe}$ transgenic mice to select doses for evaluation in the efficacy study. Compound SRI-011381 was dissolved in a vehicle containing 15% solutol and 85% water. The formulated compound was administered orally to APP751$^{LonSwe}$ transgenic mice at 0 (vehicle only), 10, 30, 60, or 100 mg/kg of body weight 3 times a week for 2 weeks (this is the regimen intended to be used for the preclinical treatment study in these mice). Five mice (3 male and 2 female) were used for each dosage group. The starting ages of the mice ranged from 4.4 to 6.1 months. Serum and whole blood samples were collected at the end of the study and subjected to clinical chemistry and hematology analysis.

There were no statistically significant changes between treated groups and controls in any of the clinical chemistry or hematology parameters that were studied. In addition, there were no significant differences in body weight. Thus the maximum tolerated dose (MTD) of SRI-011381, administered 3 times per week for 2 weeks to APP751$^{LonSwe}$ mice is greater than 100 mg/kg.

Example 23

7-Day oral gavage dose range finding and toxicokinetic study of SRI-011381 in male and female Sprague Dawley rats: The objective of this study was to determine maximum tolerated dose (MTD), characterize the potential toxicity, and estimate the dose dependence of exposure to SRI-011381 in adult male and female Sprague Dawley rats following daily oral gavage (po) dose administration for 7 consecutive days. The doses studied were 2, 10, and 50 mg/kg, formulated in 15% Solutol/85% sterile water and administered in the volume of 10 ml/kg. Table 6 summarizes the study design.

TABLE 6

Study Design for 7-Day Dose Range Finding Study in Rats

| Group | Treatment | Dose Level (mg/kg) | Dose Conc. (mg/ml) | Total No. of Animals | Plasma Collection Time (1 hr post dose) | Clinical Pathology Collection Time |
|---|---|---|---|---|---|---|
| 1 | Vehicle Control | 0 | 0 | 3M/3F | Day 1 and Day 7 | Day 8 |
| 2 | SRI-011381 | 2 | 0.2 | 3M/3F | Day 1 and Day 7 | Day 8 |
| 3 | SRI-011381 | 10 | 1 | 3M/3F | Day 1 and Day 7 | Day 8 |
| 4 | SRI-011381 | 50 | 5 | 3M/3F | Day 1 and Day 7 | Day 8 |

Species and Strain: Sprague Dawley rat; Route of Administration: Oral (po); Frequency: Daily administration for 7 consecutive days; Dosing Volume: 10 ml/kg; Dose volumes will be calculated based on the animal's most recent body weight; Duration of In-life Phase: 8 days; Endpoints: clinical observations, mortality, body weights, clinical chemistry, hematology, gross pathology, organ weights, histopathology, toxicokinetics.

Figure 8:
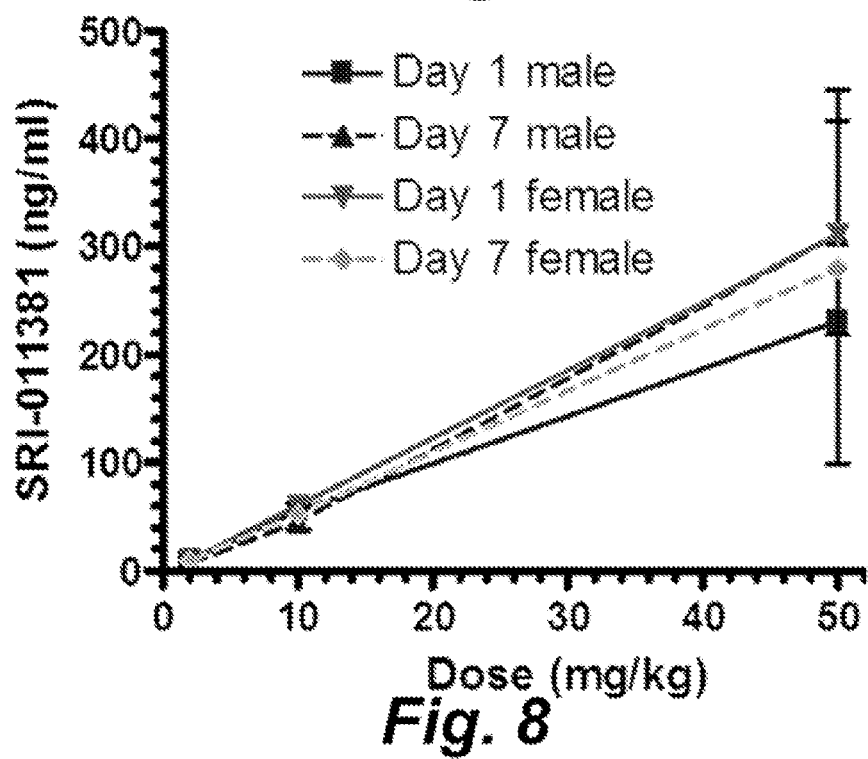
FIG. 8 is a graph showing the plasma concentration of SRI-011381 (381) in male and female Sprague Dawley rats at 1 h post-dose administration on Day 1 and 7 of the 7-day daily dose range finding toxicity study.

FIG. 8 shows that exposure based on plasma collected 1 h after dose administration on Day 1 and 7 increased in a dose dependent fashion. There was no apparent change in exposure after 7 doses compared to the first dose, nor were gender related differences observed.

All animals appeared normal for the duration of the study and there were no statistically significant differences in body weight in any treatment group. Evaluation of the clinical pathology results found no significant changes in any hematology parameters, but alkaline phosphatase (ALP) levels were significantly elevated in all treatment groups in the female rats, though not in males. These increases were minor. LDH was significantly lower in male rats of the high dose group, but there were no significant changes in this parameter in females. Evaluation of the tissues for microscopic changes is in progress and will aid in the interpretation of these clinical chemistry results.

Example 24

SRI-011381 is rapidly absorbed after oral administration to FBV mice with an oral bioavailability of approximately 50%. The apparent volume of distribution suggests extensive tissue distribution. The concentration of SRI-011381 in the brain was lower than plasma levels, but the compound was cleared more slowly from the brain than from plasma, until the brain:plasma ratio was greater than 0.5.

Repeat dose administration of SRI-011381 by oral gavage of 10, 30, and 75 mg/kg for 14 days resulted in significant changes in hematological endpoints, most notably reductions in RBCs, hematocrit and hemoglobin, while reticulocytes were significantly elevated as a compensation for reduction in RBCs. The MTD and NOAEL for SRI-011381 in FBV female mice were determined to be 75 mg/kg and <30 mg/kg, respectively.

The adverse effects on hematology parameters were not observed in the range finding study in male and female APP751$^{Lon,Swe}$ mice. The formulated compound was administered orally at 0 (vehicle only), 10, 30, 60, or 100 mg/kg 3 times a week for 2 weeks, mimicking the dose regimen used in efficacy studies. There were no statistically significant changes between treated groups and controls in any of the clinical chemistry or hematology parameters that were studied. In addition, there were no significant differences in body weight. Thus the maximum tolerated dose (MTD) of SRI-011381, administered 3 times per week for 2 weeks to APP751$^{Lon,Swe}$ mice is greater than 100 mg/kg.

Example 25

Transgenic mouse models over-producing human APP-containing mutations found in families with autosomal dominant AD reproduce important aspects of AD, including amyloid plaques, neurodegeneration, and cognitive deficits. Transgenic mice which overexpress human APP751$^{V717I, K670M/N671L}$ (aka London and Swedish mutations) in neurons under control of a Thy1.2 promoter, specifically Line 41 generated according to Rockenstein et al., (2001) *J. Neurosci. Res.* 66: 573-582, incorporated herein by reference in its entirety, develop amyloid pathology, neurodegeneration, and cognitive deficits (Rockenstein et al. 2001). These mice (short APP751$^{Lon,Swe}$) have been studied by multiple laboratories (Pickford et al. (2008) *J. Clin. Invest.* doi:10.1172/JCI33585; Knowles et al., (2009) *J. Neuroscience* 29: 10627-10637) and have been used as a model for drug development.

Evaluation of SRI-011381 in APP751$^{Lon,Swe}$-Transgenic Mouse Model: This study was to demonstrate oral availability of SRI-011381 in brains of APP751$^{Lon,Swe}$ mice and to demonstrate that non-toxic doses of SRI-011381 reduce neurodegeneration, and improve cognition in APP751$^{Lon,Swe}$ transgenic mice at an age when they already show AD-like pathology.

Compound SRI-011381 was dissolved in a vehicle containing 15% solutol and 85% water. The formulated compound was administered orally to APP751$^{Lon,Swe}$ transgenic mice or littermate non-transgenic controls (male, 6.5-7.5 months of age) at 0 (vehicle only), 10, 30 mg/kg of body weight 3 times per week for 10 weeks (n=7-11 mice per group). Behavioral studies started at this point. Oral gavage of the compound continued throughout the course of the studies until the mice were sacrificed 17 weeks after treatment had been initiated (thus mice were treated for roughly 4 months total before they were sacrificed). Plasma samples were collected for future proteomic assays. One hemibrain was fixed in 4% PFA for 48 h and kept in 2% PFA at 4° C. for neuropathologcial analysis. The other hemibrain was snap frozen. Both the serum and frozen brain samples were placed into −80° C. freezer for long-term storage.

Figure 9B:
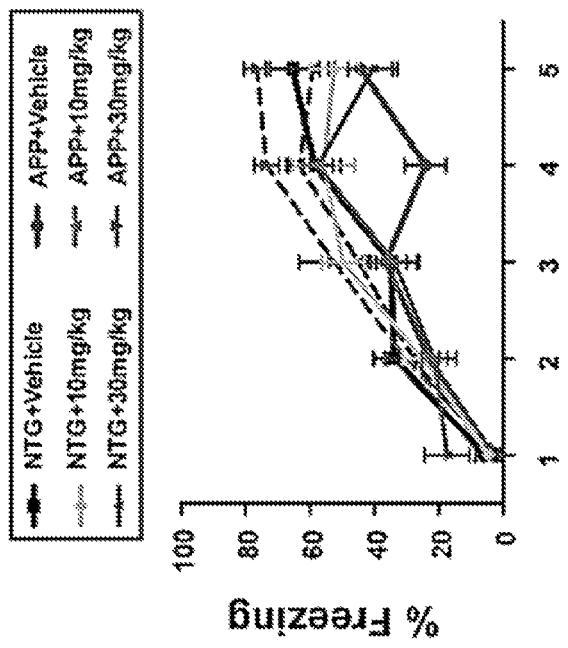
FIGS. 9A-9D illustrate that compound SRI-011381 (381) improves cognition in APP751$^{Lon,Swe}$ transgenic mice
Figure 9D:
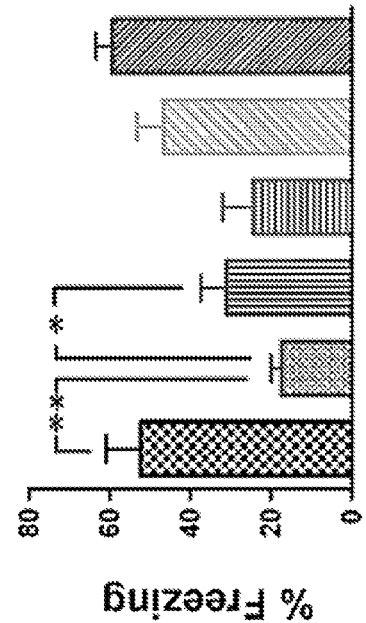
Figure 9A:
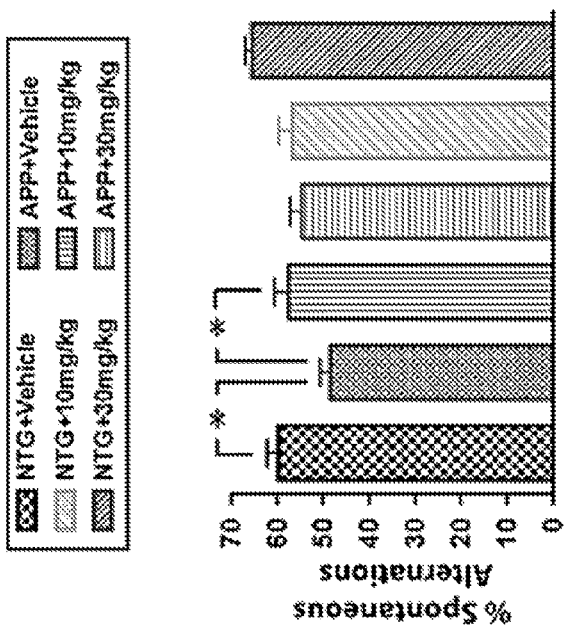

APP751$^{Lon,Swe}$ mice were tested in a Y-maze and showed impairment in working memory (FIG. 9A). SRI-011381 at 10 mg/kg produced a robust >50% rescue of this deficit (FIG. 9A). In fact, SRI-011381 treated APP751$^{Lon,Swe}$ mice were not significantly impaired compared with littermate non-transgenic controls treated with vehicle (FIG. 9A).

Thus, FIGS. 9A-9D show that compound SRI-011381 improves cognition in APP751$^{Lon,Swe}$ transgenic mice. Male APP751$^{Lon,Swe}$ transgenic (APP) mice and their non-transgenic (NTG) littermates (n=7-11 mice per group, age 6.5-7.5 months) each were randomly assigned to three groups and received treatment with vehicle, 10 mg/kg or 30 mg/kg (delivered by oral gavage). After 10 weeks of treatment, cognitive function was assessed using Y-maze (FIG. 9-6A) and contextual fear conditioning test (FIG. 9D). In the Y-maze test for working memory, APP transgenic mice (APP+vehicle) showed less spontaneous alternations than NTG mice (NTG+vehicle), which were improved by 381 treatments (FIG. 9A).

Figure 9C:
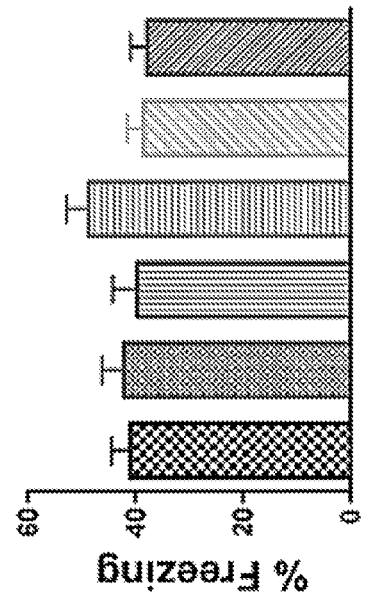

In FIGS. 9B-9D, in the fear-conditioning test, no significant statistical difference was apparent in baseline freezing (FIG. 9A), however, APP transgenic (APP+vehicle) froze less in response to the tone alone (tone 4), while compound 381 (at both 10 or 30 mg/kg) treated APP mice showed significant increase in freezing, to the levels similar to the NTG (FIG. 9B). No freezing difference was apparent for the tone memory (FIG. 9C). APP mice (APP+vehicle) showed significantly impaired context memory compared to NTG (NTG+vehicle), which was significantly improved by compound 381 (10 mg/kg) treatment (D). **, P<0.01; *, P<0.05, by two way ANOVA and Bonferroni's multiple comparison test.

Mice were then tested in a contextual fear-conditioning paradigm using APP751$^{Lon,Swe}$ mice deficient in contextual memory. There were no significant differences in baseline freezing in any of the groups (FIG. 9B) but a significant impairment in learning of the tone response (FIG. 9B) in APP751$^{Lon,Swe}$ mice was observed. This deficit was completely absent in APP751$^{Lon,Swe}$ mice treated with SRI-011381 (381) at 10 or 30 mg/kg (FIG. 9B) supporting the notion that the compound may be able to delay or rescue working memory deficits in these mice. In contrast, no significant differences were seen between any of the six study groups of mice for cued memory to the tone (FIG. 9C).

Lastly, APP751$^{Lon,Swe}$ mice showed a prominent impairment in contextual memory (FIG. 9D). Again, SRI-011381 (381) showed greater than 50% rescue of this deficit. This beneficial effect was more prominent with the lower dose of the compound. Together, these behavioral studies show that SRI-011381 administered orally is capable of delaying or rescuing memory deficits present in APP751$^{Lon,Swe}$ mice.

To determine the effects of SRI-011381 (381) treatment on AD-like pathology brains from APP751$^{Lon,Swe}$ transgenic and non-transgenic littermate control mice treated with vehicle, 10 mg/kg, or 30 mg/kg of compound were sectioned into 40 μm free-floating sections with a vibratome. Brain sections were stained with antibodies against Aβ, phosphorylated tau (PHF1), calbindin, microtubule associated protein2 (MAP2), synaptophysin (SY38), NeuN, and Iba1. In addition, hippocampus and neocortex from one hemibrain from APP751$^{Lon,Swe}$ mice were homogenized with guanidine, and levels of Aβ1-42 and Afβ1-x were measured by ELISA.

Figure 10A:
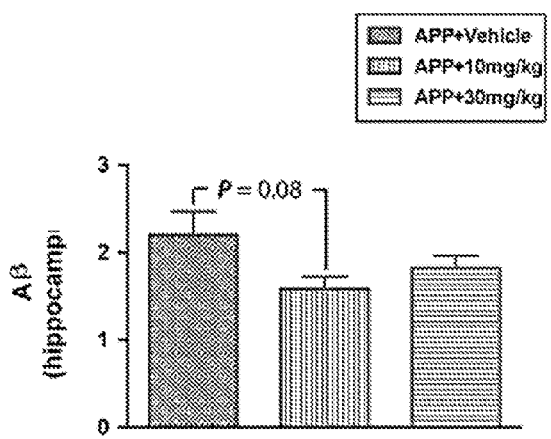
FIGS. 10A-10F show the effects of compound SRI-011381 (381) on Aβ levels in APP751$^{Lon,Swe}$ transgenic mice. After behavioral tests, the mice were sacrificed. For each mouse, one-hemibrain was fixed with paraformaldehyde, sectioned and stained with immunohistochemical methods (FIGS. 10A and 10B). The other hemibrain was snap frozen and stored at −80° C. for biochemical analysis (FIGS. 10C-10E).
Figure 10B:
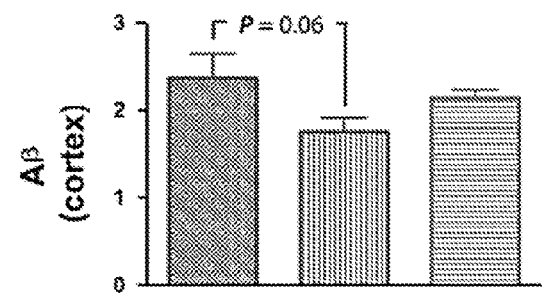

A trend was seen towards lower levels of Aβ immunoreactivity in hippocampus and cortex of compound treated APP751$^{Lon,Swe}$ mice that nearly achieved statistical significance (FIGS. 10A and 10B). Similarly, non-significant trends towards lower Aβ levels were seen as measured by ELISA in hippocampus and cortex in compound treated mice (FIGS. 10C-10F).

Figure 10C:
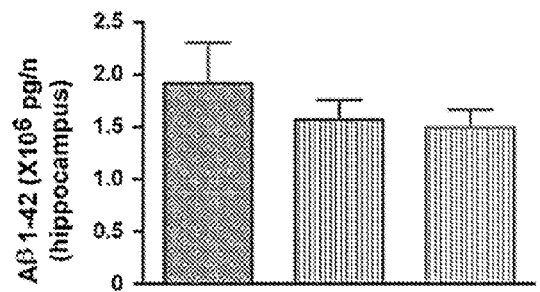
Figure 10D:
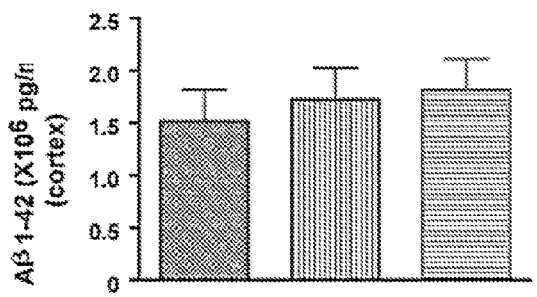
Figure 10E:
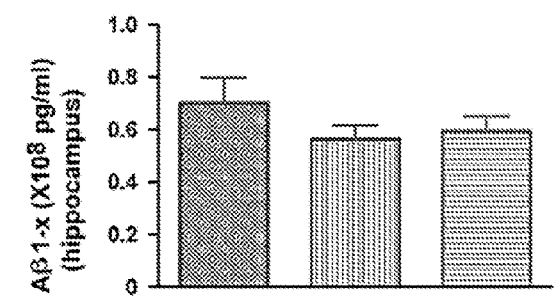
Figure 10F:
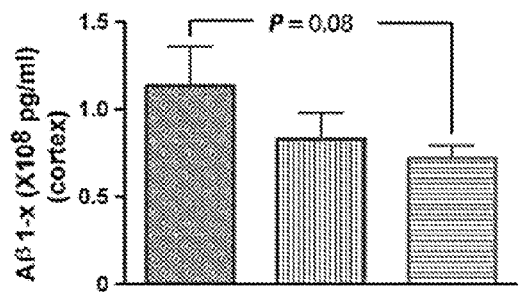

After behavioral tests, the mice were sacrificed. For each mouse, one-hemibrain was fixed with paraformaldehyde, sectioned and stained with immunohistochemical methods (FIGS. 10A and 10B). The other hemibrain was snap frozen and stored at −80° C. for biochemical analysis (FIG. 10C-10E). As shown in FIGS. 10A and 10B, brain sections were immune-stained for Aβ, which was quantified by immunoreactivity.

As shown in FIGS. 10C-10E, hippocampus and cortex were dissected from each hemibrain and subjected to homogenization with 5M guanidine extraction, followed by ELISA for Aβ1-42 and Aβ1-x. Bars are mean±SEM (n=7-11 mice/group). P values were obtained by ANOVA and Bonferroni's multiple comparison test.

Example 26

Compound SRI-011381 reduces neurodegeneration in APP751$^{Lon,Swe}$ transgenic mice: In addition, SRI-011381 showed prominent beneficial effects on multiple parameters of neurodegeneration in APP751$^{Lon,Swe}$ mice (FIGS. 11A-11F). These mice showed significantly lower levels of calbindin, synaptophysin, MAP-2 and NeuN but when treated with compound, showed significantly higher levels of these neuronal markers consistent with delay or reversal of degeneration (FIGS. 11B-11F). APP751$^{Lon,Swe}$ mice also showed a twofold increase in expression of PHF1, a marker of abnormal tau phosphorylation, and this increase was almost completely absent in compound treated mice (FIG. 11A). Interestingly, compound SRI-011381 did not significantly change the level of Iba1, a marker of microglial activation, but appeared to alter the morphology of microglia.

Brain sections were immune-stained for neurodegeneration markers PHF1 (FIG. 11), calbindin (FIG. 11B), MAP2 (FIG. 11C) and Synaptophysin (SY38, FIG. 11E), which were quantified as immunoreactivity (arbitrary units, AU) in the hippocampus (FIGS. 11A-11E) and cortex (FIG. 11F). Bars are mean±SEM in (FIGS. 11A-11D), **, P<0.01; *, P<0.05, by two-way ANOVA and Bonferroni's multiple comparison test. The percentage of rescue was calculated for each marker from both hippocampus (FIG. 11E) and cortex (FIG. 11F). Accordingly, the results demonstrate that oral administration of SRI-011381 three times per week for 3-4 months delays or reduces neurodegeneration and cognitive impairments in APP751$^{Lon,Swe}$ mice with pre-existing AD-like pathology.

Thus, treatment of APP751$^{LonSwe}$ mice with two dose levels of SRI-011381 resulted in a marked amelioration of neurodegeneration over the 4-month-period of treatment in mice with pre-existing amyloid pathology.

Example 27

Permeability PAMPA: The PAMPA assay was used to predict oral bioavailability of compounds. The PAMPA determines the permeability of compounds across a biological membrane using a synthetic lipid membrane and detection by UV absorbance. Since this is not a cellular assay it does not indicate whether the compounds are substrates for transporter proteins, e.g. Pgp; however, it does correlate well with the ability of a drug to be absorbed after oral administration. The PAMPA-BBB assay was performed, to predict permeability to the blood brain barrier, as an aqueous assay and as a co-solvent assay. In this assay the composition of the lipid membrane included brain-derived lipids, mimicking the BBB membrane.

Example 28

Permeability: Caco-2 cells: Permeability across Caco-2 cell monolayers was used as the in vitro method to predict absorption of drug candidates. In this assay, the permeability coefficient, P, of a drug across a monolayer of Caco-2 cells from the apical to basolateral side of the cells (an in vitro model of the intestine) is measured and has been shown to correlate with the oral absorption of drugs that are neither subject to first-pass metabolism nor substrates for transporter proteins. A higher rate of flux from the basal to the apical side compared to apical to basal suggests unfavorable membrane transport properties are likely to limit drug bioavailability.

Example 29

Drug Interactions (GYP inhibition): GYPs are major enzymes involved in drug metabolism and this assay is used to screen the inhibitory potential of test compounds on in vitro CYP activity, and help predict potential drug interactions due to inhibition of metabolism of one drug by another. This assay was performed by incubating test compounds with human liver microsomes and model CYP substrates (i.e., phenacetin (CYP1A2), bupropion (CYP2B6), diclofenac (CYP2C9), mephenytoin (CYP2C19), bufuralol (CYP2D6), testosterone (CYP3A4), and midazolam (CYP3A4)). Control incubations containing compounds known to inhibit specific CYPs were also included and incubated in the same manner as the test compounds (i.e., furafylline (CYP1A2), thioTEPA (CYP2B6), sulfaphenazole (CYP2C9), tranylcypromine (CYP2C19), quinidine (CYP2D6), and ketoconazole (CYP3A4)). The data is expressed as '% of control', where the controls consist of the model substrates incubated with microsomes (no test compounds or inhibitors). CYP inhibition was observed for some of the test compounds at 10 mM, but inhibition was not observed at the lower concentration.

Example 30

B103 neuroblastoma cells: B103 neuroblastoma cells were cultured in Dulbecco's modified Eagle's medium containing 10% fetal calf serum and 1% v/v penicillin/streptomycin (Invitrogen) in a 5% $CO_2$: 95% air atmosphere. $10^4$ cells/well were seeded onto 24 well plates and cultured for 24 h before Aβ was added. The compounds and TGF-β were added 2 h before Aβ. Following a 24 h incubation with Aβ, live and dead cells were assessed using calcein-acetoxymethylester (CAM) and SYTOX Orange (Invitrogen), respectively. AM is a membrane-permeable, fluorogenic esterase substrate that is hydrolyzed intracellularly to a green fluorescent product (calcein) in live cells. SYTOX Orange is a high-affinity nucleic acid stain that easily penetrates cells with compromised plasma membranes and yet will not cross the membranes of live cells. After incubation with SYTOX Orange, the nucleic acids of dead cells fluoresce bright orange. The live and dead cells were observed under an invert fluorescence microscope (Olympus), where the live cells showed green color and the nuclei of dead cells exhibited orange fluorescence. Five fields were randomly selected from each well and the cell numbers were analyzed by ImageJ (NIH) in a blinded fashion. Cell survival was expressed as the percentage of live cells over total number of the cells, as shown in FIGS. 12A-12E.

Example 31

SRI-011381 (compound 381) had the following in vivo properties:
1) Brain to Plasma concentration ratio ($C_{max}$ brain/$C_{max}$ plasma) >0.5
   Ratio at 4 h: 1.65, ip; 0.89 p.o.; 12.5 iv.
2) Oral bioavailability (AUC oral/AUC iv) >10%
   48%
3) No significant (p=0.05) toxicity, compared to vehicle control, after 14 days; as measured by clinical endpoints (body weight), clinical pathology, gross pathology at necropsy.
   Maximum tolerated dose, 30 mg/kg, no adverse effects at 14 days
4) Maximum tolerated dose of compound reduces pathology (as measured by markers of synaptic loss-synaptophysin, neurodegeneration-Map-2, NeuN and microglial activation-CD68) in an excitotoxicity model in vivo by at least 30%. One third of maximum tolerated dose reduced:
   Synaptophysin, 67.5% MAP-2, 37.4%
   NeuN, 36.9%
   Cresyl violet, 54.0%
   D68, 22.5%

Example 32

Brain to Plasma Concentration ratio-Brain Penetration: 11H analog SRI-011381 (381) and SRI-011382 were tested in mice in vivo and shown to be bioavailable in the CNS and activate TGF-β signaling in SBE-luciferase bioluminescent reporter mice (T182-103F mice). Notably, all these analogs are more active in vivo than their original core structures. In spite of their relatively higher clogP (although within Lipinski's rules) and low in vitro activity evidence was obtained that our cell-based assay can identify bioactive drugs with CNS activity.

Figure 12G:
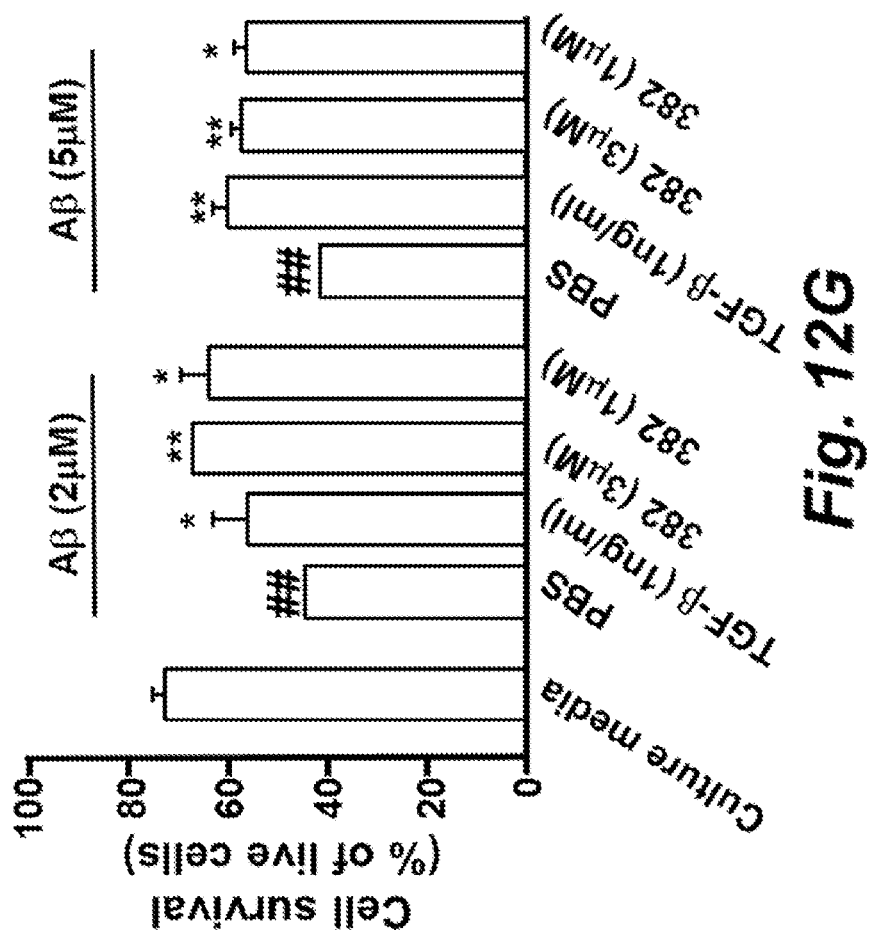
Figure 12F:
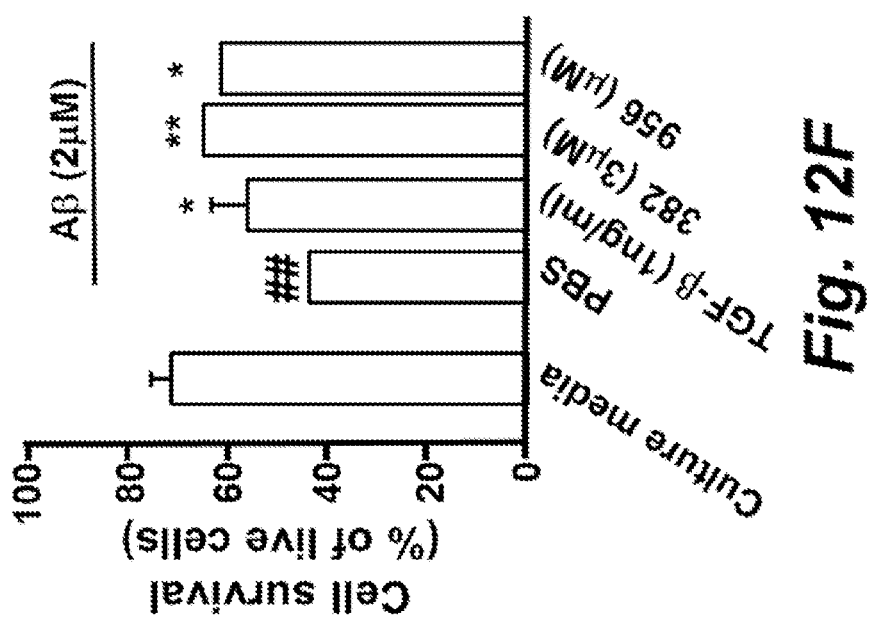
Figure 13E:
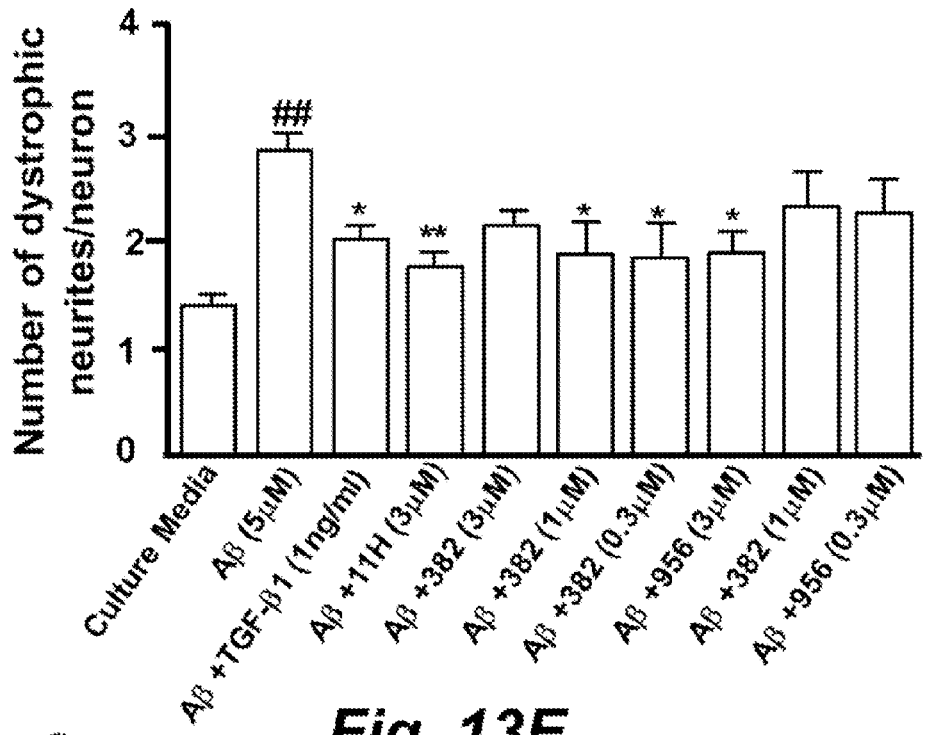
Figure 13F:
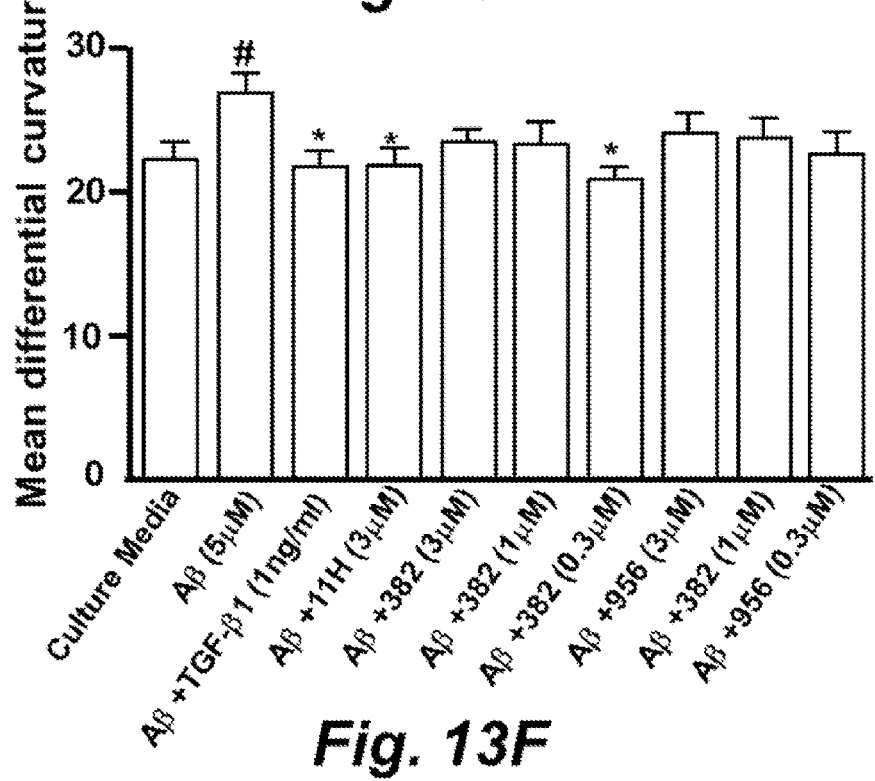
Figure 14A:
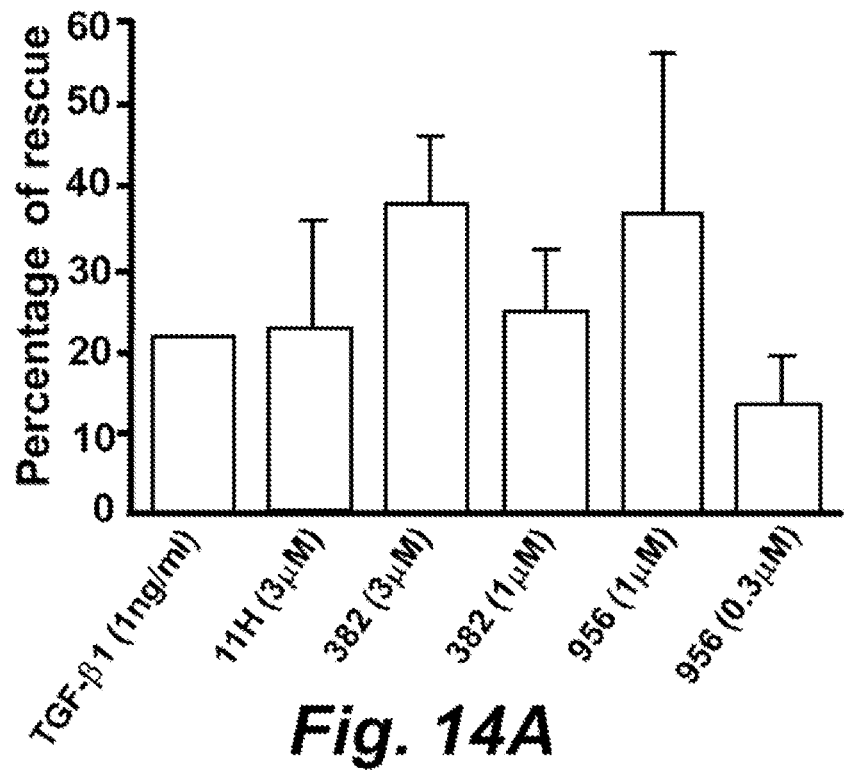
FIGS. 14A-14D are a series of graphs illustrating the percentage of rescue by compounds 382 and 956, compared with TGF-β and 11H (HCl salt). Data were calculated from primary neuron neurotoxicity assay (FIG. 14A), B103 live/dead cell assay (FIG. 14B), primary neuron dystrophic neurite counting (FIG. 14C), and curvature measurement (FIG. 14D).
Figure 14B:
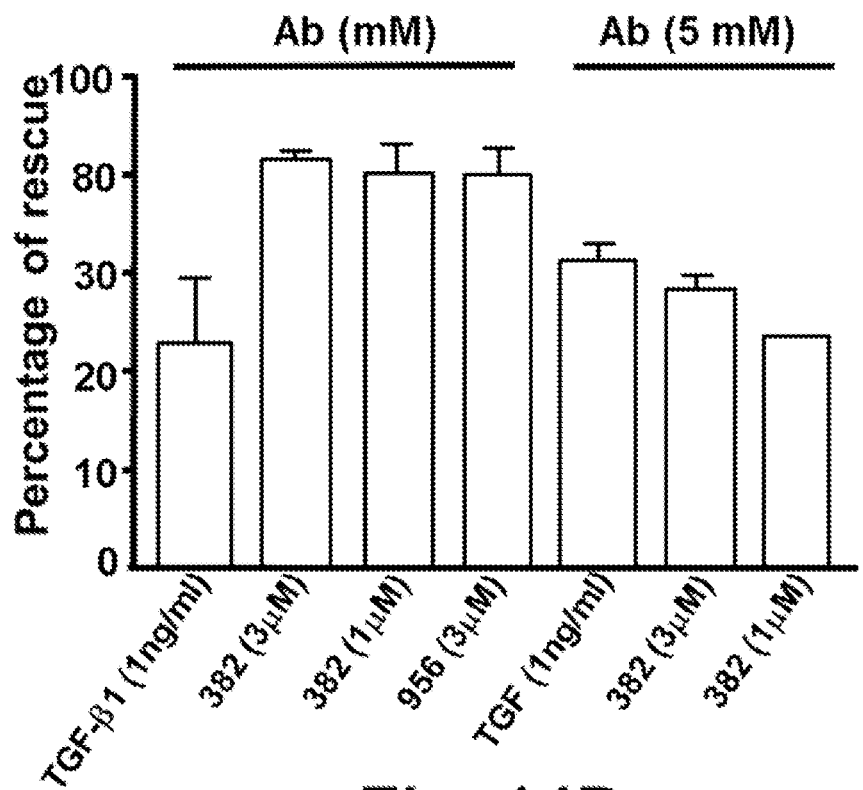
Figure 14C:
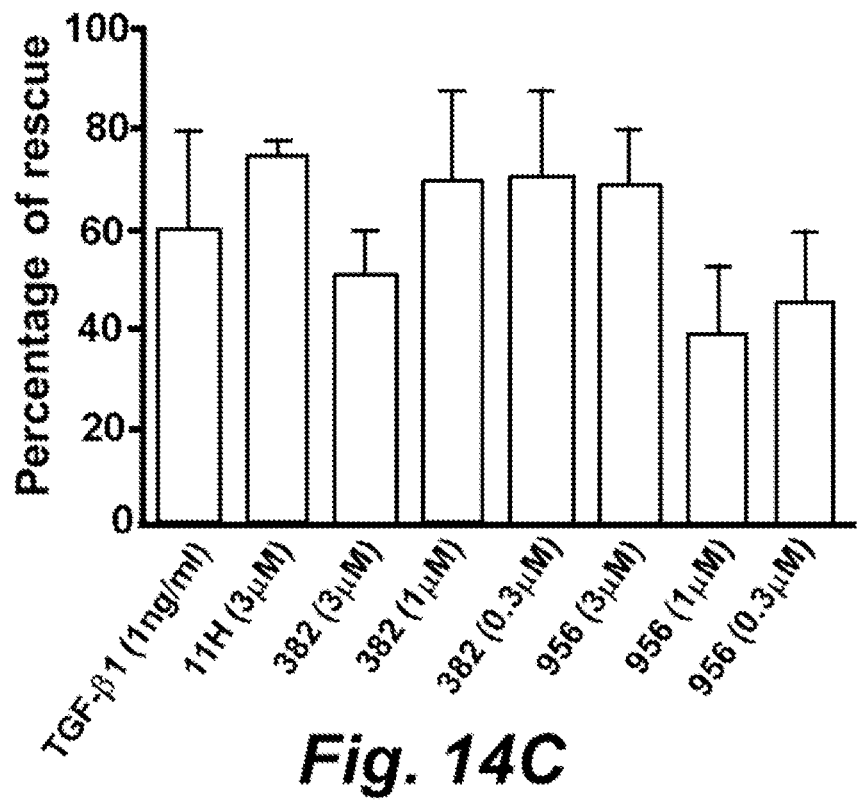
Figure 14D:
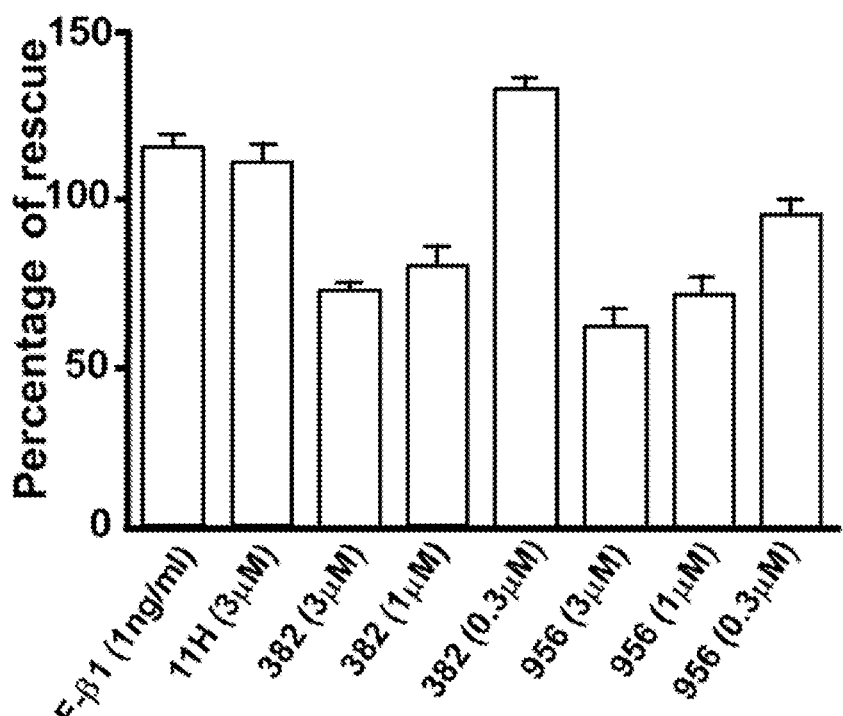
Figure 15:
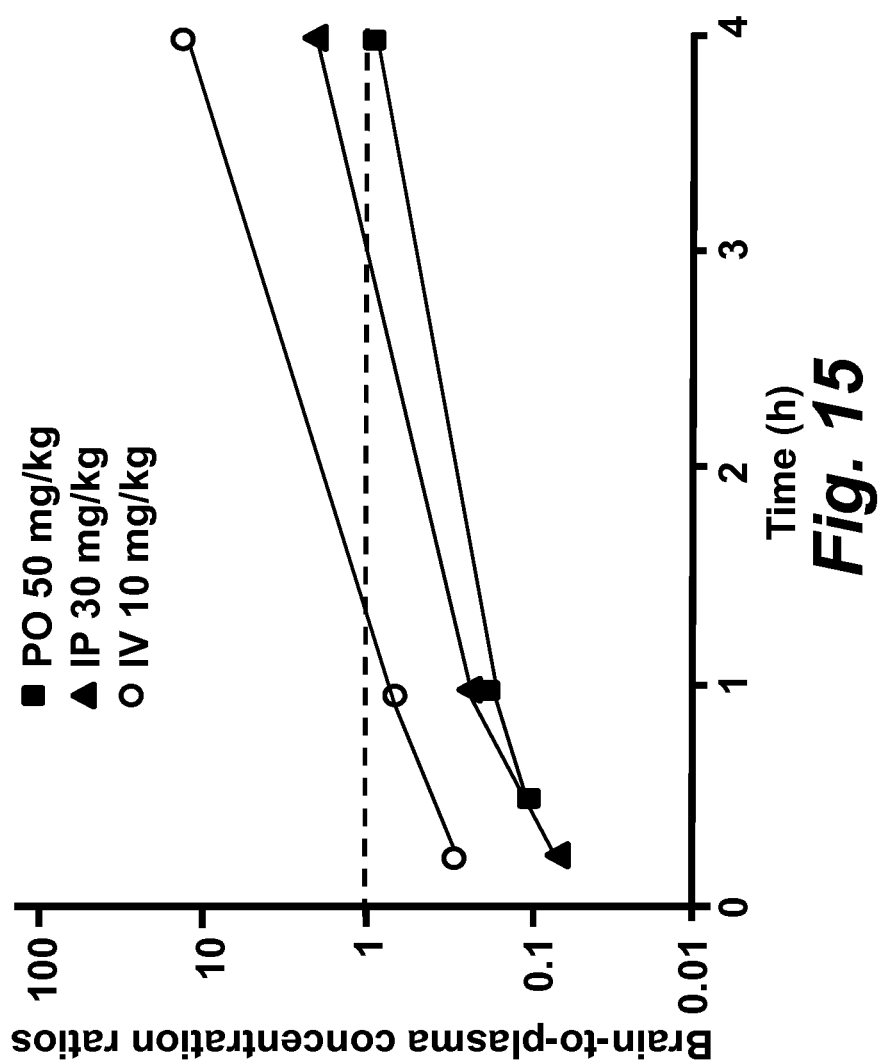
FIG. 15 is a graph illustrating the brain/plasma ratios of compound SRI-011381 (381)

SRI-011381 was cleared from the plasma quickly with an elimination half-life of less than 1 h. However, the apparent volume of distribution (V) was high, at about 8-13 L/kg and this indicated the drug is distributed to tissues, so removal from the plasma may be due to accumulation in tissues in addition to excretion. Consistent with this observation the drug is easily detected in brain tissue and is cleared more slowly from the brain than from plasma. Although brain levels are lower than plasma concentrations, the brain/plasma ratio increases with time, as the drug lingers in the brain tissue, as shown in FIG. 12. The brain/plasma ratio varied with time, but is greater than 0.5 at time points after about 0.5 h (iv) and about 1.5 h (po and ip).

Example 33

Cytotoxicity: In vitro cytotoxicity assays are used to estimate the relative toxicity of test compounds, e.g. a set of chemical analogs prior to efficacy screening. To estimate "basal" toxicity, a cell line such as VERO cells are typically used. Additional factors including drug metabolism can alter the relative toxicity of a compound in vivo. Primary cultures from liver (either laboratory species or human) can be used to assess the relative toxicity of compounds where metabolism may be a factor.

Rat hepatocytes were isolated by collagenase perfusion and allowed to form a monolayer overnight. The test compounds were added to the cells in 5 concentrations up to 250 µM. Cells were incubated with the test article for 20 h and then toxicity determined by the MTT cytotoxicity screen. Toxicity was evaluated against the vehicle control (DMSO) and a positive control, amitriptylin, was included with each experiment.

The results from the cytotoxicity study in rat hepatocytes suggest that both SRI-011382 (382) and its tosylated derivative SRI-011956 are cytotoxic at 50 µM. SRI-011381 has an $LD_{50}$ of greater than 250 µM in this cytotoxicity assay, suggesting that SRI-011474 through SRI-011476 probably have good toxicity profiles.

The objectives of this study were to determine maximum tolerated dose (MTD) and a no observable adverse effect level (NOAEL) in female FVB mice following a daily oral dose administration for 14 consecutive days. After a dose escalation single dose study with doses up to 400 mg/kg, three dose levels were selected for the repeat dose study, 10, 30 and 75 mg/kg, administered ip. The MTD is the maximum dose administered that results in less than 10% body weight loss compared to controls and no other dose limiting adverse effects (e.g. clinical pathology).

In the repeat dose study, clinical signs including hunched posture, hypoactivity and ruffled fur were observed in the high dose group (75 mg/kg) for both drugs. All other animals appeared normal for the duration of the study. However, the high dose of SRI-011382 (compound 382) resulted in lethality to the entire treatment group animals administered SRI-011381 (381) high dose survived to the scheduled sacrifice on Day 15. There were significant differences in body weight or body weight changes in the surviving animals.

Clinical chemistry results showed no significant changes in these parameters for any of the treatment groups. However, mice administered SRI-011381 showed dose dependent changes in hematolog parameters; significantly reduced significantly reduced hematocrit, hemoglobin, RBCs, and WBCs were observed in the high dose group, with minor changes in WBCs only in the 30 mg/kg treatment group. There were no significant differences relative to controls in the 10 mg/kg group. Mice administered SRI-011382 (compound 382) had reduced hematocrit, hemoglobin, RBCs, and WBCs at 30 mg/kg.

Example 34

Neuroprotection Assays: Primary mixed neuronal cultures were exposed to Aβ oligomers and treated with compounds (0 to 10 µM concentration) and cell survival measured using lactate dehydrogenase (LDH) release or by counting 4,6-diamidino-2-phenylindole (DAPI)-stained cells. Aβ oligomers may be produced according to a protocol described by LaDu and coworkers (Dahlgren et al. (2002) *J. Biol. Chem.* 277: 32046-32053, incorporated herein by reference in its entirety.

Such preparations contain mostly oliogomeric Aβ, as demonstrated using atomic force microscopy, and it is toxic to neurons. Neuritic dystrophy in 21 DIV neurons can also be measured by quantifying the tortuosity of neurites as described by Ferreira et al. ((2007) *Mol. Cell. Neurosci.* 9: 220-234 (1997)). Further incubation of these cells with the present compounds provides a sensitive assay for neuroprotection.

Primary hippocampal neurons were isolated from E16 CF1 embryos. Twenty-four-well culture plates were coated with 10 µg/ml poly-L-lysine. Cells were seeded overnight at a density of 30,000 cells/well in DMEM/F-12 medium supplemented with 10% FBS and penicillin/streptomycin, and subsequently maintained in Neurobasal medium containing 2% B27 supplement. Cells were aged for 6-7 days or 21-22 days, then challenged with 5 µM Aβ in the presence or absence of compounds, and assayed for neurotoxicity or neuritic dystrophy, respectively. Cells were treated for 72 h for neurotoxicity assay and 48 h for neuritic dystrophy assay.

At the end of treatment, an equal volume of 4% PFA was added, plates incubated at room temperature for 15 min and then washed three times with DPBS. Cells were kept in the last wash of DPBS at 4° C. until being counted or stained.

For the neurotoxicity assay, live and dead cells were counted according to their morphologies by an investigator blinded to the treatment conditions. The code was only broken after all cells had been counted and results were expressed as % live cells. The rescuing effect of a compound against Aβ was expressed as % rescue based on the following formula:

% RESCUE=(TREATMENT PLUS $A\beta$–$A\beta$ ALONE)/(CULTURE MEDIUM–$A\beta$ ALONE)× 100

Aβ peptide was reconstituted in HFIP, aliquoted into 0.1 mg per tube and lyophilized. The day before treatment, Aβ aliquots were dissolved in 5 pi of DMSO (Sigma), mixed with 195 µl of DPBS pH 7.2, and incubated at 4° C. for 20-24 h. Both compound and Aβ solutions were prepared in 2× concentrations right before treatment. Treatment or treatment control was added before Aβ or Aβ control.

For quantification of neuritic dystrophy, fixed cells were immunostained with a MAP-2 monoclonal antibody (Sigma-Aldrich). After overnight incubation, primary antibody staining was revealed by an ALEXA FLUOR 488®-conjugated secondary antibody (Invitrogen). MAP2 positive dendrites were observed under an inverted fluorescence microscope (Olympus). Dendrites were considered dystrophic when they showed a persistent pattern of increased tortuosity (multiple abrupt turns). To quantify neurite curvature, an established method was modified for assessment of neurite curvature. Neurite tracks were digitized and approximated by a series of connected line segments using ImageJ (NIH). The angle of each segment was determined using a Sigmaplot macro, and the results were averaged to give the 'mean differential curvature'. This parameter reflects the degree of neurite curvature with an increasing value indicating increased curvature. Neurite counting and quantification were performed in randomly selected fields (5 fields/well). All quantitative assessments were done by investigators blinded with respect to treatment conditions.

In Vitro Screening. SRI-011381 and its derivative compounds promote fibrillar β-amyloid ($A\beta_{42}$) clearance by macrophages and protect human neuronal cells from fibrillar $A\beta_{42}$-induced neurotoxicity.

Mouse J774A.1 macrophages and human macrophages that were differentiated from THP-1 monocytic cell lines were treated with fibrillar $A\beta_{42}$ in the absence or presence of SRI-011382 or its derivative compounds (2, 5, or 10 µM) for 24 h. Conditioned medium was harvested and the remaining $A\beta_{42}$ that was not phagocytosed by macrophages was quantified by $A\beta_{42}$ ELISA kit (Invitrogen). Data was normalized to control medium containing the input amount of $A\beta_{42}$. Neurotoxicity induced by fibrillar $A\beta_{42}$ in the conditioned medium was then assessed by incubating Neuro-2a neuroblastoma cells with conditioned medium for 24 h followed by MTS-based viability assay. Data was normalized to control cells without fibrillar $A\beta_{42}$ treatment.

Figure 16A:
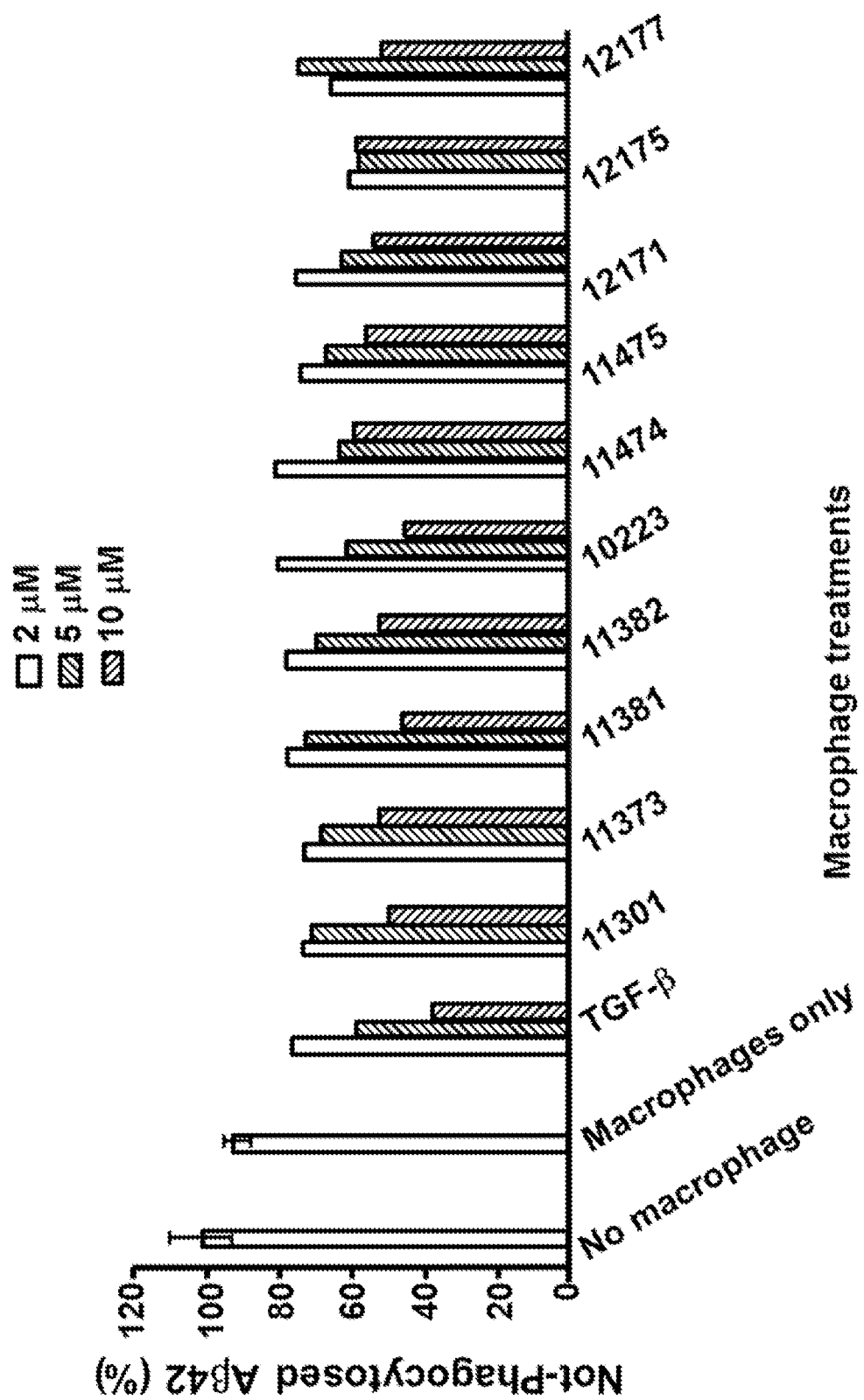
FIGS. 16A and 16B are graphs illustrating SRI-11381 (compound 381) and its derivative compounds promote fibrillar Aβ$_{42}$ clearance by THP-1 macrophages (FIG. 16A) or J774A.1 macrophages (FIG. 16B).
Figure 16B:
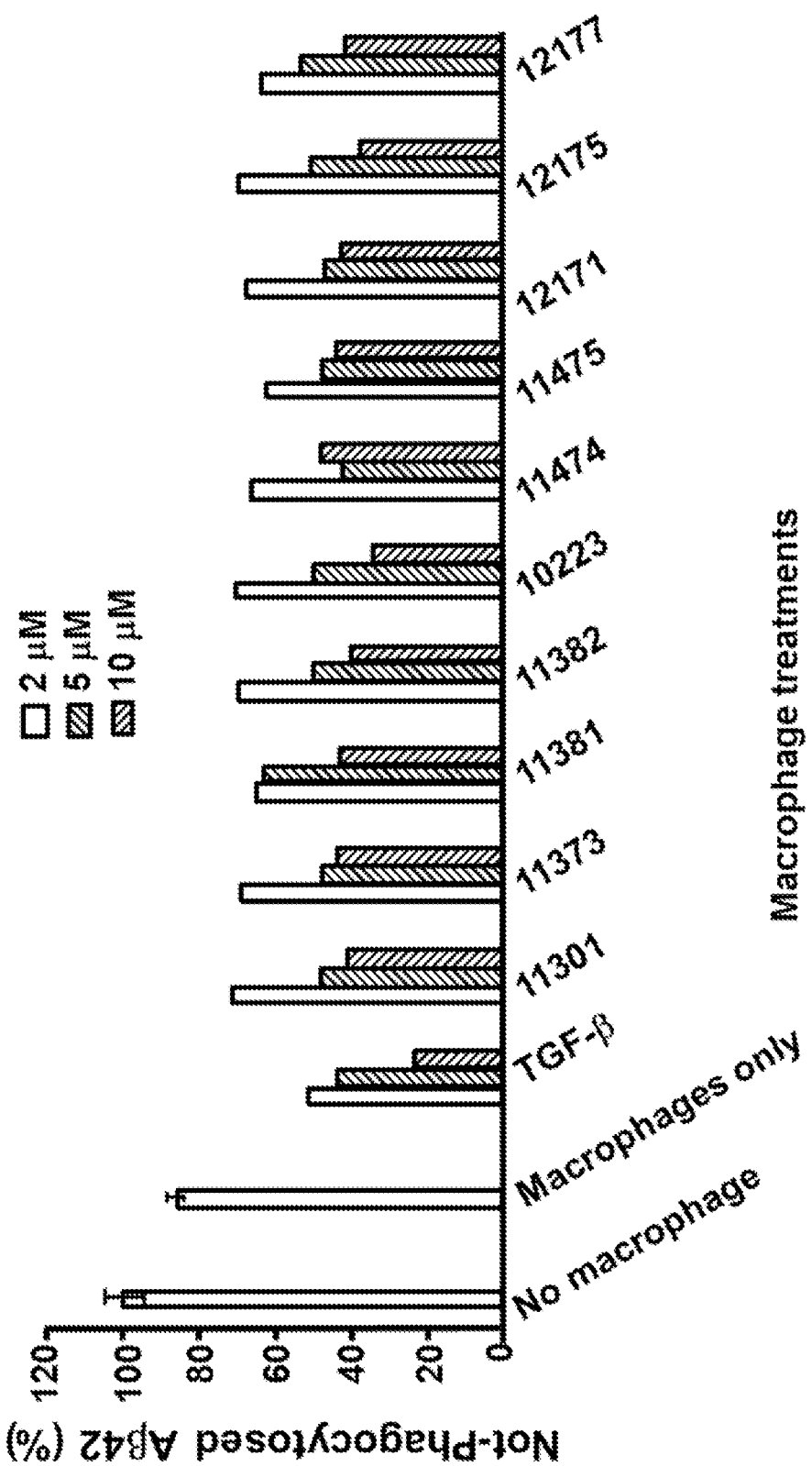

As shown in FIGS. 16A and 16B, SRI-011381 and its derivative compounds promoted fibrillar $A\beta_{42}$ clearance by macrophages, as demonstrated by the dose-dependent decreases of $A\beta_{42}$ in the conditioned medium derived from compound-treated macrophages. Results from TGF-β (20, 50, or 100 pg/mL) treated macrophages were included for comparison and indicated that SRI compounds are as potent as TGF-β to promote fibrillar Aβ$_{42}$ phagocytosis by macrophages.

Figure 17A:
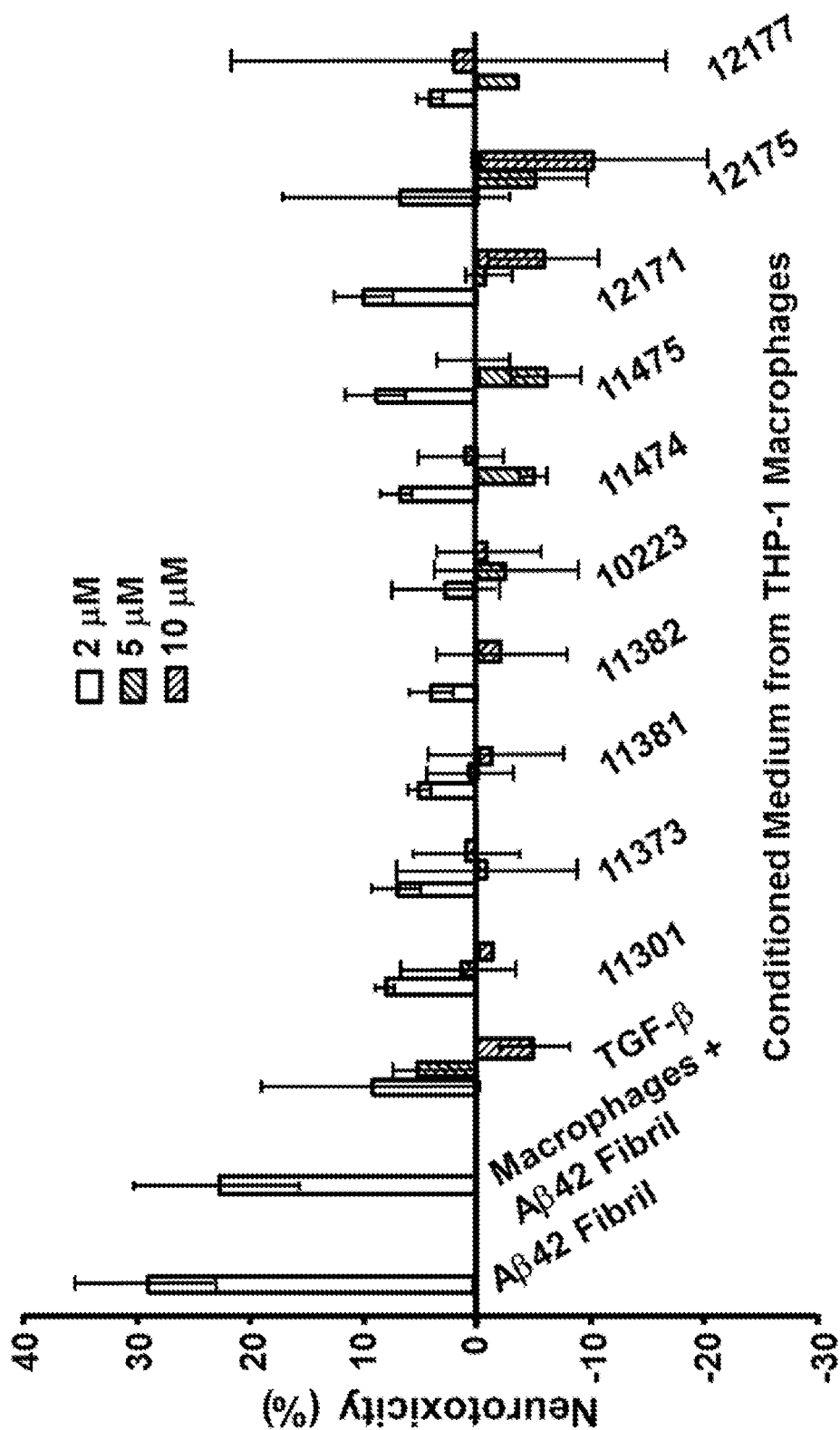
FIGS. 17A and 17B are graphs illustrating SRI-011381 (381) and its derivative compounds protect human neuronal cells from fibrillar Aβ$_{42}$-induced neurotoxicity in medium conditioned by THP-1 macrophages (FIG. 17A) or J774A.1 macrophages (FIG. 17B).
Figure 17B:
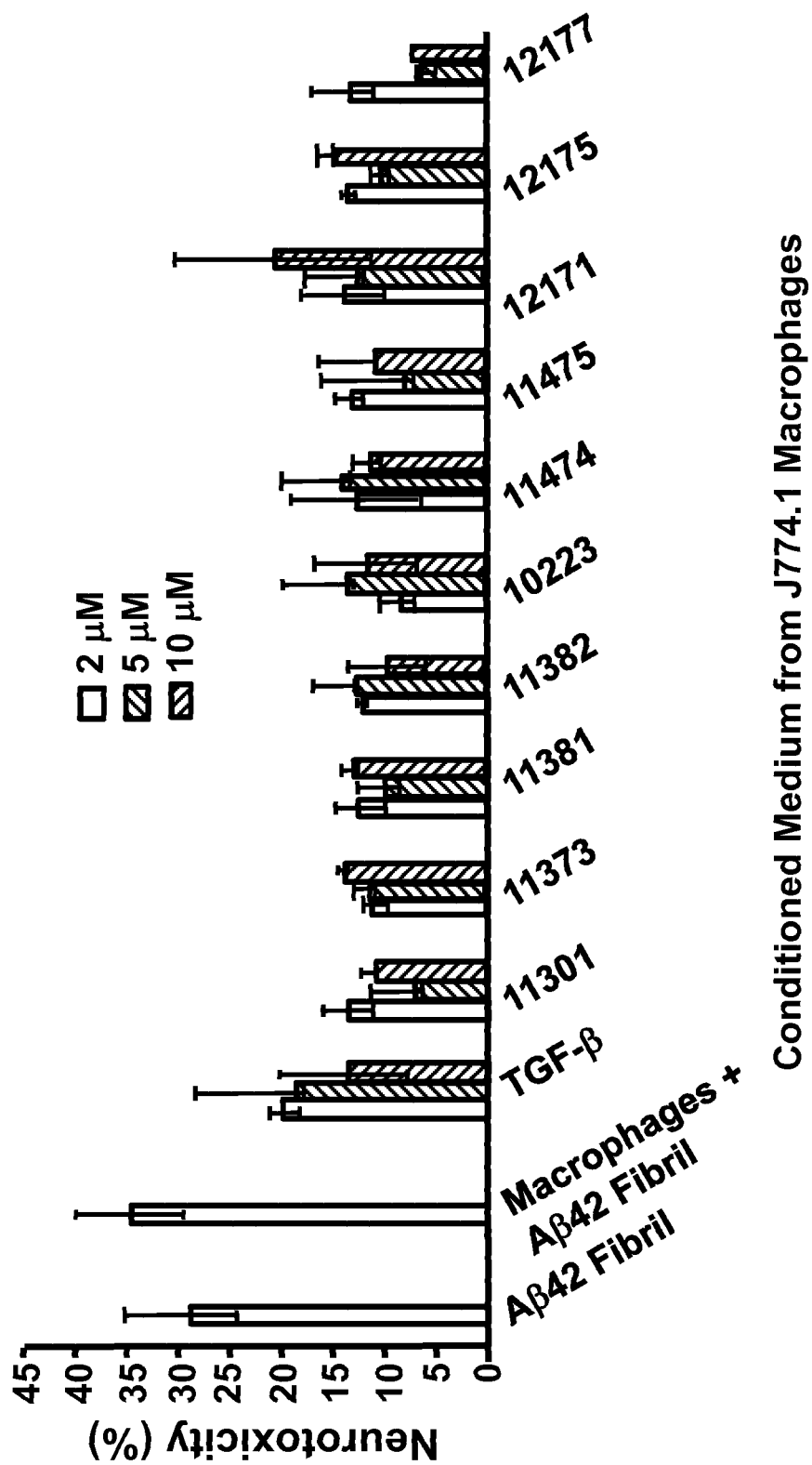

In addition, as shown in FIGS. 17A and 17B, the compounds also protected human neuronal cells from fibrillar Aβ$_{42}$-induced neurotoxicity to the same extent as TGF-β does by promoting macrophage-mediated clearance of fibrillar Aβ$_{42}$.

In Vivo Models

Figure 18:
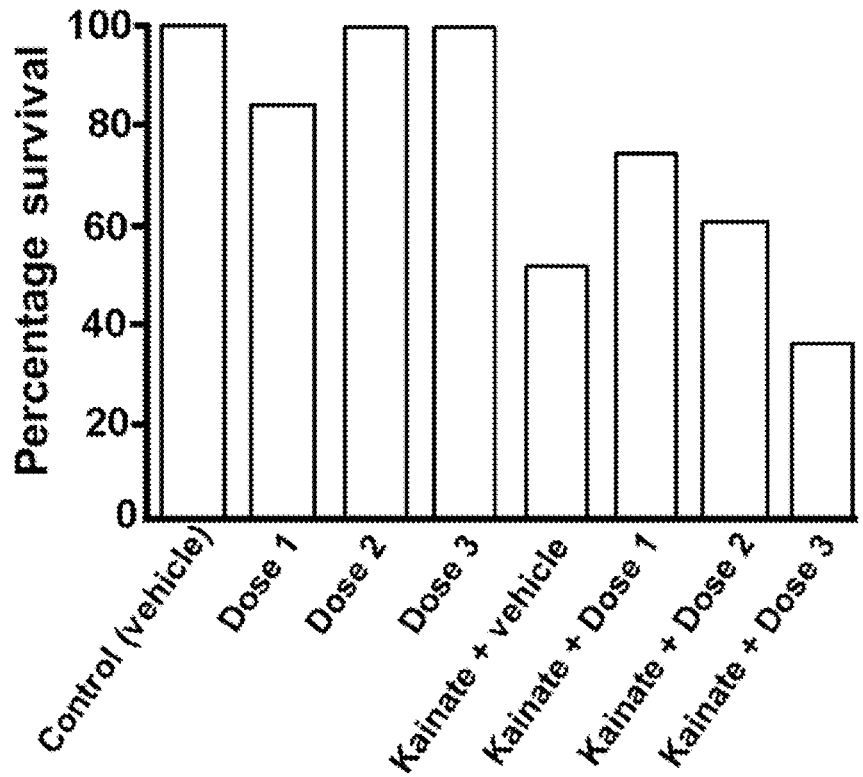
FIG. 18 is a graph illustrating mouse survival following kainate/SRI-011381 (381) delivery.
Figure 19:
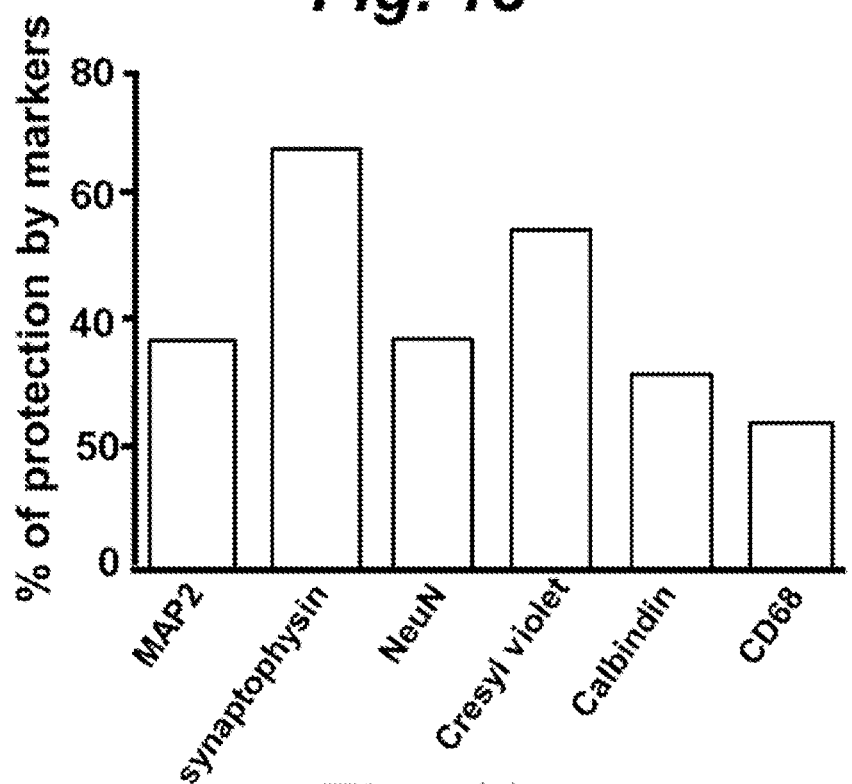
FIG. 19 is a graph illustrating neuroprotection with SRI-011381 (381) in the kainate model.

To study the potential neuroprotective effect of SRI-011381, FvB wild-type mice were pre-treated with compound or vehicle for 3 days before excitotoxic injury was induced with kainic acid (10 mg/kg). Mice continued to receive daily injections of compound until they were sacrificed at day 5 after kainic acid injury. Kainic acid treatment alone caused a roughly 50% lethality in this experiment (lethality greatly varies in this model and is very difficult to control, but survivors from experiments with greater than 25% lethality typically show significant neurodegeneration in the hippocampus). Mice were initially treated at 10, 30 and 60 mg SRI-011381/kg daily (dose 1, 2, 3, respectively) and a significant reduction in lethality in mice treated with 10 mg/kg was observed, but an increase in lethality was observed at the highest drug dose, as shown in FIG. 18.

One mouse died with drug alone at the lowest dose on day 2 of injection (1 day before any mice were treated with kainic acid). This was likely a random event and not caused by the drug. Based on these result and the pharmacological data, only the low dose was analyzed for neuropathological changes.

Brains were removed, fixed with paraformaldehyde, sectioned into 40 μM sections using a cryomicrotome and stained with cresyl violet, or immunohistochemical methods. Sections were analyzed for synaptophysin, MAP2, and NeuN by confocal quantitative analysis of neurodegeneration. All observers were completely blinded to the treatment conditions of the mice.

Figure 20:
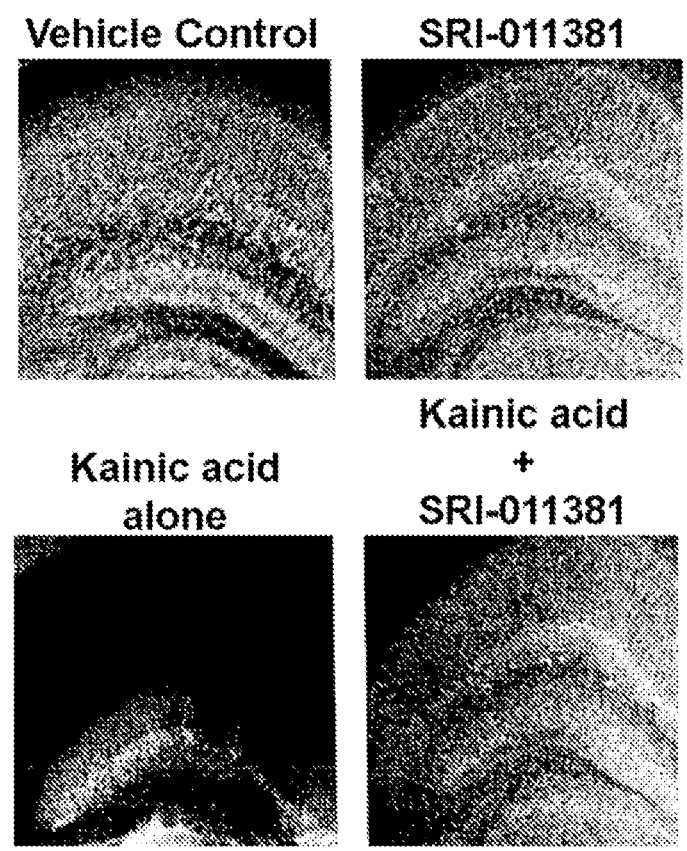
FIG. 20 is a series of digital confocal images illustrating neuroprotection with SRI-011381 (381) in the kainate model.

A significant loss of neuronal (NeuN, cresyl violet, calbindin) synaptic (synaptophysin), and dendritic (MAP2) cell markers and a strong increase in microglial CD68 expression was found. SRI-011381 reversed or prevented neuronal damage consistently by at least 30% for all neuronal markers. As an example, the loss of dendritic integrity with kainic acid and the protection with SRI-011381 are shown in FIG. 20. The drug also reduced CD68 expression by more than 20%. While glial markers are a good indicator for neuronal injury, it was found recently that they are not a good correlate of neuroprotection with treatments that almost completely restore neuronal integrity (treatment with Macrophage colony stimulating factor (MCSF) and interleukin-34 (IL34)). It is, therefore, possible that microglia are still activated while neurons are being preserved. It has been shown that calbindin is a marker of neuronal damage not only in acute excitotoxic injury but also in Aβ transgenic mouse models. This marker was tested in the MCSF/IL34 study and found it to be a predictor of neuronal rescue. Consistent with the neuroprotective effects of SRI-011381, calbindin loss was reduced by 30% in the current study.

What is claimed is:

1. A TGF-β signaling agonist, wherein the agonist, or a pharmaceutically acceptable salt thereof, is selected from the group consisting of the formulas:

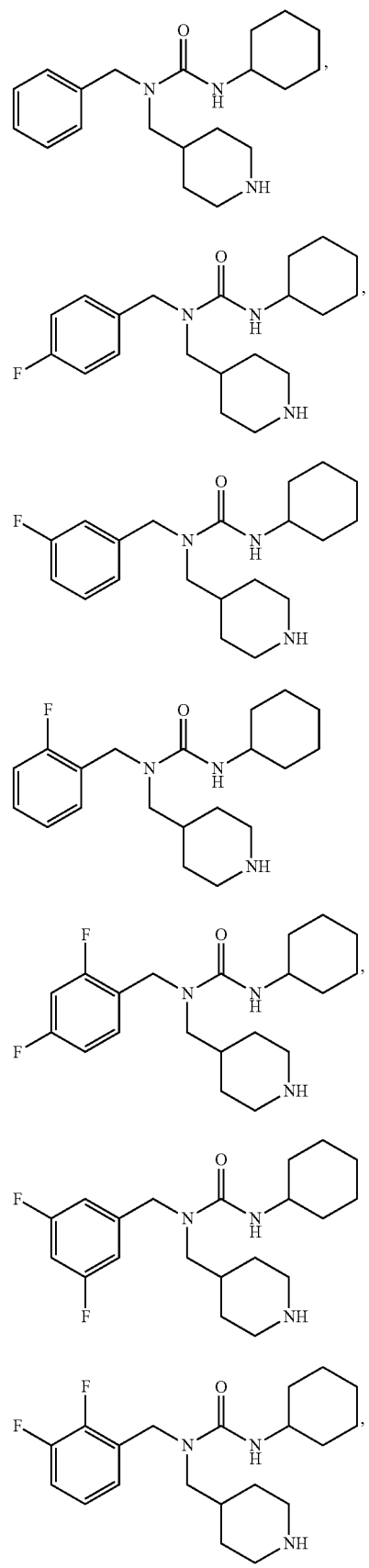

69
-continued
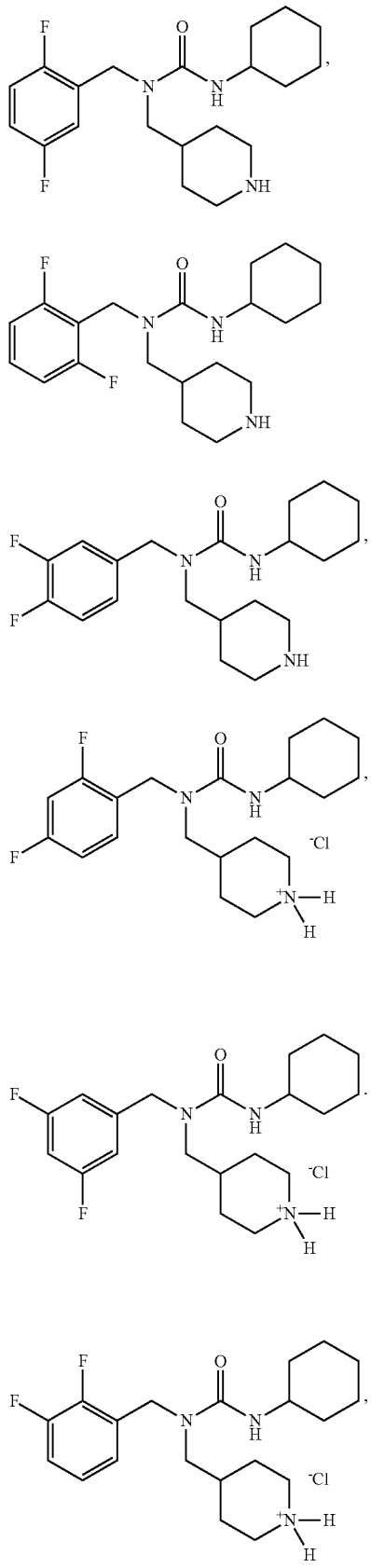
70
-continued
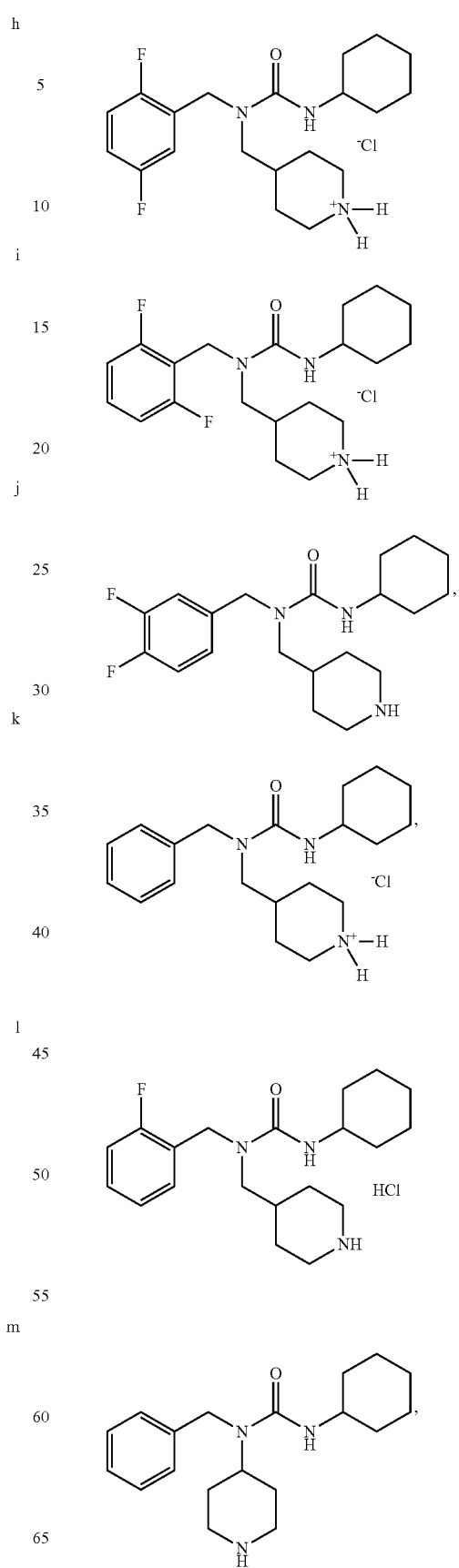

t

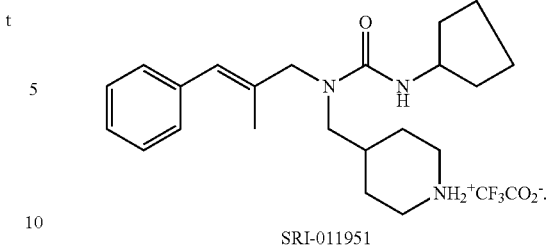

SRI-011951

2. The composition of claim 1, wherein the agonist is protonated at the N-piperidine and the pharmaceutically acceptable salt is a chloride, tosylate, or trifuoroacetate.

3. The composition of claim 1, wherein said composition is a pharmaceutical composition comprising a therapeutically effective amount of the TGF-β signaling agonist and at least one of a pharmaceutically acceptable excipient and a pharmaceutically acceptable carrier.

4. A method for increasing TGF-β signaling activity of a cell, comprising the step of contacting the cell with a composition comprising an effective amount of a TGF-β signaling agonist, wherein the agonist, or a pharmaceutically acceptable salt thereof, is selected from the group consisting of the formulas:

a

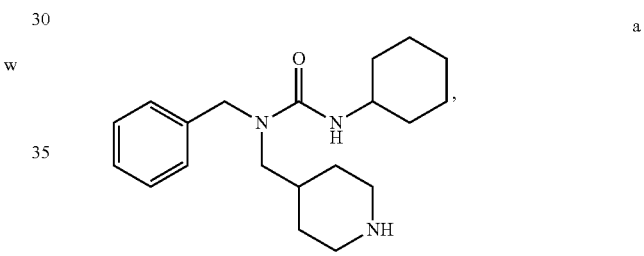

b

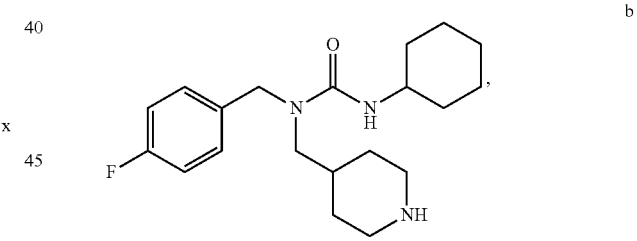

c

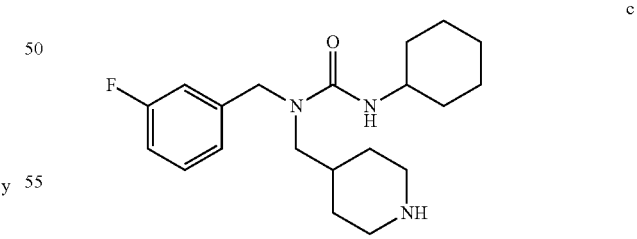

d

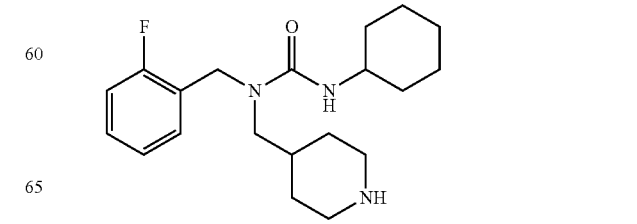

-continued

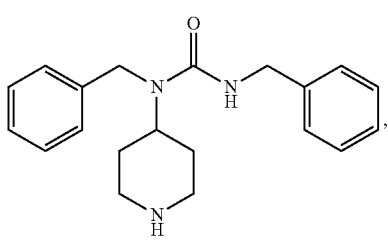

u

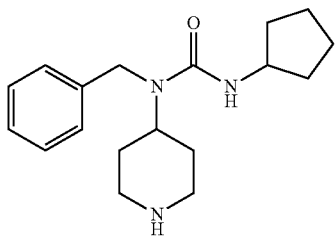

v

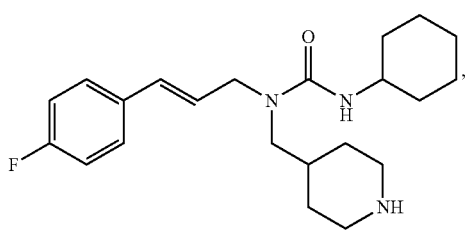

w

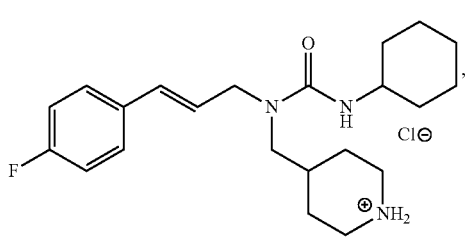

x

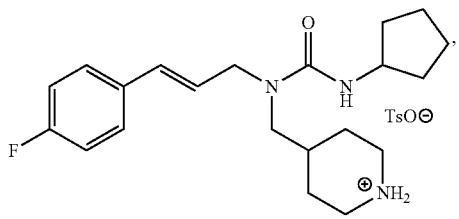

y

, and

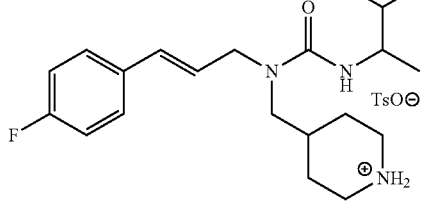

e
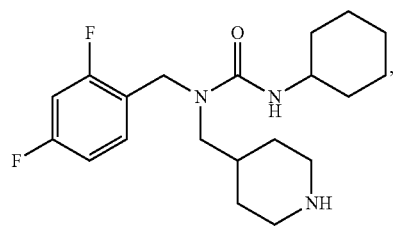
f
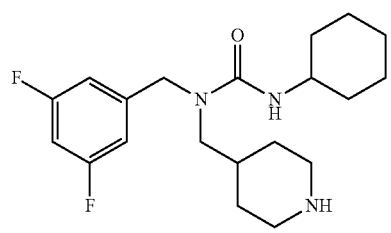
g
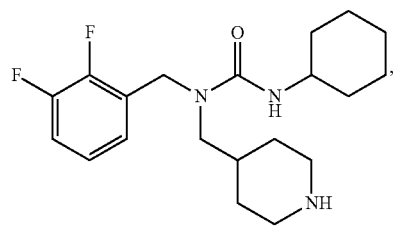
h
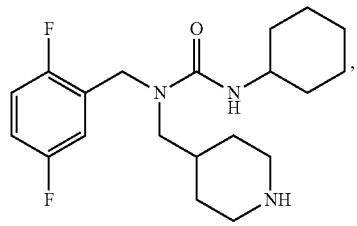
i
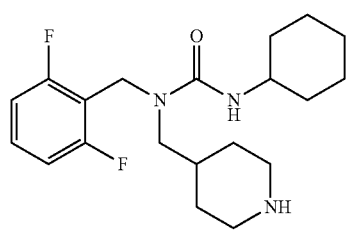
j
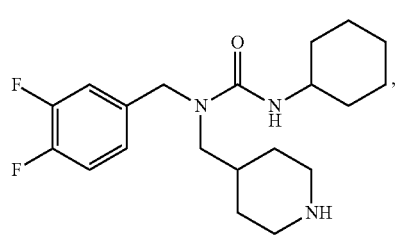
k
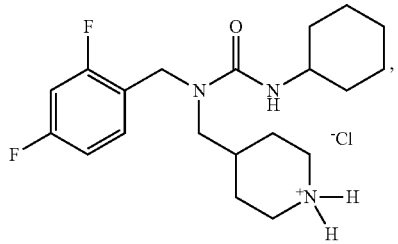
l
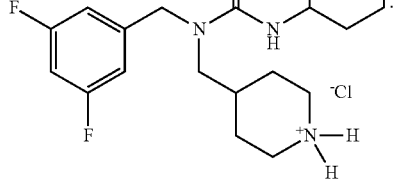
m
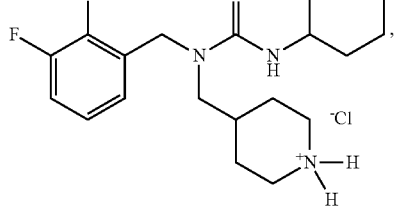
n
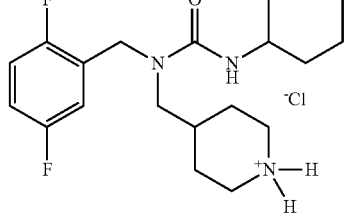
o
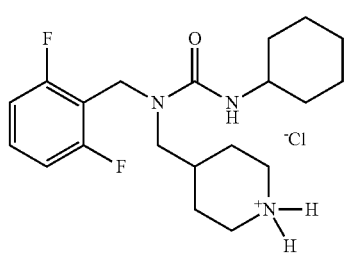
p
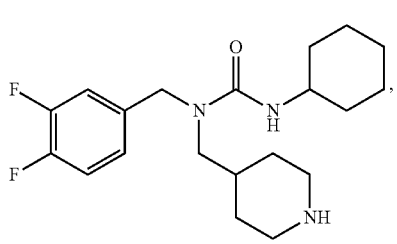

q 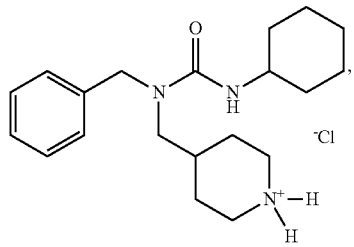
r 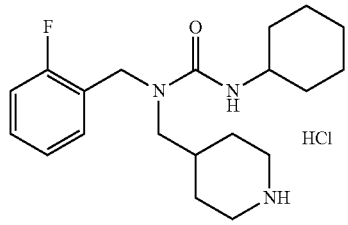
s 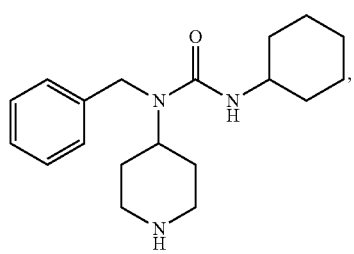
t 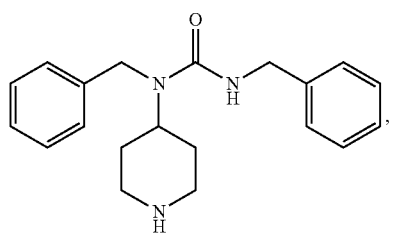
u 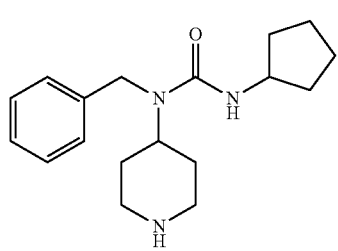
v 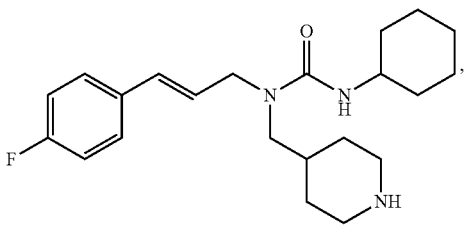
w 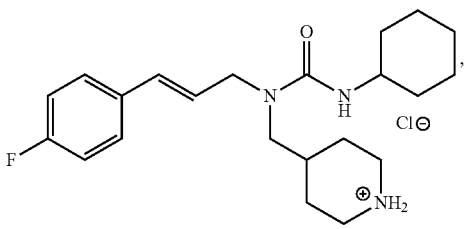
x 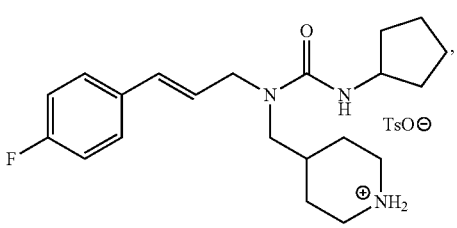
y 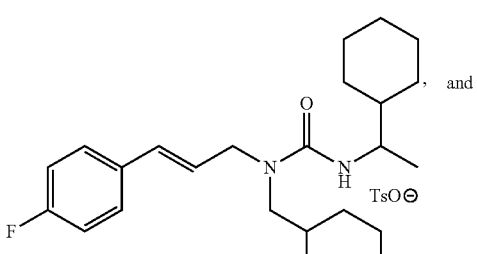
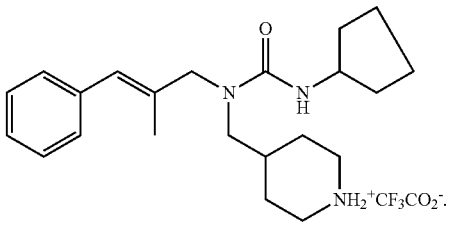
SRI-011951
5. The method of claim 4, wherein the composition comprising the TGF-β signaling agonist further comprises a pharmaceutically acceptable carrier.
* * * * *

UNITED STATES PATENT AND TRADEMARK OFFICE
CERTIFICATE OF CORRECTION

PATENT NO. : 9,796,674 B2  
APPLICATION NO. : 14/776313  
DATED : October 24, 2017  
INVENTOR(S) : Tanga et al.

Page 1 of 1

It is certified that error appears in the above-identified patent and that said Letters Patent is hereby corrected as shown below:

On the Title Page

Please add the following to the applicant paragraph:  
--THE UNITED STATES GOVERNMENT AS REPRESENTED BY THE DEPARTMENT OF VETERANS AFFAIRS, Washington DC (US)--

Please also add an assignee section:  
--THE BOARD OF TRUSTEES OF THE LELAND STANFORD JUNIOR UNIVERSITY, Palo Alto, CA (US); SRI INTERNATIONAL, Menlo Park, CA (US); THE UNITED STATES GOVERNMENT AS REPRESENTED BY THE DEPARTMENT OF VETERANS AFFAIRS, Washington DC (US)--

Signed and Sealed this  
Twenty-eighth Day of December, 2021

Drew Hirshfeld  
*Performing the Functions and Duties of the*  
*Under Secretary of Commerce for Intellectual Property and*  
*Director of the United States Patent and Trademark Office*